(12) United States Patent
Ha et al.

(10) Patent No.: US 12,145,898 B2
(45) Date of Patent: Nov. 19, 2024

(54) COMPOUND, COMPOSITION COMPRISING SAME, AND ORGANIC LIGHT EMITTING DIODE COMPRISING SAME

(71) Applicant: LG CHEM, LTD., Seoul (KR)

(72) Inventors: Jae Seung Ha, Daejeon (KR); Seong So Kim, Daejeon (KR); Minseung Chun, Daejeon (KR)

(73) Assignee: LG Chem, Ltd., Seoul (KR)

( * ) Notice: Subject to any disclaimer, the term of this patent is extended or adjusted under 35 U.S.C. 154(b) by 603 days.

(21) Appl. No.: 16/972,912

(22) PCT Filed: Sep. 20, 2019

(86) PCT No.: PCT/KR2019/012212
§ 371 (c)(1),
(2) Date: Dec. 7, 2020

(87) PCT Pub. No.: WO2020/060271
PCT Pub. Date: Mar. 26, 2020

(65) Prior Publication Data
US 2021/0253512 A1     Aug. 19, 2021

(30) Foreign Application Priority Data
Sep. 21, 2018   (KR) .......................... 10-2018-0113949

(51) Int. Cl.
C07C 211/54    (2006.01)
H10K 85/60     (2023.01)
H10K 50/15     (2023.01)
H10K 50/17     (2023.01)

(52) U.S. Cl.
CPC .......... C07C 211/54 (2013.01); H10K 85/622 (2023.02); H10K 85/633 (2023.02); H10K 50/15 (2023.02); H10K 50/17 (2023.02)

(58) Field of Classification Search
None
See application file for complete search history.

(56) References Cited

U.S. PATENT DOCUMENTS

| | | |
|---|---|---|
| 6,444,333 B1 | 9/2002 | Okada et al. |
| 2003/0118866 A1 | 6/2003 | Oh et al. |
| 2004/0189190 A1* | 9/2004 | Suzuri .................. H10K 85/631 |
| | | 313/504 |
| 2010/0330480 A1 | 12/2010 | Itami |
| 2011/0147717 A1* | 6/2011 | LeCloux .............. H10K 85/633 |
| | | 564/429 |
| 2011/0253985 A1 | 10/2011 | Wang et al. |
| 2011/0253986 A1 | 10/2011 | Wang et al. |
| 2012/0187382 A1* | 7/2012 | Rostovtsev .......... H10K 85/631 |
| | | 257/E51.026 |
| 2012/0187391 A1 | 7/2012 | Kato et al. |
| 2013/0048964 A1* | 2/2013 | Takeda ................. H10K 85/626 |
| | | 257/E51.026 |
| 2017/0018718 A1 | 1/2017 | Jang et al. |
| 2017/0317291 A1 | 11/2017 | Hayashi et al. |
| 2022/0204438 A1* | 6/2022 | Kubota ................ H10K 85/631 |

FOREIGN PATENT DOCUMENTS

| | | |
|---|---|---|
| CN | 1416301 | 5/2003 |
| JP | 2000-119644 A | 4/2000 |
| JP | 2009-282302 A | 12/2009 |
| JP | 2010-118653 A | 5/2010 |
| JP | 2011-7925 A | 1/2011 |
| JP | 4736336 B2 | 7/2011 |
| JP | 2011-173973 A | 9/2011 |
| JP | 2012111719 A | 6/2012 |
| KR | 10-2012-0070608 A | 6/2012 |
| KR | 10-2012-0086319 A | 8/2012 |
| KR | 10-1584484 A | 1/2016 |
| KR | 10-2017-0086555 A | 7/2017 |
| WO | 2011/102112 A1 | 8/2011 |

* cited by examiner

*Primary Examiner* — Robert S Loewe
(74) *Attorney, Agent, or Firm* — Bryan Cave Leighton Paisner LLP

(57) ABSTRACT

The present disclosure relates to a compound of Chemical Formula 1, and a composition and an organic light emitting device including the same. The composition including the compound or a cured material thereof is included in an organic material layer of the organic light emitting device.

[Chemical Formula 1]

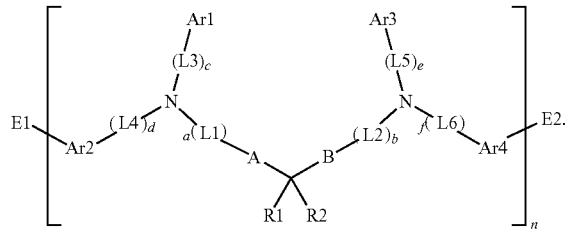

20 Claims, 1 Drawing Sheet

[FIG. 1]
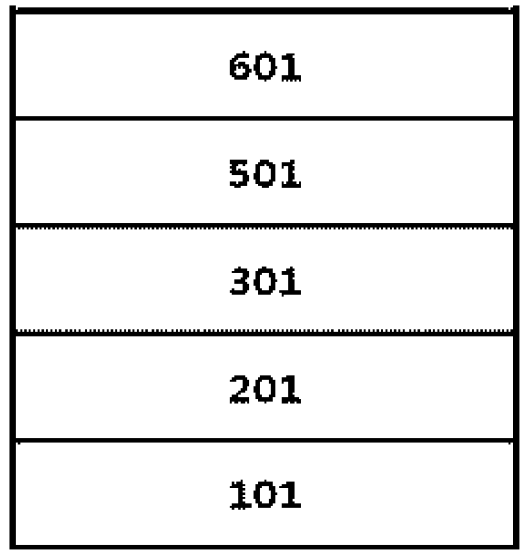
[FIG. 2]
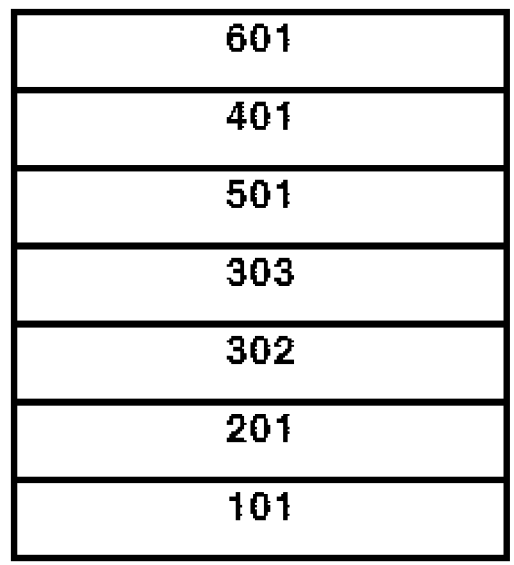

COMPOUND, COMPOSITION COMPRISING SAME, AND ORGANIC LIGHT EMITTING DIODE COMPRISING SAME

CROSS-REFERENCE TO RELATED APPLICATIONS

This application is a National Stage Application of International Application No. PCT/KR2019/012212, filed on Sep. 20, 2019, which claims the benefit of priority based on Korean Patent Application No. 10-2018-0113949, filed, on Sep. 21, 2018, the disclosure of which is incorporated herein by reference in its entirety.

TECHNICAL FIELD

The present specification relates to a compound, a composition including the compound, and an organic light emitting device including the same.

BACKGROUND ART

An organic light emission phenomenon is one of examples converting a current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively. The holes and the electrons injected to the organic material layer recombine to form excitons, and light emits when these excitons fall back to the ground state. An organic light emitting device using such a principle may be generally formed with a cathode, an anode, and an organic material layer placed therebetween, for example, an organic material layer including a hole injection layer, a hole transfer layer, a light emitting layer and an electron transfer layer.

Materials used in an organic light emitting device are mostly pure organic materials or complex compounds in which organic materials and metals form complexes, and may be divided into hole injection materials, hole transfer materials, light emitting materials, electron transfer materials, electron injection materials and the like depending on the application. Herein, as the hole injection material or the hole transfer material, organic materials having a p-type property, that is, organic materials readily oxidized and having an electrochemically stable state when oxidized, are generally used. Meanwhile, as the electron injection material or the electron transfer material, organic materials having an n-type property, that is, organic materials readily reduced and having an electrochemically stable state when reduced, are generally used. As the light emitting layer material, materials having both a p-type property and an n-type property, that is, materials having a stable form in both oxidized and reduced states, are preferred, and materials having high light emission efficiency converting, when excitons are formed, the excitons to light are preferred.

In addition to the properties described above, it is preferred that materials used in an organic light emitting device additionally have properties as follows.

First, materials used in an organic light emitting device preferably have excellent thermal stability. This is due to joule heat produced by charge migration in the organic light emitting device. NPB normally used as a hole transfer layer material currently has a glass transition temperature of 100° C. or lower, and has a problem in that it is difficult to use in organic light emitting devices requiring a high current.

Second, in order to obtain a highly efficient organic light emitting device capable of low voltage driving, holes or electrons injected into the organic light emitting device need to be smoothly transferred to a light emitting layer, and at the same time, the injected holes and electrons need to be kept from escaping out of the light emitting layer. For this, materials used in the organic light emitting device need to have a proper band gap and a HOMO or LUMO energy level. PEDOT: PSS currently used as a hole transfer material in an organic light emitting device manufactured using a solution coating method has a lower LUMO energy level compared to a LUMO energy level of organic materials used as a light emitting layer material, and therefore, has a problem in manufacturing an organic light emitting device with high efficiency and long lifetime.

In addition thereto, materials used in an organic light emitting device need to have excellent chemical stability, charge mobility, and interface property with electrodes or adjacent layers. In other words, materials used in an organic light emitting device need to undergo less material deformation caused by moisture or oxygen. In addition, by having proper hole or electron mobility, the materials need to be able to maximize exciton formation through balancing hole and electron density in a light emitting layer of the organic light emitting device. For device stability, the materials also need to improve an interface with electrodes including metals or metal oxides.

Accordingly, development of organic materials fulfilling such requirements has been required in the art.

DISCLOSURE

Technical Problem

The present specification is directed to providing a compound, a composition including the same, and an organic light emitting device including the same.

Technical Solution

One embodiment of the present specification provides a compound represented by the following Chemical Formula 1 and having a molecular weight greater than or equal to 1,000 g/mol.

[Chemical Formula 1]

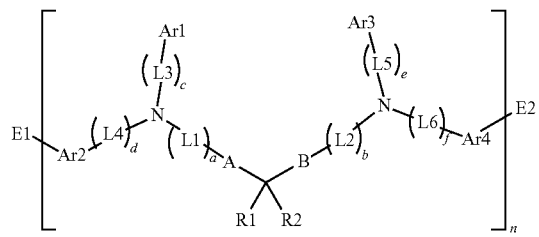

In Chemical Formula 1,
R1 and R2 are the same as each other, and are hydrogen; deuterium; an alkyl group having 1 to 15 carbon atoms; or an aryl group having 6 to 10 carbon atoms, or bond to each other to form a cycloalkyl group,
A and B are the same as each other, and are a substituted or unsubstituted phenylene group, L1 and L2 are the same as each other, L3 and L5 are the same as each other, L4 and L6 are the same as each other, and L1 to L6 are a substituted or unsubstituted arylene group, Ar2 and Ar4 are the same as each other, and are a substituted or unsubstituted arylene group, Ar1 and Ar3 are the same as each other, and are a substituted or unsubstituted aryl group, at least one of L1 to L6 and Ar1 to Ar4 is substituted with an alkyl group; a cycloalkyl group; or an adamantyl group, E1 and E2 are the same as each other, and are hydrogen; deuterium; a halogen group; a substituted or unsubstituted alkyl group; a substituted or unsubstituted aryl group; or a substituted or unsubstituted siloxane group, a to f are each an integer of 0 to 5, and when a to f are an integer of 2 or greater, linking groups in the parentheses are the same as or different from each other, n is an integer of 1 or greater, and when n is 1, E1 and E2 are hydrogen or deuterium, and when R1 and R2 are a phenyl group and n is 1, Ar1 and Ar3 are a phenyl group substituted with an alkyl group or an alkenyl group; or a substituted or unsubstituted polycyclic aryl group, and Ar2 and Ar4 are a phenylene group substituted with an alkyl group or an alkenyl group; or a substituted or unsubstituted polycyclic arylene group.

Another embodiment of the present specification provides a composition including the compound described above.

Another embodiment of the present specification provides an organic light emitting device including a first electrode; a second electrode provided to face the first electrode; and an organic material layer having one or more layers provided between the first electrode and the second electrode, wherein one or more layers of the organic material layer include the composition described above or a cured material thereof.

Advantageous Effects

A compound according to the present disclosure can be used as a material of an organic material layer of an organic light emitting device, and the compound can be used in a solution process, and as a result, devices having large area can be manufactured. Particularly, by connecting a light emitting material using the compound as a material capable of increasing solubility, a light emitting layer of an organic light emitting device can be formed using a solution process, and processability can be greatly improved thereby.

A compound according to one embodiment of the present specification can be used as a material of an organic material layer of an organic light emitting device, and is capable of providing low driving voltage, high light emission efficiency and high lifetime properties.

DESCRIPTION OF DRAWINGS

FIGS. 1 and 2 illustrate examples of an organic light emitting device according to one embodiment of the present specification.

REFERENCE NUMERAL

101: Substrate
201: Anode
301: Hole Transfer Layer
302: First Hole Transfer Layer
303: Second Hole Transfer Layer
501: Light Emitting Layer
401: Electron Transfer Layer
601: Cathode

[Mode for Disclosure]

Hereinafter, the present specification will be described in more detail.

In the present specification, a description of one member being placed "on" another member includes not only a case of the one member adjoining the another member but a case of still another member being present between the two members.

In the present specification, a description of a certain part "including" certain constituents means capable of further including other constituents, and does not exclude other constituents unless particularly stated on the contrary.

Throughout the specification of the present application, the term "combination thereof" included in a Markush-type expression means a mixture or a combination of one or more selected from the group consisting of constituents described in the Markush-type expression, and means including one or more selected from the group consisting of the constituents.

One embodiment of the present specification provides a compound represented by Chemical Formula 1 and having a molecular weight of 1,000 g/mol or greater.

The compound according to one embodiment of the present specification has amine groups symmetrically present on both sides based on the sp3 carbon in the following structural formula, and thereby has properties of high light emission efficiency and high lifetime when manufacturing an organic light emitting device, and is capable of enhancing processability by allowing a solution process with enhanced solubility and coatability compared to compounds having a molecular weight of less than 1,000 g/mol.

In one embodiment of the present specification, the compound represented by Chemical Formula 1 has a molecular weight of 1,000 g/mol to 50,000,000 g/mol. Particularly, when solubility and coatability are enhanced by satisfying the above-mentioned range, coating uniformity and durability of a thin film formed in the solution process increase.

Accordingly, processability may be enhanced by reducing possibility of being used as a trap electrically and a leakage current.

As for the molecular weight according to the present specification, the molecular weight of a monomer is measured using liquid chromatography-mass spectrometer, and a weight average molecular weight is measured for a polymer using gas chromatography-mass spectrometer.

In one embodiment of the present specification, the compound represented by Chemical Formula 1 is plane symmetric. Plane symmetry according to the present specification means both sides being the same based on the dotted line of the following chemical formula. In other words, it means corresponding substituents being the same based on the dotted line. For example, A and B are the same, R1 and R2 are the same, and Ar1 and Ar3 are the same.

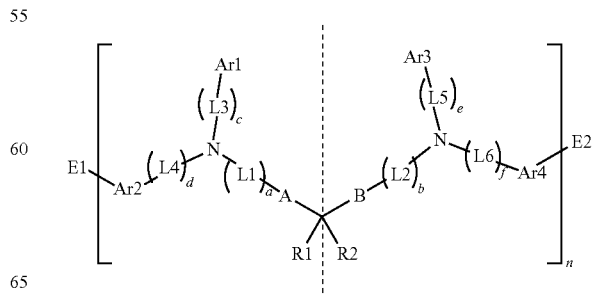

A compound which is symmetrical based on the dotted line as the above-described chemical formula are readily synthesized and readily incorporated into a process, and when used in an organic light emitting device, excellent device performance and thin film properties are obtained compared to asymmetric compounds.

In one embodiment of the present specification, compounds having solubility for proper organic solvents are preferred as the compound of Chemical Formula 1.

Hereinafter, substituents of the present specification will be described in detail, however, the substituents are not limited thereto.

In the present specification, means a site bonding to other substituents or bonding sites.

In the present specification, the term "substitution" means a hydrogen atom bonding to a carbon atom of a compound is changed to another substituent. The position of substitution is not limited as long as it is a position at which the hydrogen atom is substituted, that is, a position at which a substituent can substitute, and when two or more substituents substitute, the two or more substituents may be the same as or different from each other.

In the present specification, the term "substituted or unsubstituted" means being substituted one or more substituents selected from the group consisting of deuterium; a halogen group; a cyano group; an imide group; an amide group; an alkyl group; a cycloalkyl group; an adamantyl group; an alkoxy group; a thioalkyl group; an alkenyl group; an aryloxy group; an aralkyl group; a silyl group; a phosphine oxide group; an amine group; an aryl group; and a heterocyclic group, or unsubstituted, or being substituted with a substituent linking two or more substituents among the substituents illustrated above, or being unsubstituted.

In the present specification, examples of the halogen group include fluorine, chlorine, bromine or iodine.

In the present specification, the number of carbon atoms of the imide group is not particularly limited, but is preferably from 1 to 30. Specifically, compounds having structures as below may be included, however, the imide group is not limited thereto.

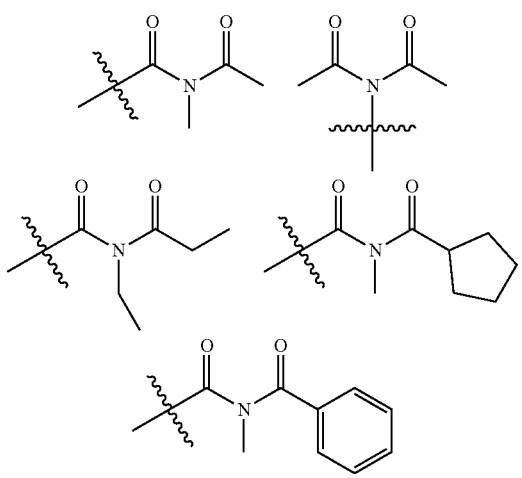

In the present specification, in the amide group, the nitrogen of the amide group may be substituted with a linear, branched or cyclic alkyl group having 1 to 30 carbon atoms or an aryl group having 6 to 30 carbon atoms. Specifically, compounds having the following structural formulae may be included, however, the amide group is not limited thereto.

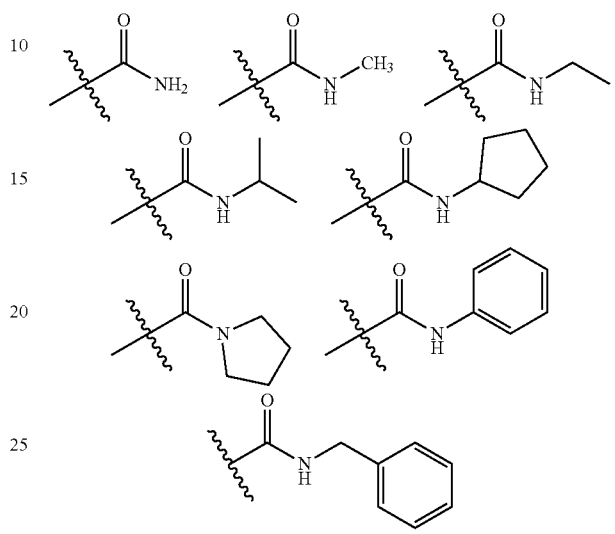

In the present specification, the alkyl group may be linear, branched or cyclic, and although not particularly limited thereto, the number of carbon atoms is preferably from 1 to 50. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 60 carbon atoms. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 30. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group may be linear or branched, and although not particularly limited thereto, the number of carbon atoms is preferably from 2 to 30. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl) vinyl-1-yl, 2,2-bis(diphenyl-1-yl) vinyl-1-yl, a stilbenyl group, a styrenyl group and the like, but are not limited thereto.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, specific examples of the phosphine oxide group may include a diphenylphosphine oxide group, a dinaphthylphosphine oxide group and the like, but are not limited thereto.

In the present specification, the amine group may be selected from the group consisting of —NH$_2$; a monoalkylamine group; a dialkylamine group; an N-alkylarylamine group; a monoarylamine group; a diarylamine group; an N-arylheteroarylamine group; an N-alkylheteroarylamine group, a monoheteroarylamine group and a diheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group, an N-phenylnaphthylamine group, an N-naphthylfluorenylamine N-biphenylnaphthylamine group, an group, an N-phenylphenanthrenylamine group, an N-biphenylphenanthrenylamine group, an N-phenylfluorenylamine group, an N-phenylterphenylamine group, an N-phenanthrenylfluorenylamine group, an N-biphenylfluorenylamine group and the like, but are not limited thereto.

When the aryl group is a monocyclic aryl group in the present specification, the number of carbon atoms is not particularly limited, but is preferably from 6 to 25. Specific examples of the monocyclic aryl group may include a phenyl group, a biphenyl group, a terphenyl group, a quaterphenyl group and the like, but are not limited thereto.

When the aryl group is a polycyclic aryl group, the number of carbon atoms is not particularly limited, but is preferably from 10 to 30. Specific examples of the polycyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and adjacent substituents may bond to each other to form a ring.

When the fluorenyl group is substituted,

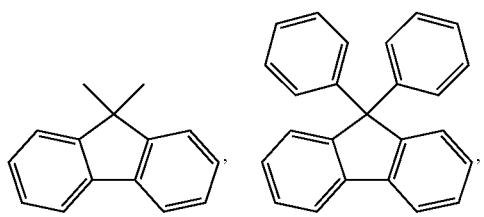

-continued

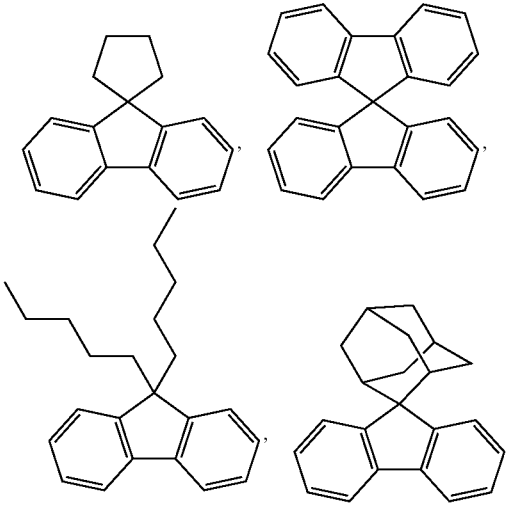

and the like may be included. However, the structure is not limited thereto.

The aryl group may be substituted with an alkyl group to function as an arylalkyl group. The alkyl group may be selected from among the examples described above.

In the present specification, the heterocyclic group is a group including one or more atoms that are not carbon, that is, heteroatoms, and specifically, the heteroatom may include one or more atoms selected from the group consisting of O, N, Se, S and the like. The number of carbon atoms is not particularly limited, but is preferably from 2 to 30, and the heterocyclic group may be monocyclic or polycyclic. Examples of the heterocyclic group may include a thiophene group, a furan group, a pyrrole group, an imidazole group, a thiazole group, an oxazole group, an oxadiazole group, a pyridine group, a pyrimidine group, a triazine group, a triazole group, a quinolinyl group, a quinazoline group, a carbazole group, a benzoxazole group, a benzimidazole group, a benzothiazole group, a benzocarbazole group, a benzothiophene group, a dibenzothiophene group, a benzofuran group, a phenanthroline group, an isoxazole group, a thiadiazole group, a dibenzofuran group and the like, but are not limited thereto.

In the present specification, the arylene group means an aryl group having two bonding sites, that is, a divalent group. Descriptions on the aryl group provided above may be applied thereto except for those that are each divalent.

In one embodiment of the present specification, the compound represented by Chemical Formula 1 is 1% to 100% deuterated. The term "deuterated" is intended to mean at least one available H being replaced by D. In the X % deuterated compound or group, X % of available H is replaced by D. In the deuterated compound or group, deuterium is present in at least 100 times the natural abundance level.

In one embodiment of the present specification, the compound represented by Chemical Formula 1 is 1% to 100% deuterated.

In one embodiment of the present specification, the compound represented by Chemical Formula 1 is 50% to 100% deuterated.

In one embodiment of the present specification, R1 and R2 are a linear or branched alkyl group having 1 to 10 carbon atoms; or an aryl group having 6 to 10 carbon atoms, or bond to each other to form a cycloalkyl group having 4 to 8 carbon atoms.

In one embodiment of the present specification, R1 and R2 are a methyl group; an ethyl group; or a phenyl group, or bond to each other to form a cyclobutyl group; a cyclopentyl group; or a cyclohexyl group.

In one embodiment of the present specification, when n is 1, -Ar1, -Ar2-E1, -Ar3 and -Ar4-E2 are the same as each other.

In one embodiment of the present specification, when n is 1, E1 and E2 are hydrogen.

In one embodiment of the present specification, n is an integer of 2 to 30,000.

In one embodiment of the present specification, at least one of L1 to L6 and Ar1 to Ar4 is substituted with a linear or branched alkyl group having 1 to 10 carbon atoms; or an adamantyl group.

In one embodiment of the present specification, at least one of L1 to L6 and Ar1 to Ar4 is substituted with a methyl group; an ethyl group; a butyl group; a propyl group; a pentyl group; a hexyl group; or an adamantyl group.

In one embodiment of the present specification, at least one of L1 to L6 and Ar1 to Ar4 is substituted with a methyl group; an ethyl group; a butyl group; a propyl group; a pentyl group; a hexyl group; or an adamantyl group.

In one embodiment of the present specification, when n is 1, Ar1 and Ar3 are a phenyl group substituted with an alkyl group or an alkenyl group; or a substituted or unsubstituted polycyclic aryl group, and Ar2 and Ar4 are a phenylene group substituted with an alkyl group or an alkenyl group; or a substituted or unsubstituted polycyclic arylene group.

In one embodiment of the present specification, when n is 1, Ar1 and Ar3 are a phenyl group unsubstituted or substituted with an alkyl group or an alkenyl group; a substituted or unsubstituted biphenyl group; a substituted or unsubstituted terphenyl group; a substituted or unsubstituted naphthyl group; or a substituted or unsubstituted fluorene group, and Ar2 and Ar4 are a phenylene group unsubstituted or substituted with an alkyl group or an alkenyl group; a substituted or unsubstituted biphenylylene group; a substituted or unsubstituted divalent terphenyl group; a substituted or unsubstituted divalent naphthyl group; or a substituted or unsubstituted divalent fluorene group.

The compound of Chemical Formula 1 according to the present specification is a material for a solution process, and when n is 1, the structure in the molecule may be shifted when introducing a carbon chain structure having an end group being an alkyl group or an alkenyl group such as Ar1 to Ar4 to the compound, and solubility increases therefrom. Accordingly, the solution process is more readily conducted, and film properties are enhanced since there are interactions in the molecular arrangements after forming a film through the solution process.

In one embodiment of the present specification, Ar1 and Ar3 are a substituted or unsubstituted phenyl group; a substituted or unsubstituted biphenyl group; a substituted or unsubstituted terphenyl group; a substituted or unsubstituted naphthyl group; or a substituted or unsubstituted fluorene group.

In one embodiment of the present specification, Ar1 and Ar3 are a phenyl group unsubstituted or substituted with an alkyl group or an alkenyl group; a biphenyl group unsubstituted or substituted with an alkyl group or an alkenyl group; a terphenyl group unsubstituted or substituted with an alkyl group or an alkenyl group; a naphthyl group unsubstituted or substituted with an alkyl group or an alkenyl group; or a fluorene group unsubstituted or substituted with an alkyl group, a cycloalkyl group or an adamantyl group.

In one embodiment of the present specification, Ar1 and Ar3 are a phenyl group unsubstituted or substituted with an alkyl group having 1 to 20 carbon atoms or a vinyl group; a biphenyl group unsubstituted or substituted with an alkyl group having 1 to 20 carbon atoms or a vinyl group; a terphenyl group unsubstituted or substituted with an alkyl group having 1 to 20 carbon atoms or a vinyl group; a naphthyl group unsubstituted or substituted with an alkyl group having 1 to 20 carbon atoms or a vinyl group; or a fluorene group unsubstituted or substituted with an alkyl group having 1 to 20 carbon atoms, a cycloalkyl group having 4 to 20 carbon atoms or an adamantyl group.

In one embodiment of the present specification, Ar1 and Ar3 are a phenyl group unsubstituted or substituted with an alkyl group having 1 to 10 carbon atoms or a vinyl group; a biphenyl group unsubstituted or substituted with an alkyl group having 1 to 10 carbon atoms or a vinyl group; a terphenyl group unsubstituted or substituted with an alkyl group having 1 to 10 carbon atoms or a vinyl group; a naphthyl group unsubstituted or substituted with an alkyl group having 1 to 10 carbon atoms or a vinyl group; or a fluorene group unsubstituted or substituted with an alkyl group having 1 to 10 carbon atoms, a cycloalkyl group having 4 to 10 carbon atoms or an adamantyl group.

In one embodiment of the present specification, Ar1 and Ar3 are a phenyl group unsubstituted or substituted with an alkyl group having 1 to 6 carbon atoms or a vinyl group; a biphenyl group unsubstituted or substituted with an alkyl group having 1 to 6 carbon atoms or a vinyl group; a terphenyl group unsubstituted or substituted with an alkyl group having 1 to 6 carbon atoms or a vinyl group; a naphthyl group unsubstituted or substituted with an alkyl group having 1 to 6 carbon atoms or a vinyl group; or a fluorene group unsubstituted or substituted with an alkyl group having 1 to 6 carbon atoms, a cycloalkyl group having 4 to 8 carbon atoms or an adamantyl group.

In one embodiment of the present specification, Ar2 and Ar4 are a substituted or unsubstituted phenylene group; a substituted or unsubstituted biphenylylene group; a substituted or unsubstituted terphenylylene group; a substituted or unsubstituted naphthylene group; or a substituted or unsubstituted divalent fluorene group.

In one embodiment of the present specification, Ar2 and Ar4 are a phenylene group unsubstituted or substituted with an alkyl group or an alkenyl group; a biphenylylene group unsubstituted or substituted with an alkyl group or an alkenyl group; a terphenylylene group unsubstituted or substituted with an alkyl group or an alkenyl group; a naphthylene group unsubstituted or substituted with an alkyl group or an alkenyl group; or a divalent fluorene group unsubstituted or substituted with an alkyl group, a cycloalkyl group or an adamantyl group.

In one embodiment of the present specification, Ar2 and Ar4 are a phenylene group unsubstituted or substituted with an alkyl group having 1 to 20 carbon atoms or a vinyl group; a biphenylylene group unsubstituted or substituted with an alkyl group having 1 to 20 carbon atoms or a vinyl group; a terphenylylene group unsubstituted or substituted with an alkyl group having 1 to 20 carbon atoms or a vinyl group; a naphthylene group unsubstituted or substituted with an alkyl group having 1 to 20 carbon atoms or a vinyl group; or a divalent fluorene group unsubstituted or substituted with an alkyl group having 1 to 20 carbon atoms, a cycloalkyl group having 4 to 20 carbon atoms or an adamantyl group.

In one embodiment of the present specification, Ar2 and Ar4 are a phenylene group unsubstituted or substituted with an alkyl group having 1 to 10 carbon atoms or a vinyl group; a biphenylylene group unsubstituted or substituted with an alkyl group having 1 to 10 carbon atoms or a vinyl group; a terphenylylene group unsubstituted or substituted with an alkyl group having 1 to 10 carbon atoms or a vinyl group; a naphthylene group unsubstituted or substituted with an alkyl group having 1 to 10 carbon atoms or a vinyl group; or a divalent fluorene group unsubstituted or substituted with an alkyl group having 1 to 10 carbon atoms, a cycloalkyl group having 4 to 10 carbon atoms or an adamantyl group.

In one embodiment of the present specification, Ar2 and Ar4 are a phenylene group unsubstituted or substituted with an alkyl group having 1 to 6 carbon atoms or a vinyl group; a biphenylylene group unsubstituted or substituted with an alkyl group having 1 to 6 carbon atoms or a vinyl group; a terphenylylene group unsubstituted or substituted with an alkyl group having 1 to 6 carbon atoms or a vinyl group; a naphthylene group unsubstituted or substituted with an alkyl group having 1 to 6 carbon atoms or a vinyl group; or a divalent fluorene group unsubstituted or substituted with an alkyl group having 1 to 6 carbon atoms, a cycloalkyl group having 4 to 8 carbon atoms or an adamantyl group.

In one embodiment of the present specification, L1, L3 and L4 are the same as or different from each other, and are each independently a substituted or unsubstituted phenylene group; a substituted or unsubstituted biphenylylene group; a substituted or unsubstituted terphenylylene group; a substituted or unsubstituted naphthylene group; or a substituted or unsubstituted divalent fluorene group.

In one embodiment of the present specification, L1, L3 and L4 are a phenylene group unsubstituted or substituted with an alkyl group or an alkenyl group; a biphenylylene group unsubstituted or substituted with an alkyl group or an alkenyl group; a terphenylylene group unsubstituted or substituted with an alkyl group or an alkenyl group; a naphthylene group unsubstituted or substituted with an alkyl group or an alkenyl group; or a divalent fluorene group unsubstituted or substituted with an alkyl group, a cycloalkyl group or an adamantyl group.

In one embodiment of the present specification, L1, L3 and L4 are a phenylene group unsubstituted or substituted with an alkyl group having 1 to 20 carbon atoms or a vinyl group; a biphenylylene group unsubstituted or substituted with an alkyl group having 1 to 20 carbon atoms or a vinyl group; a terphenylylene group unsubstituted or substituted with an alkyl group having 1 to 20 carbon atoms or a vinyl group; a naphthylene group unsubstituted or substituted with an alkyl group having 1 to 20 carbon atoms or a vinyl group; or a divalent fluorene group unsubstituted or substituted with an alkyl group having 1 to 20 carbon atoms, a cycloalkyl group having 4 to 20 carbon atoms or an adamantyl group.

In one embodiment of the present specification, L1, L3 and L4 are a phenylene group unsubstituted or substituted with an alkyl group having 1 to 10 carbon atoms or a vinyl group; a biphenylylene group unsubstituted or substituted with an alkyl group having 1 to 10 carbon atoms or a vinyl group; a terphenylylene group unsubstituted or substituted with an alkyl group having 1 to 10 carbon atoms or a vinyl group; a naphthylene group unsubstituted or substituted with an alkyl group having 1 to 10 carbon atoms or a vinyl group; or a divalent fluorene group unsubstituted or substituted with an alkyl group having 1 to 10 carbon atoms, a cycloalkyl group having 4 to 10 carbon atoms or an adamantyl group.

In one embodiment of the present specification, L1, L3 and L4 are a phenylene group unsubstituted or substituted with an alkyl group having 1 to 6 carbon atoms or a vinyl group; a biphenylylene group unsubstituted or substituted with an alkyl group having 1 to 6 carbon atoms or a vinyl group; a terphenylylene group unsubstituted or substituted with an alkyl group having 1 to 6 carbon atoms or a vinyl group; a naphthylene group unsubstituted or substituted with an alkyl group having 1 to 6 carbon atoms or a vinyl group; or a divalent fluorene group unsubstituted or substituted with an alkyl group having 1 to 6 carbon atoms, a cycloalkyl group having 4 to 8 carbon atoms or an adamantyl group.

In one embodiment of the present specification, L2, L5 and L6 have the same definitions as L1, L3 and L4.

In one embodiment of the present specification, a and b are 0.

In one embodiment of the present specification, a and b are 1.

In one embodiment of the present specification, a and b are 2.

In one embodiment of the present specification, c and e are 0.

In one embodiment of the present specification, c and e are 1.

In one embodiment of the present specification, c and e are 2.

In one embodiment of the present specification, d and f are 0.

In one embodiment of the present specification, d and f are 1.

In one embodiment of the present specification, d and f are 2.

In one embodiment of the present specification, a to f being each 0 means linking groups in the parentheses being a direct bond.

In one embodiment of the present specification, the compound represented by Chemical Formula 1 is any one of the following structural formulae.

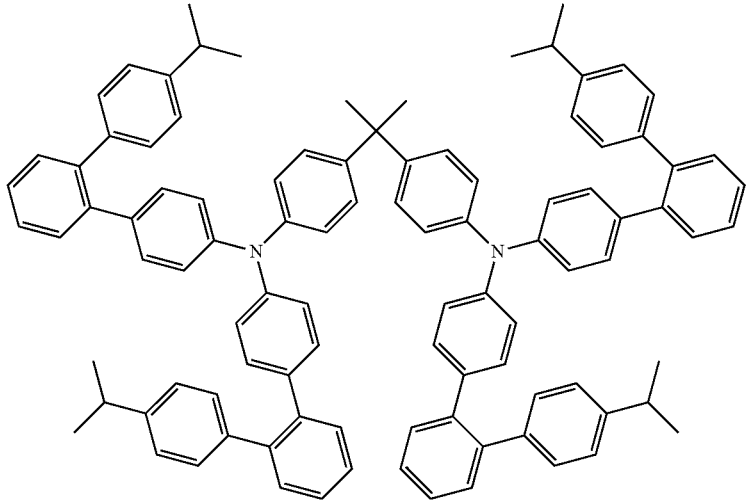

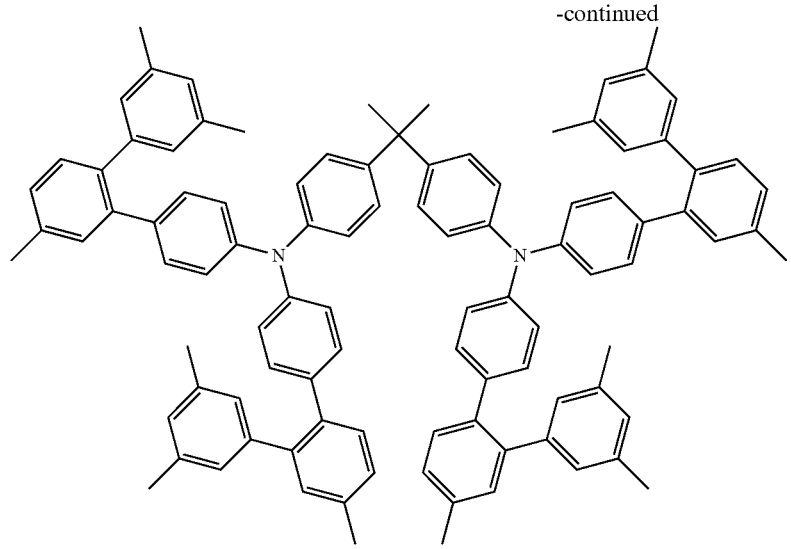
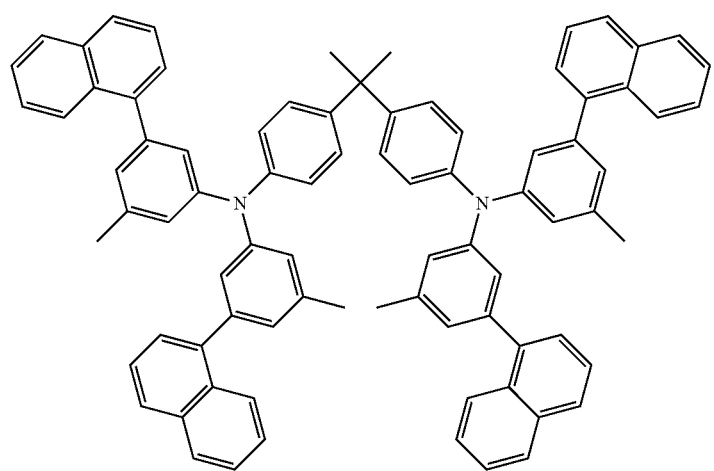
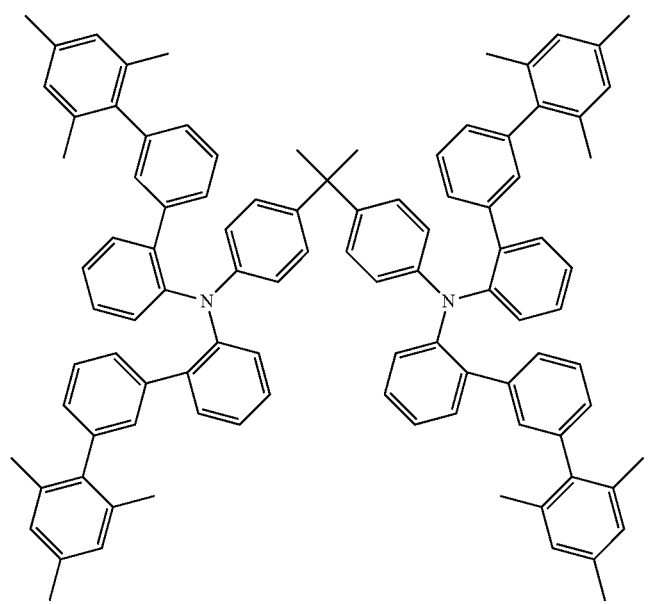

-continued
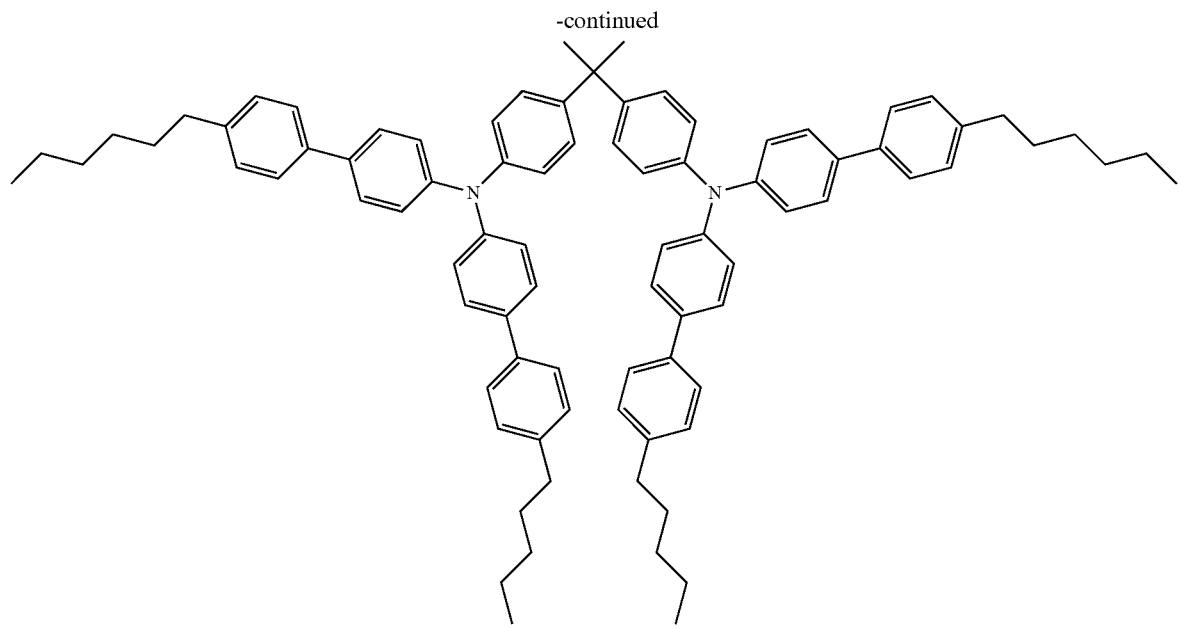
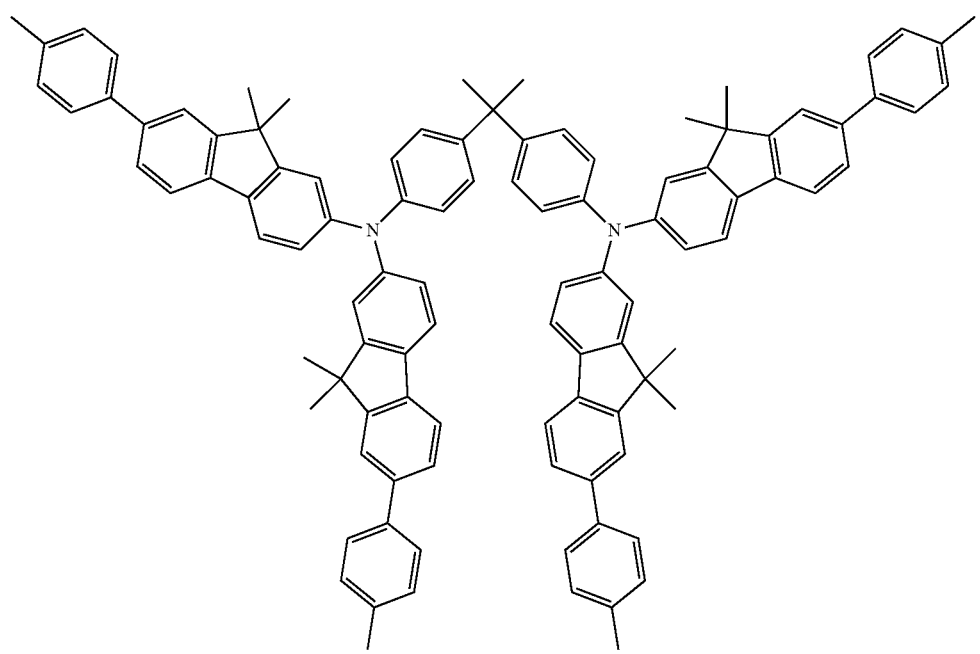
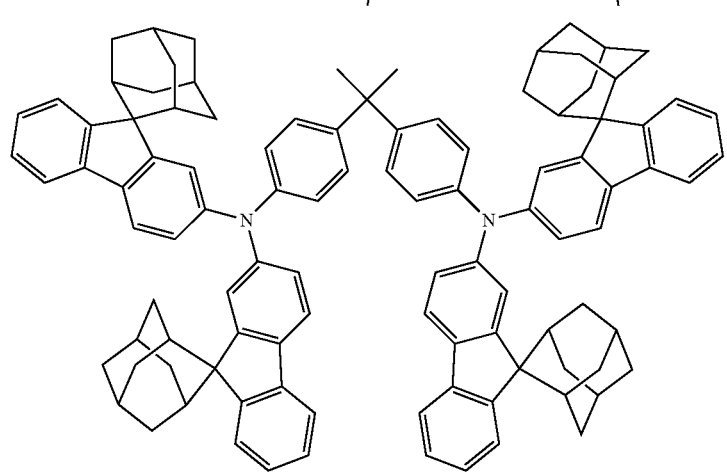

-continued
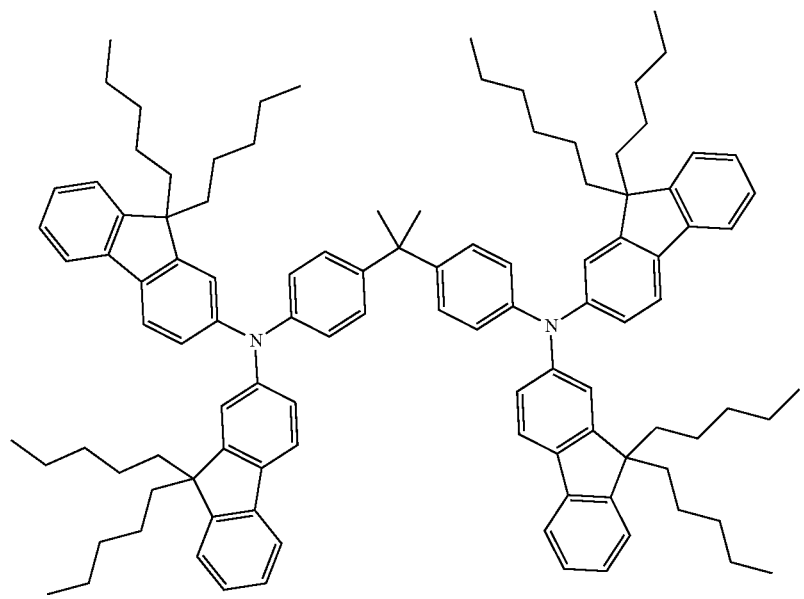
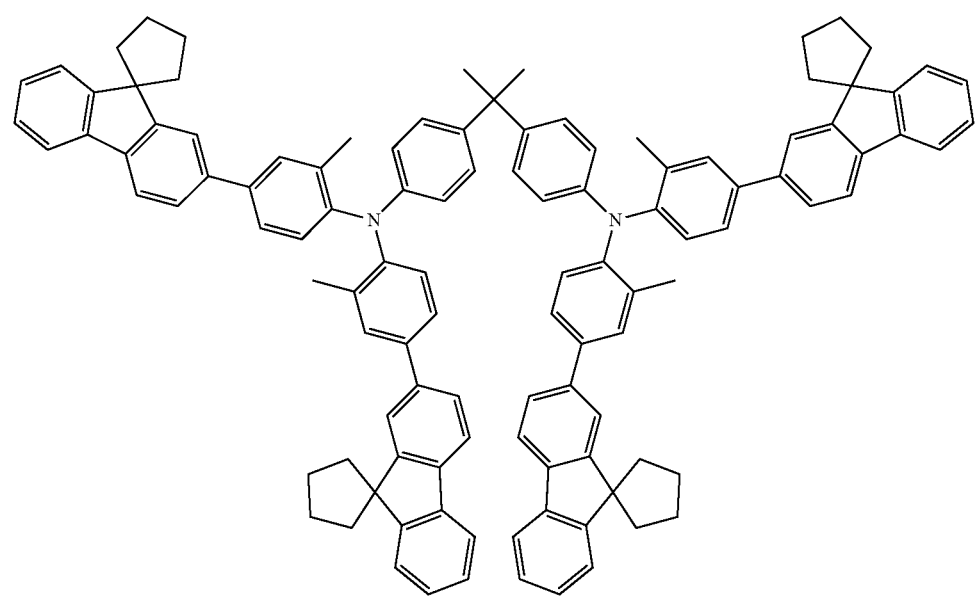

-continued
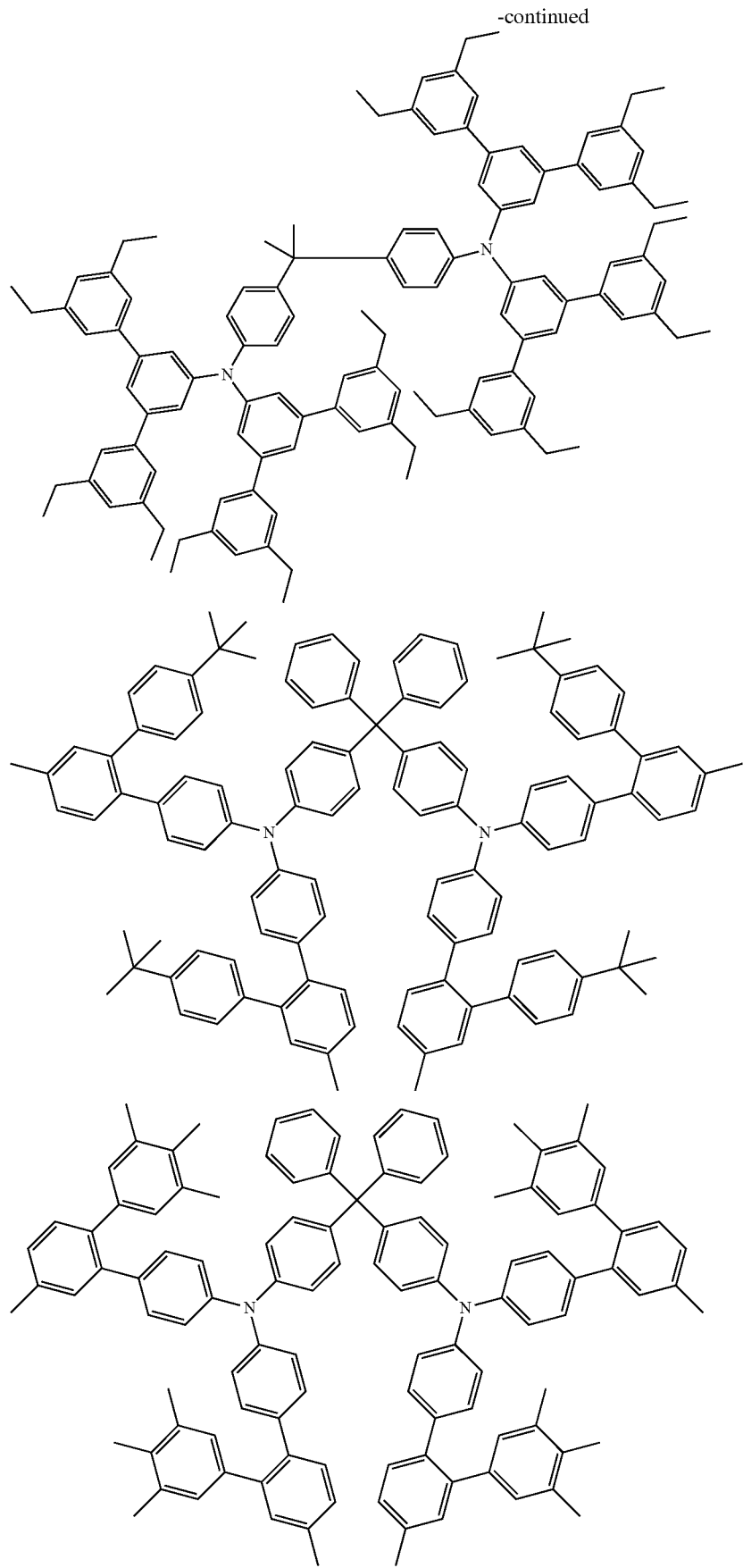

-continued
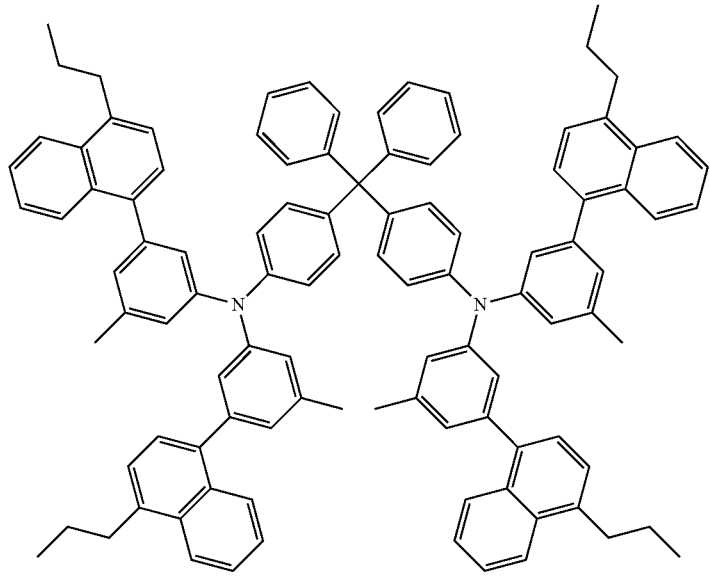
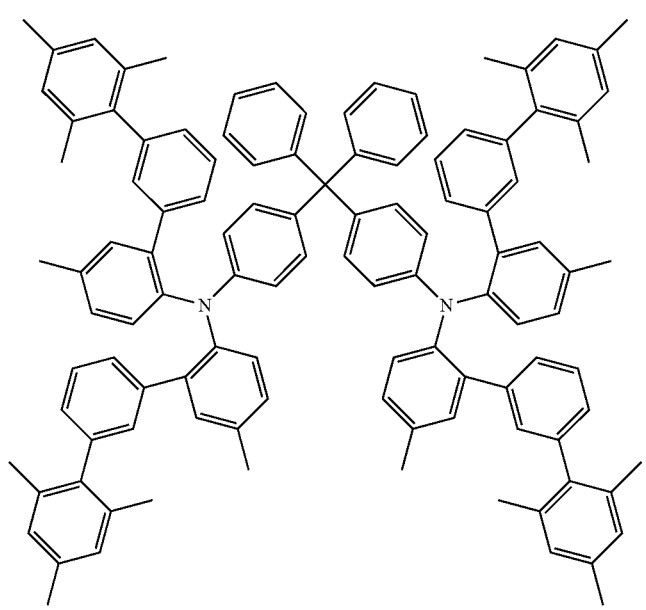

-continued
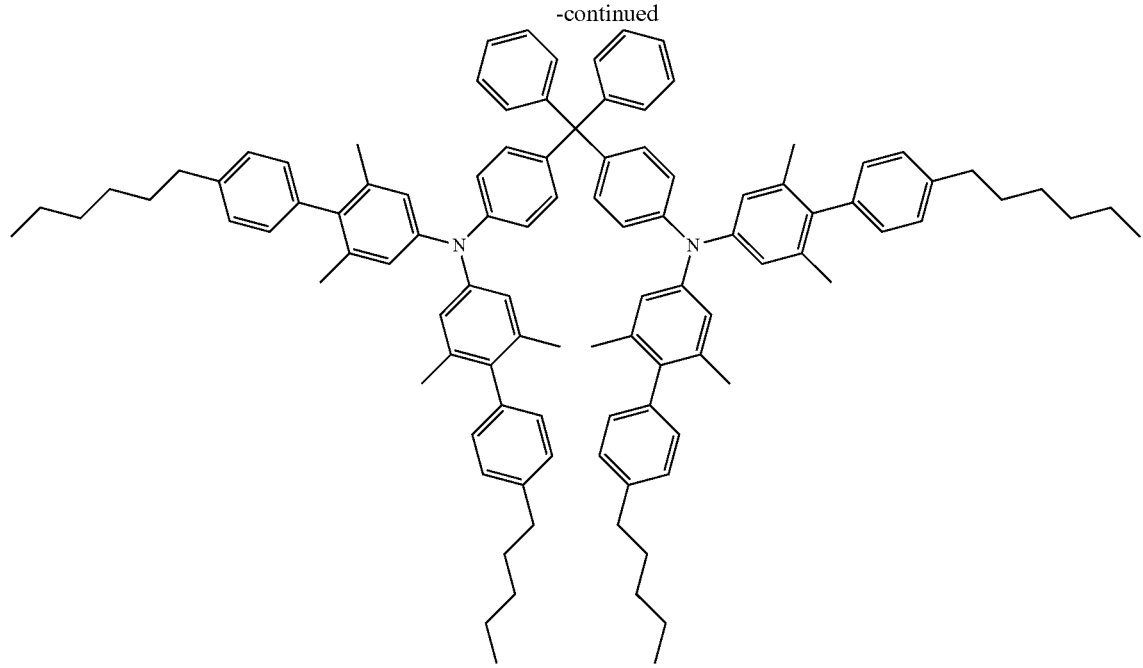
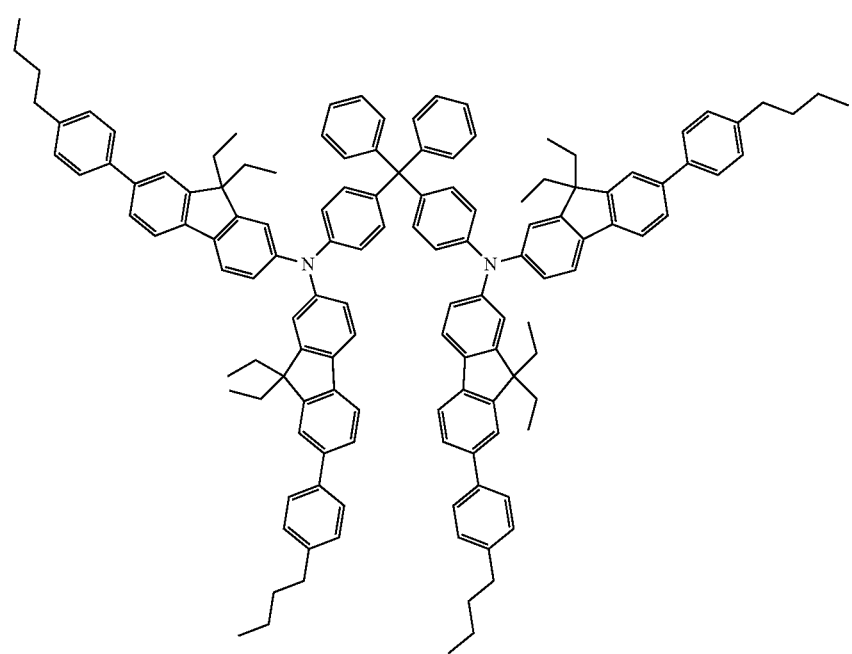

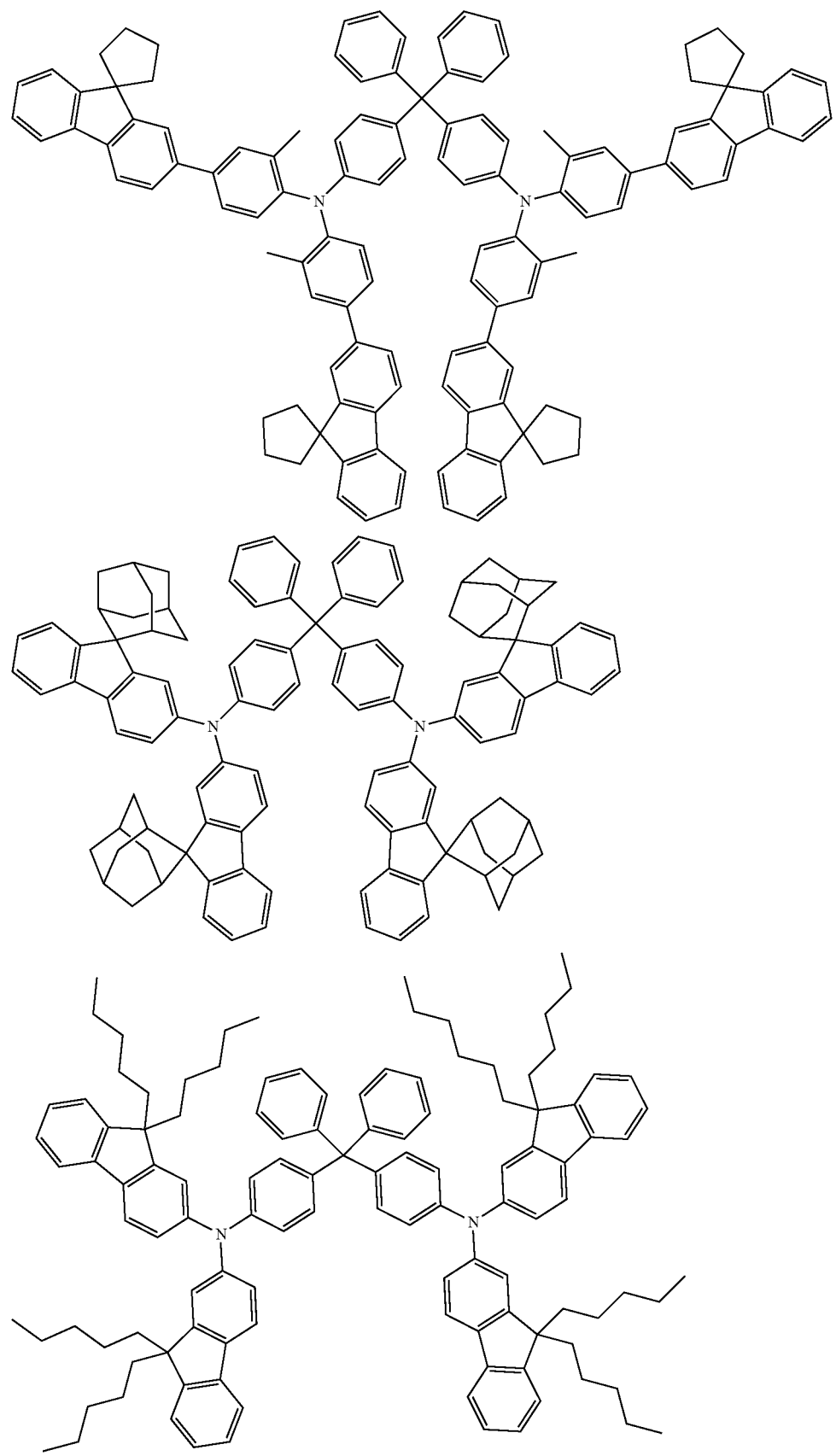

-continued
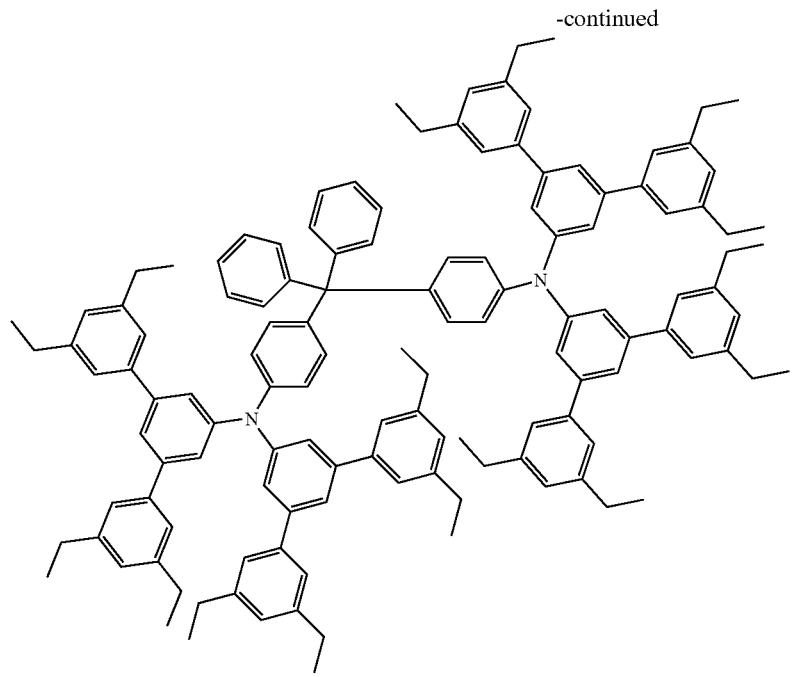
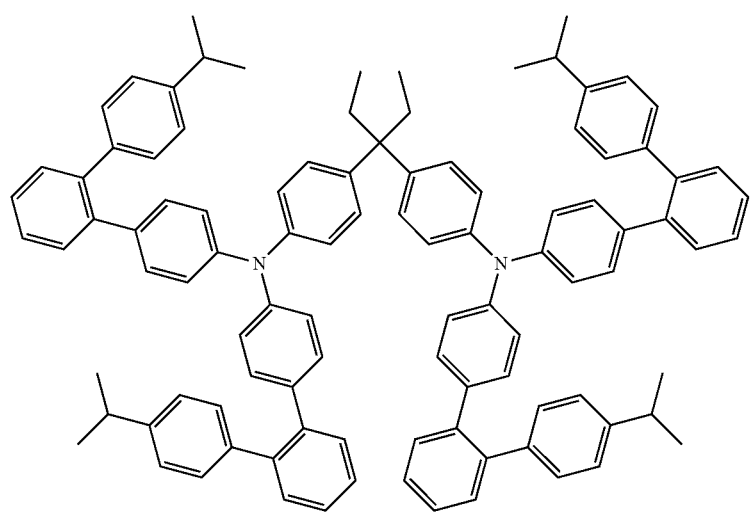
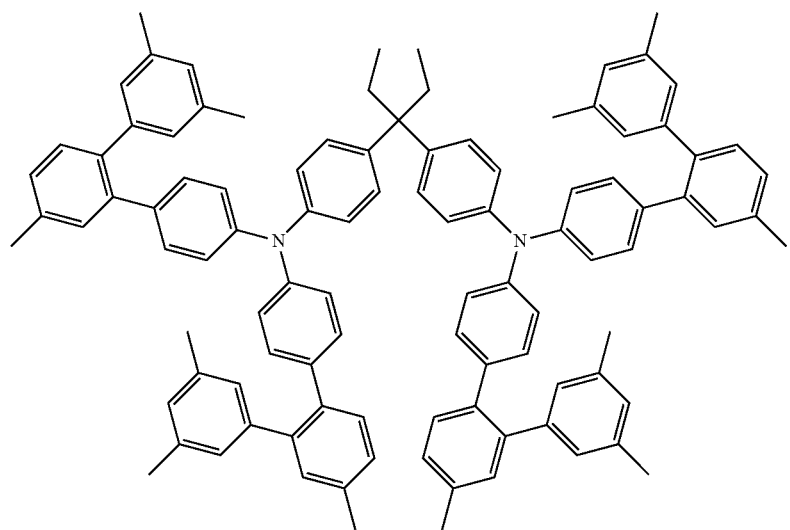

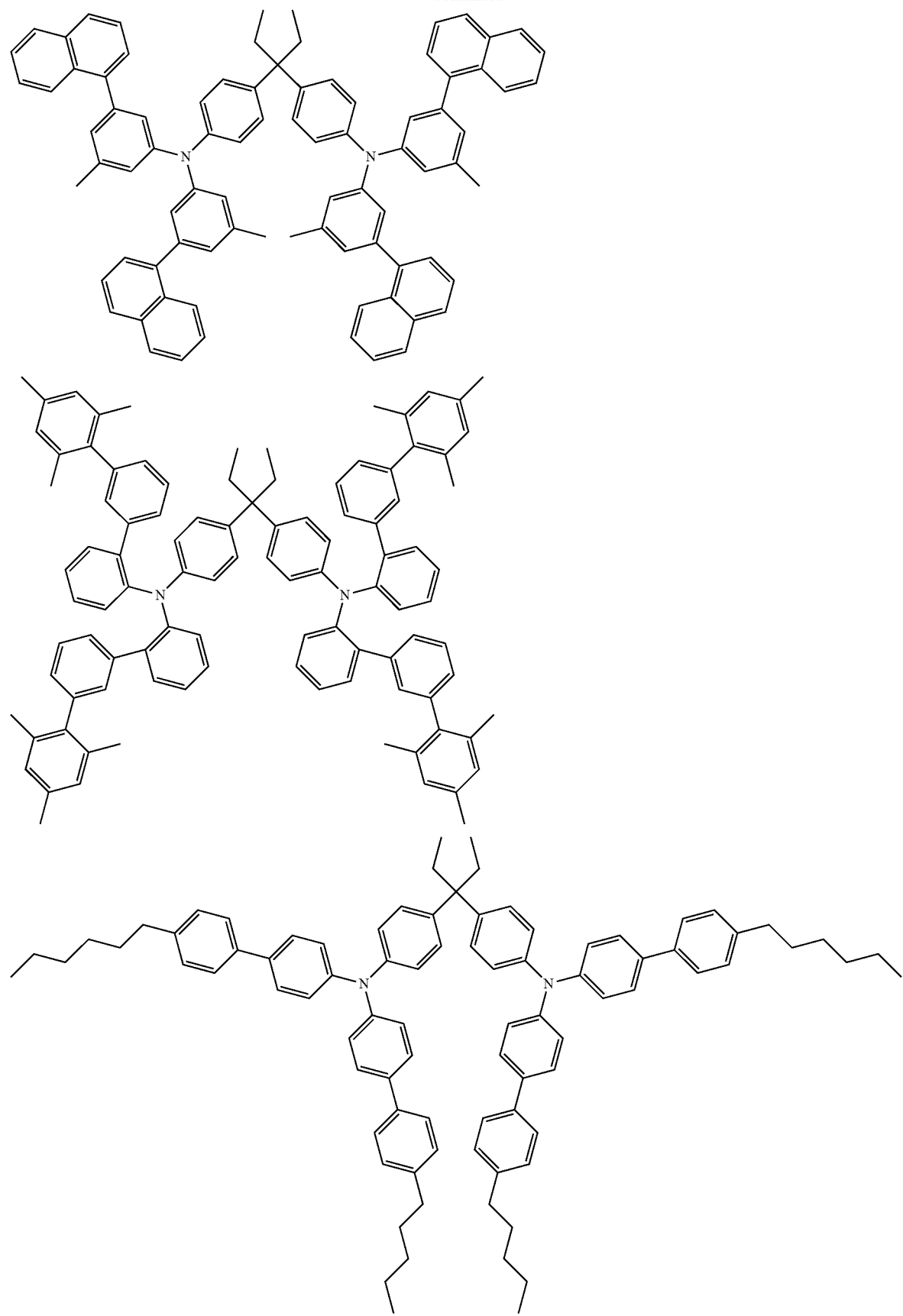

-continued
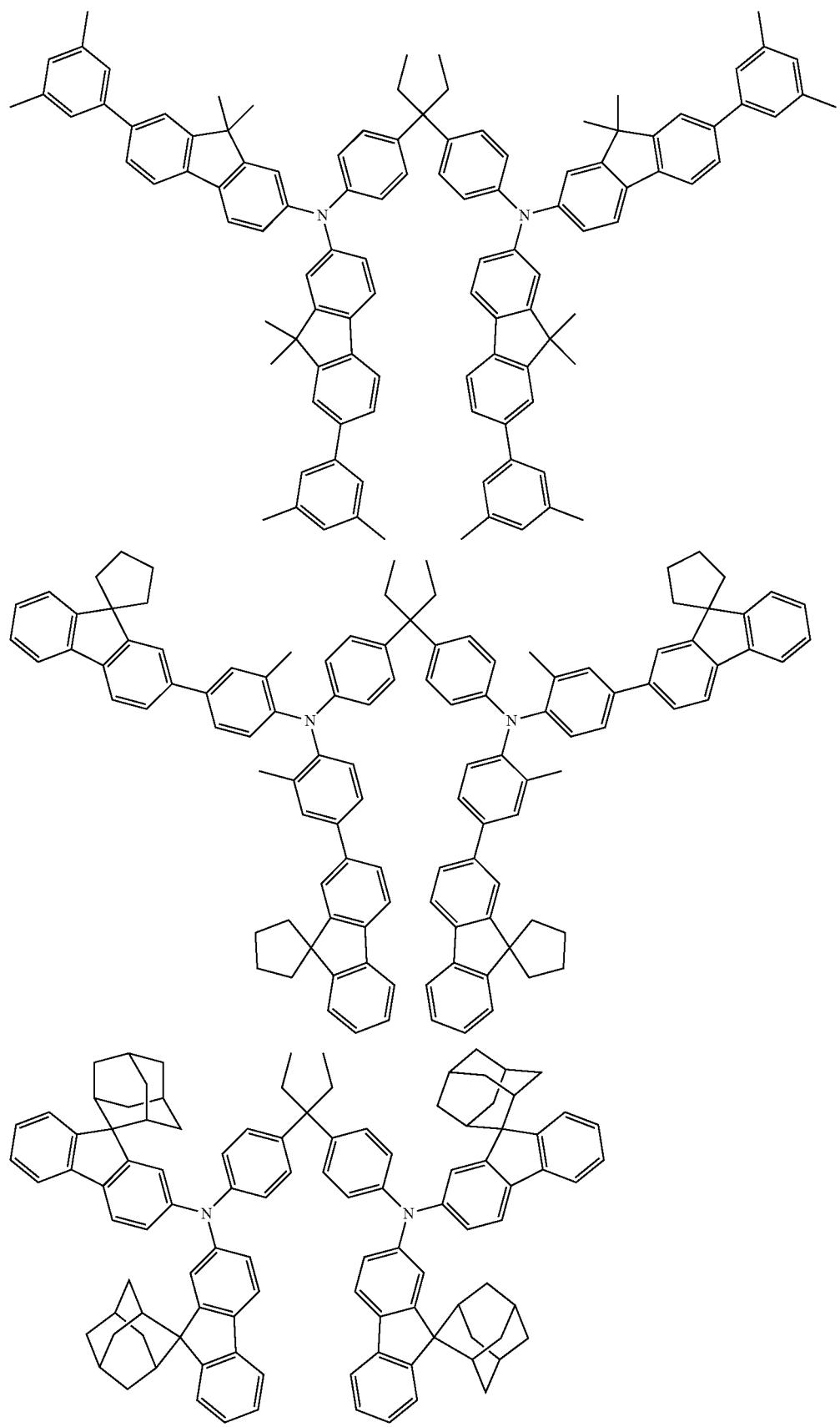

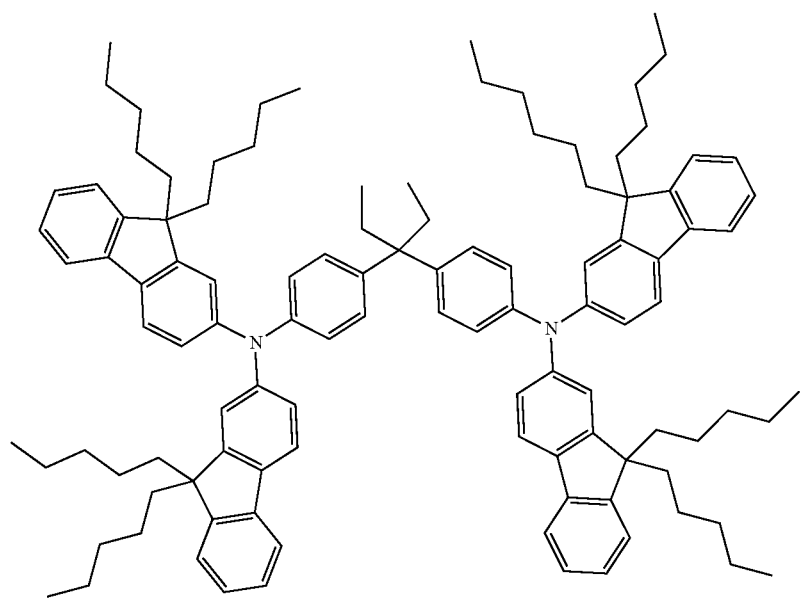
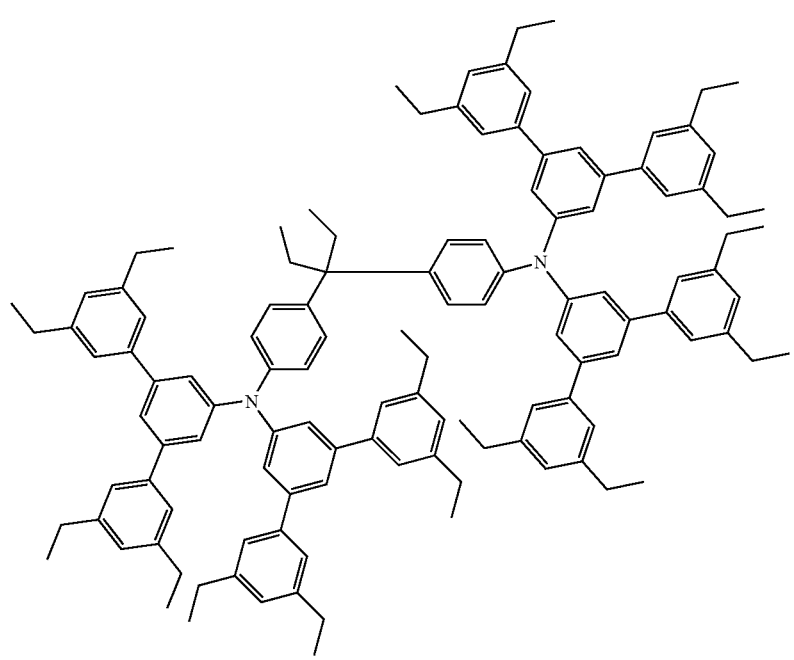

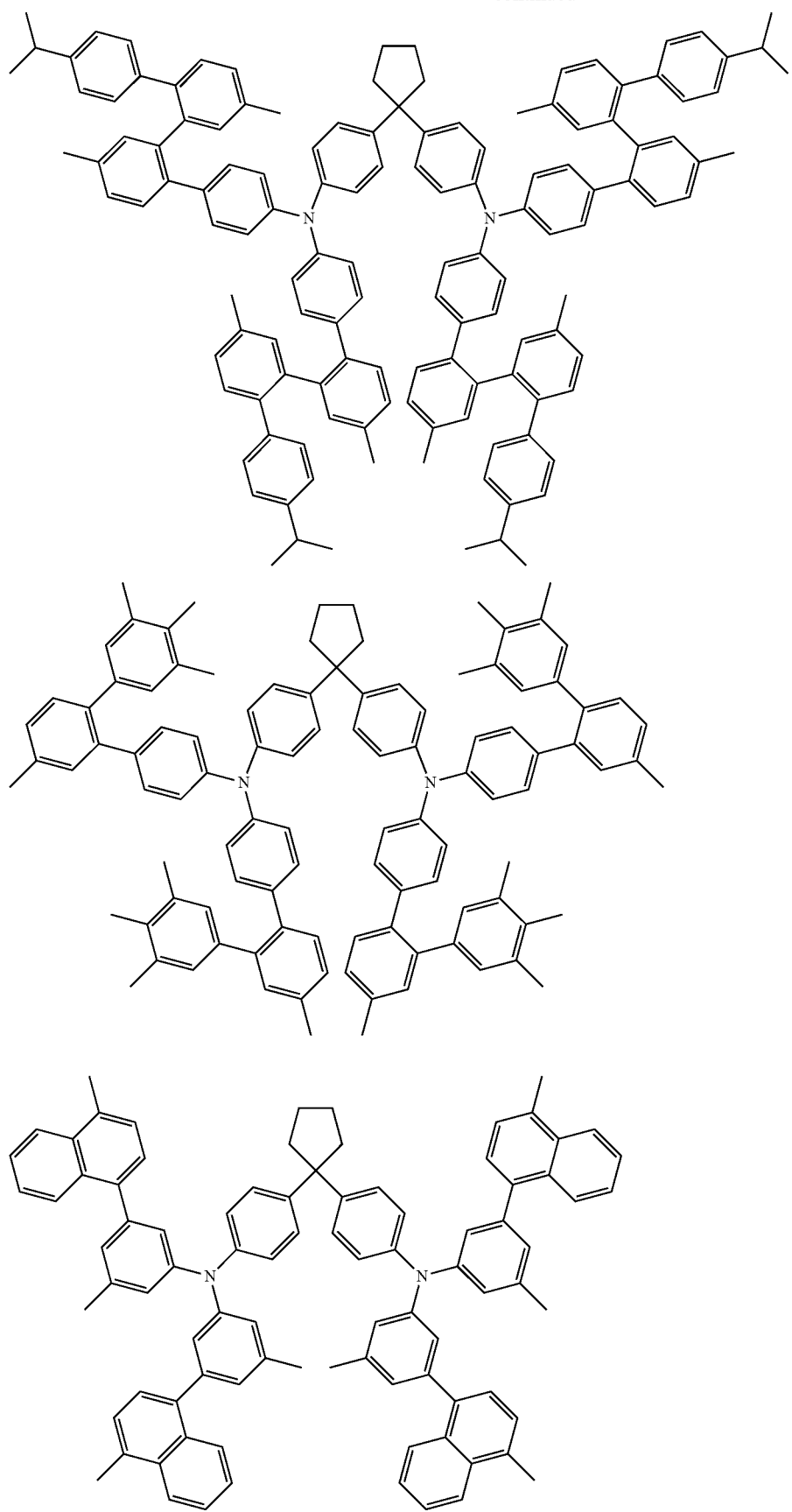

-continued
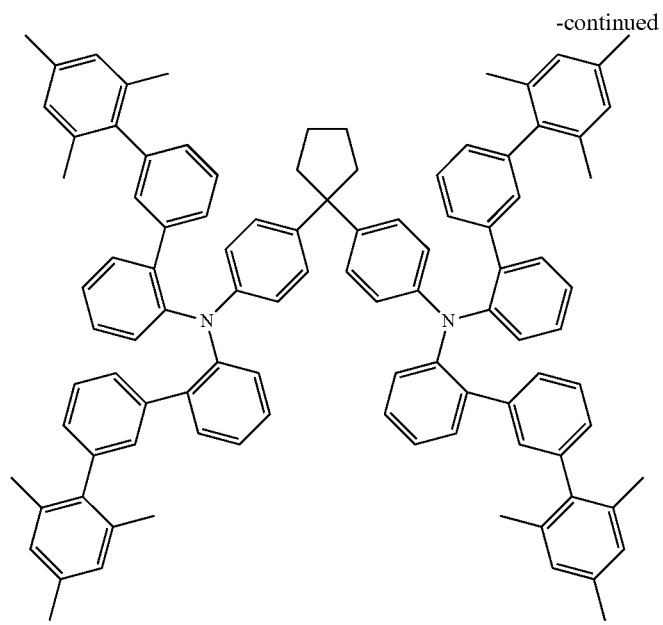
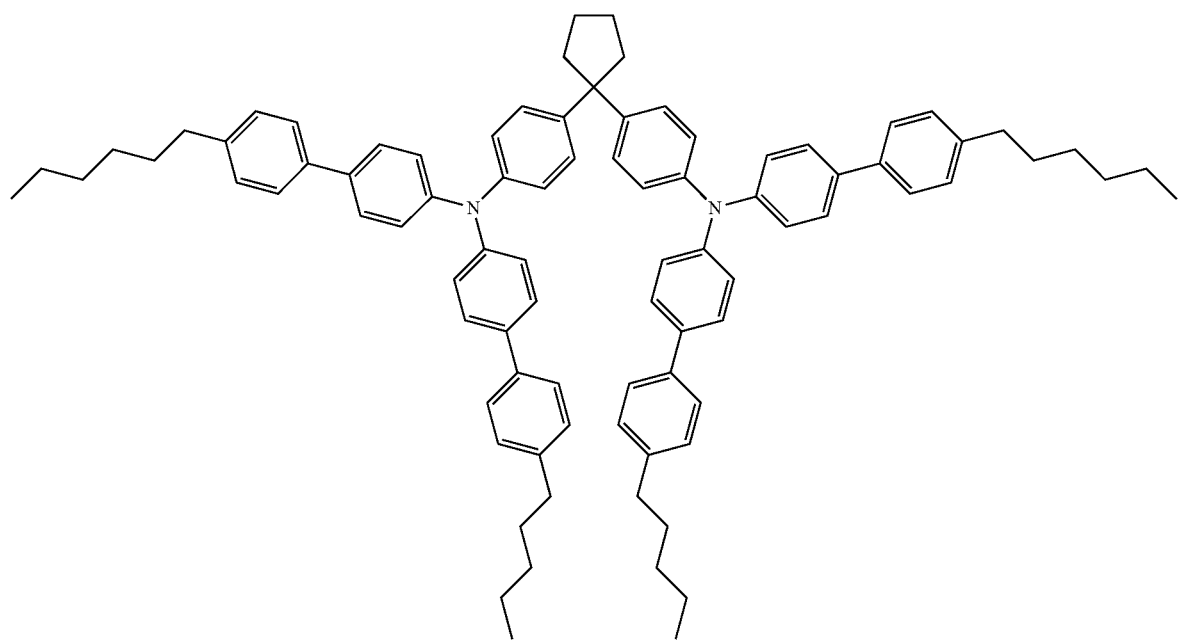

-continued
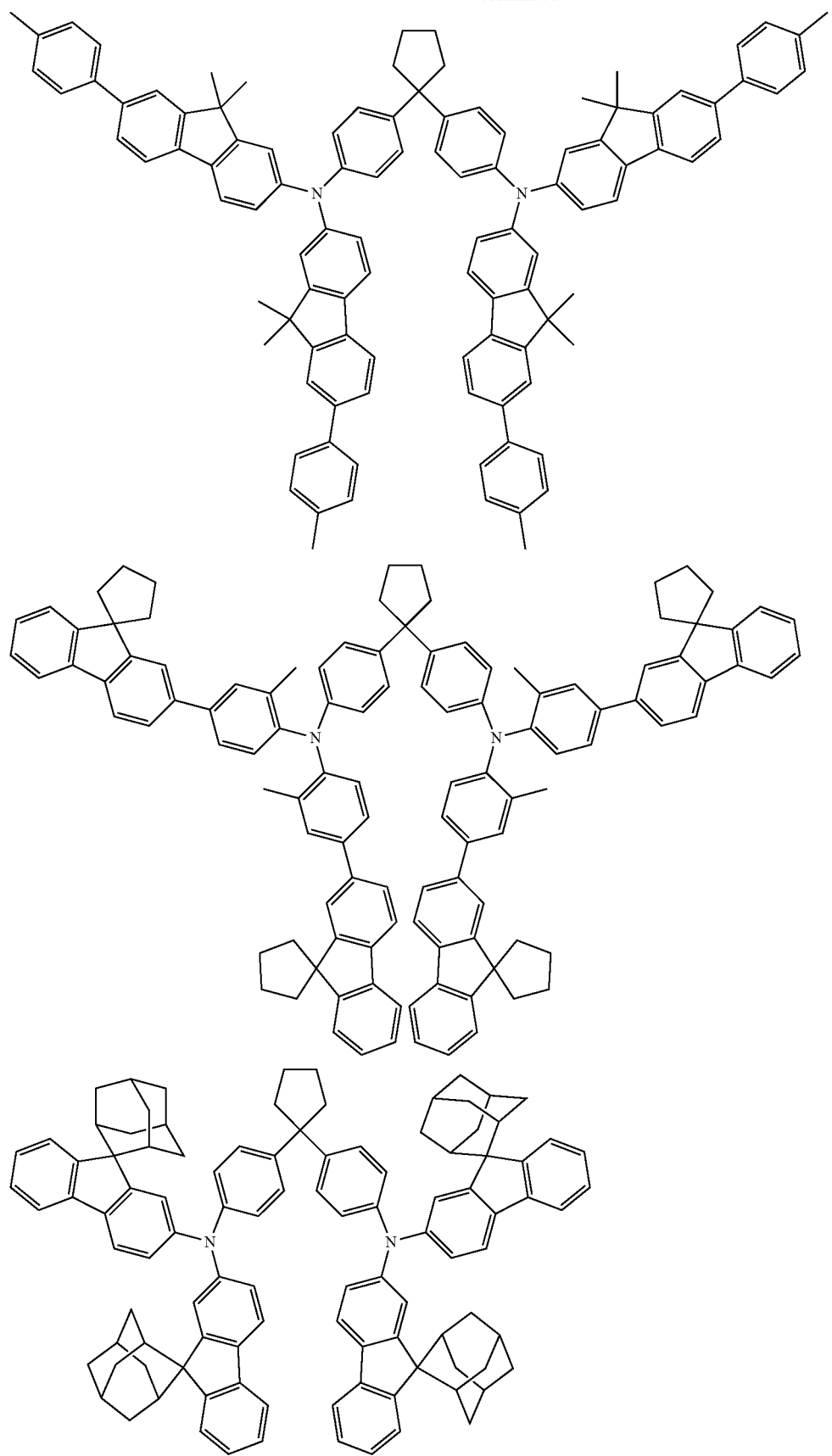

-continued
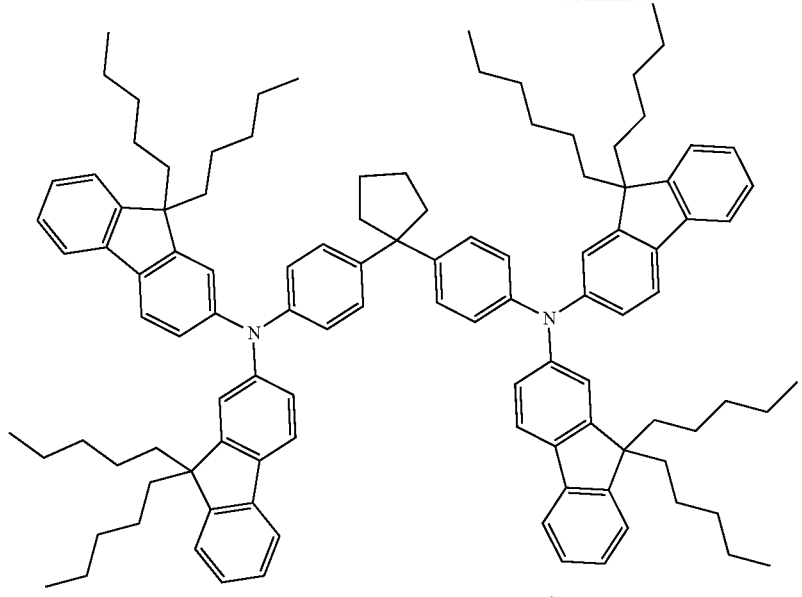
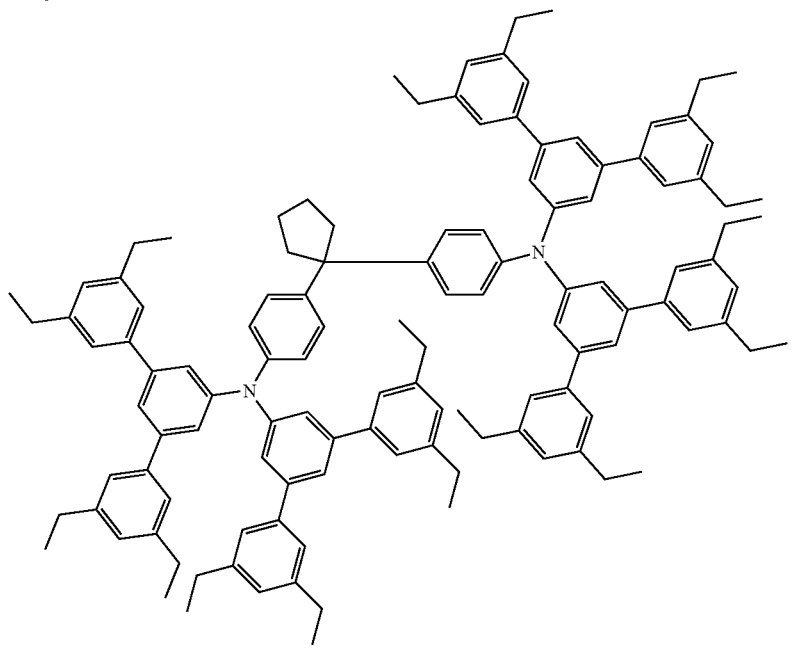
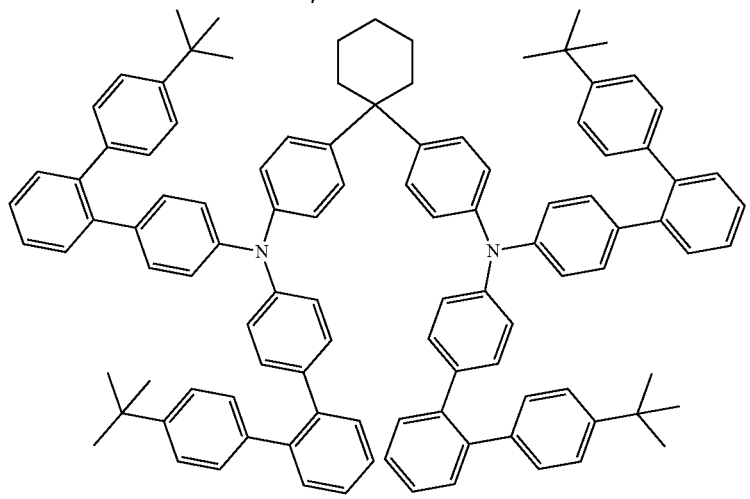

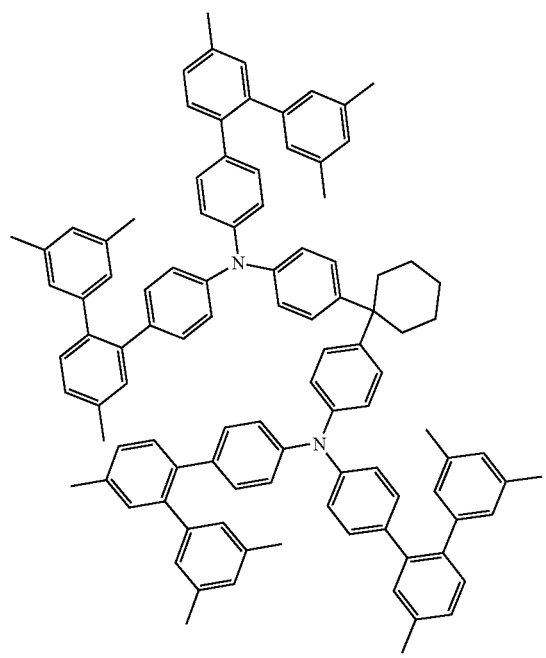
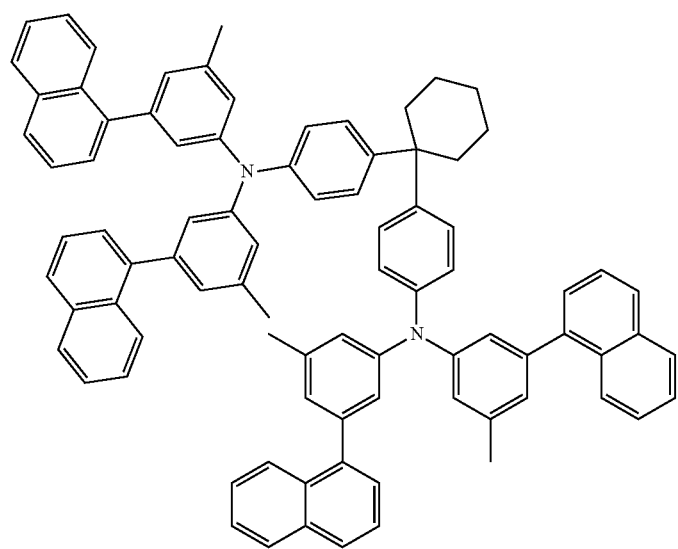

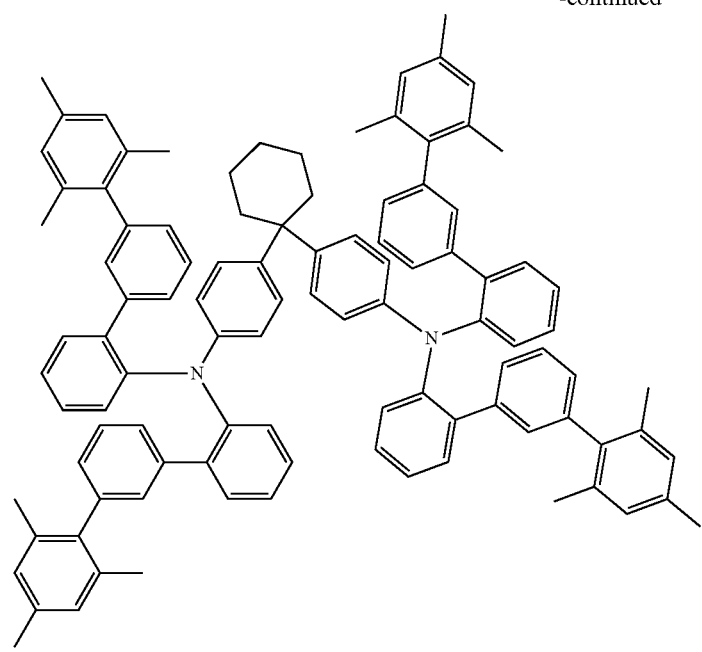
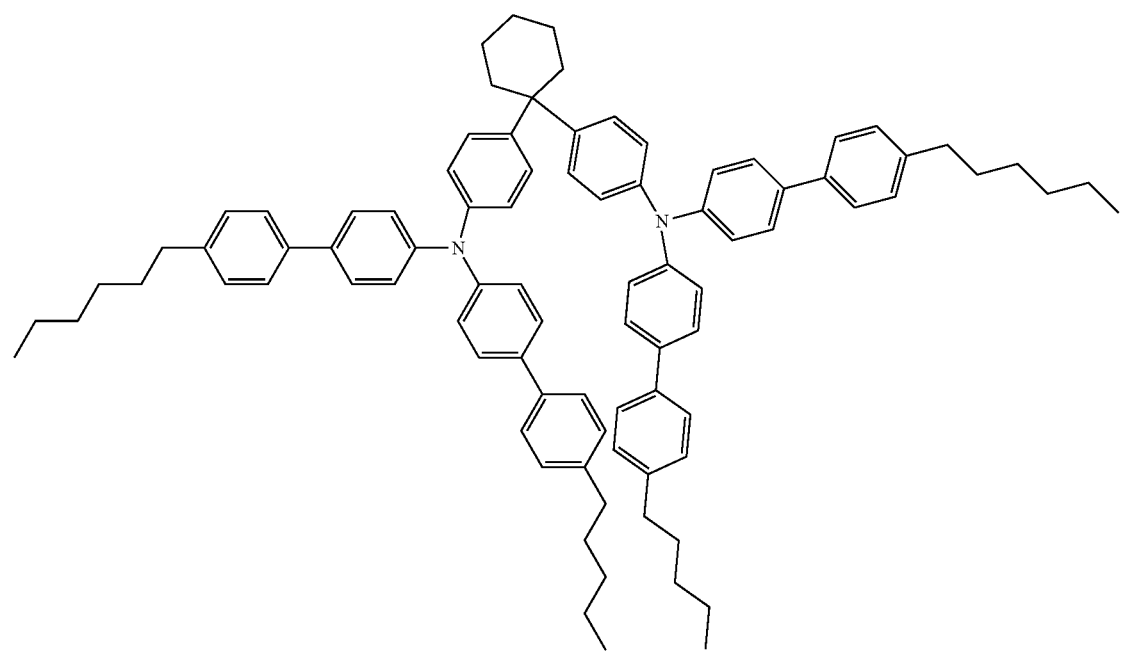

-continued
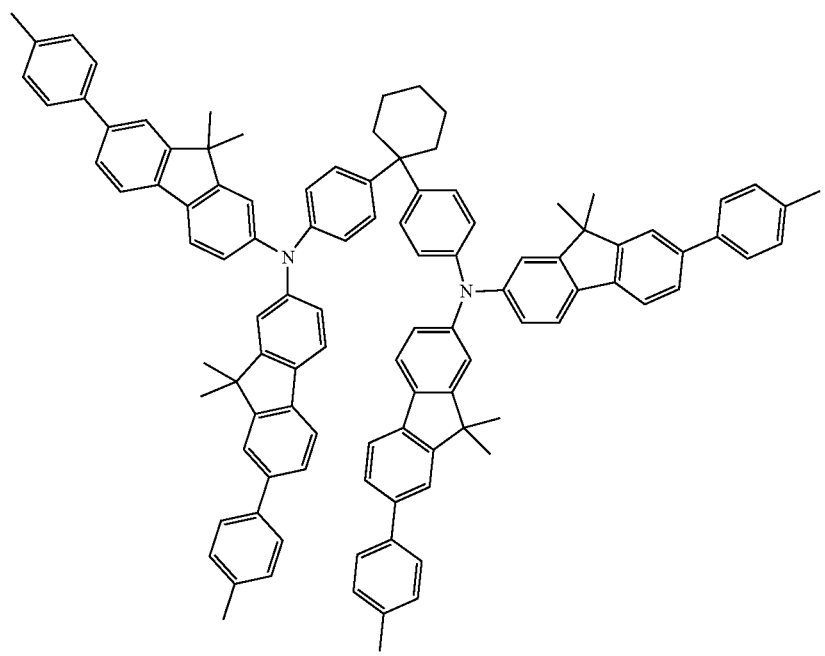
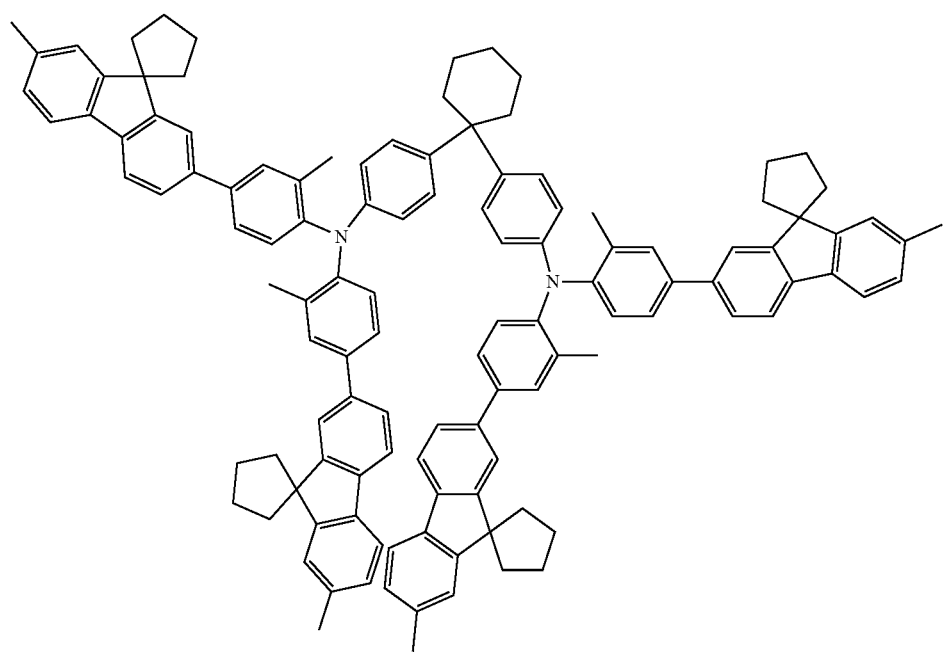

-continued
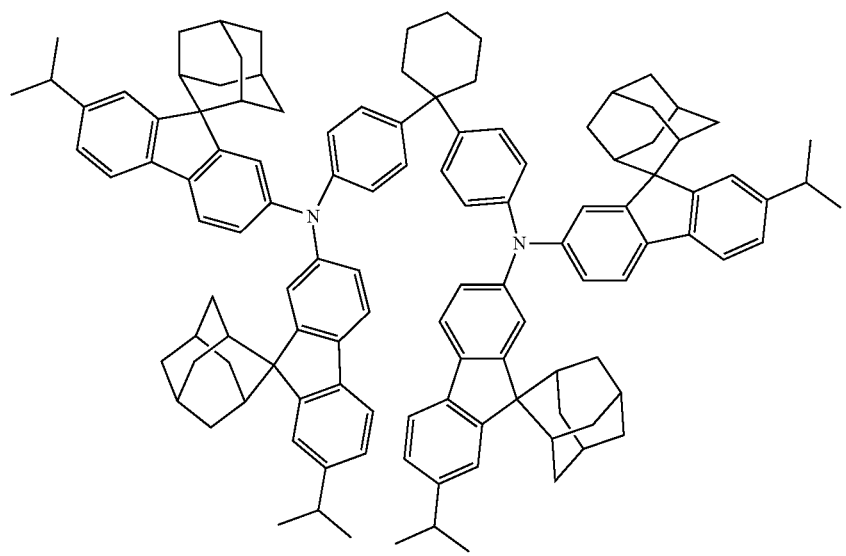
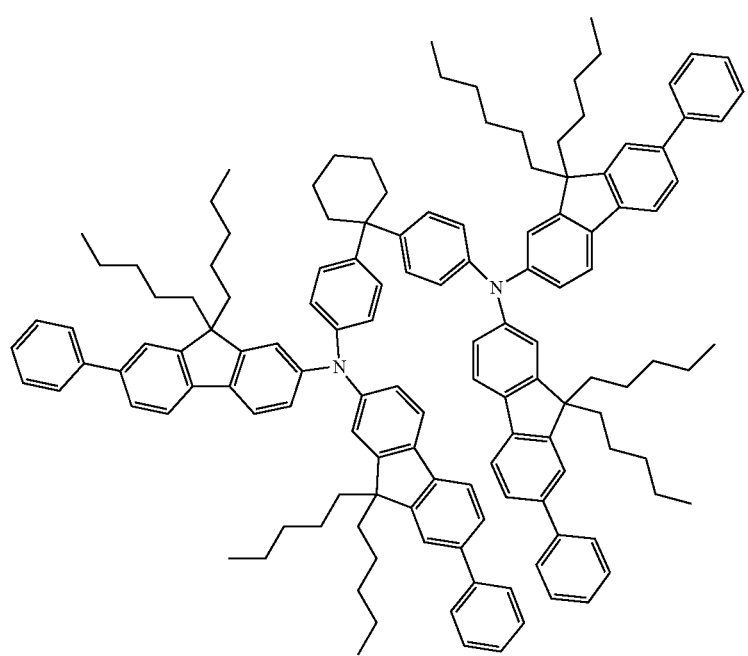

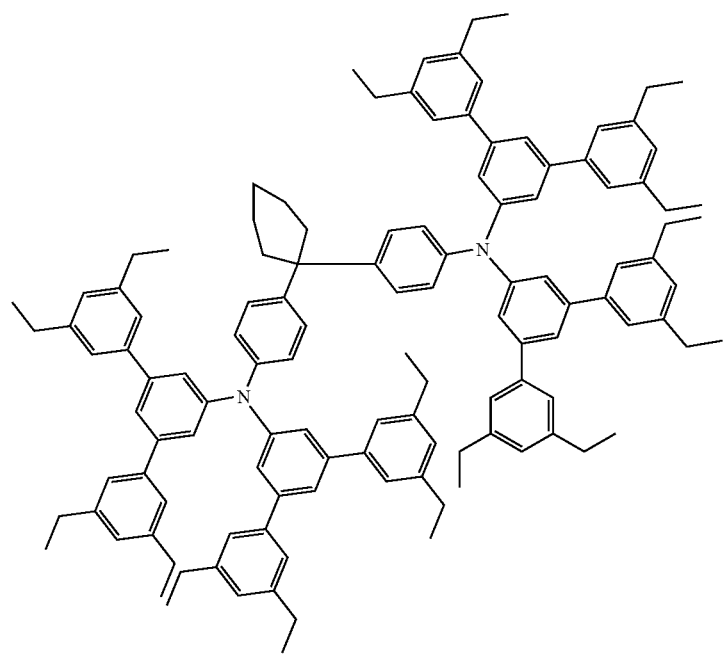
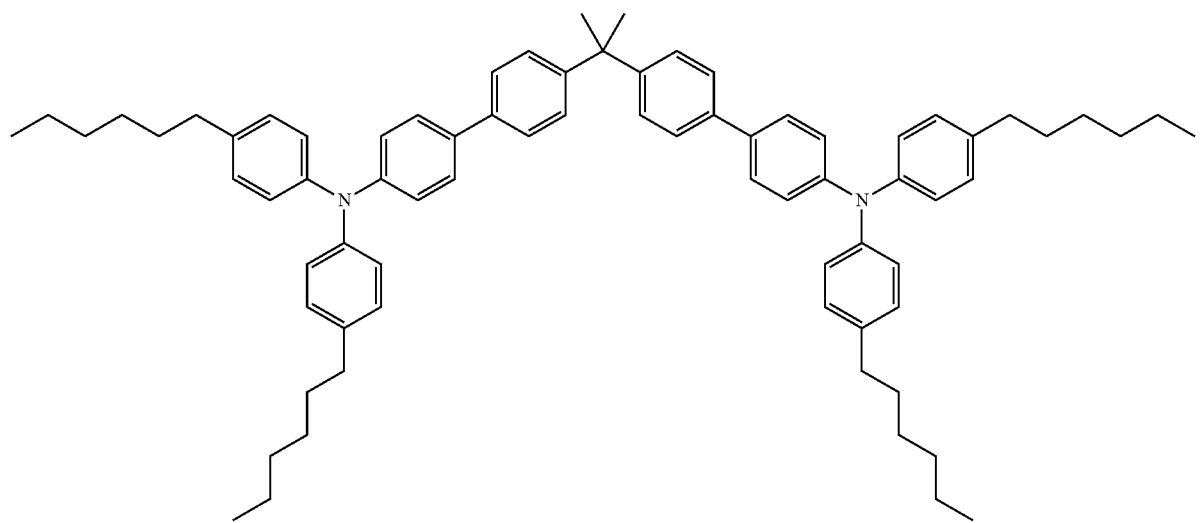

-continued
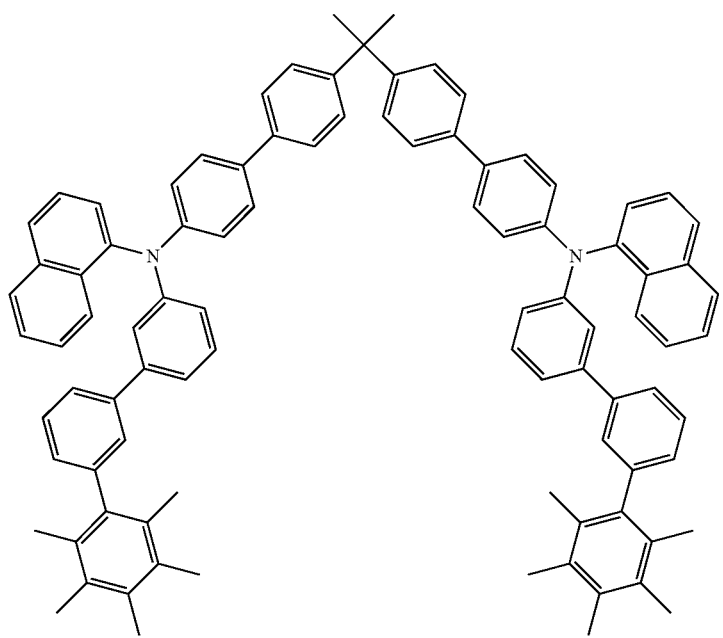
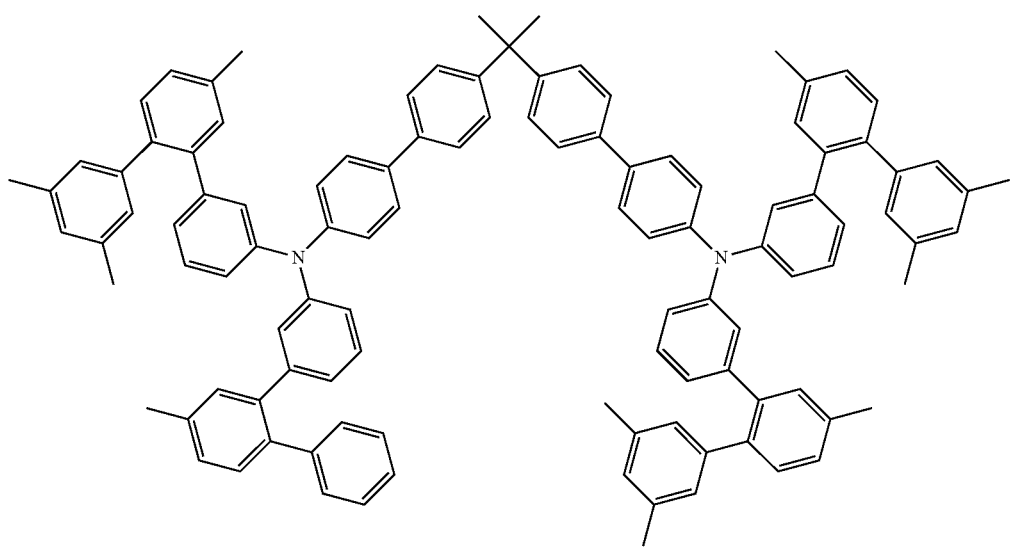

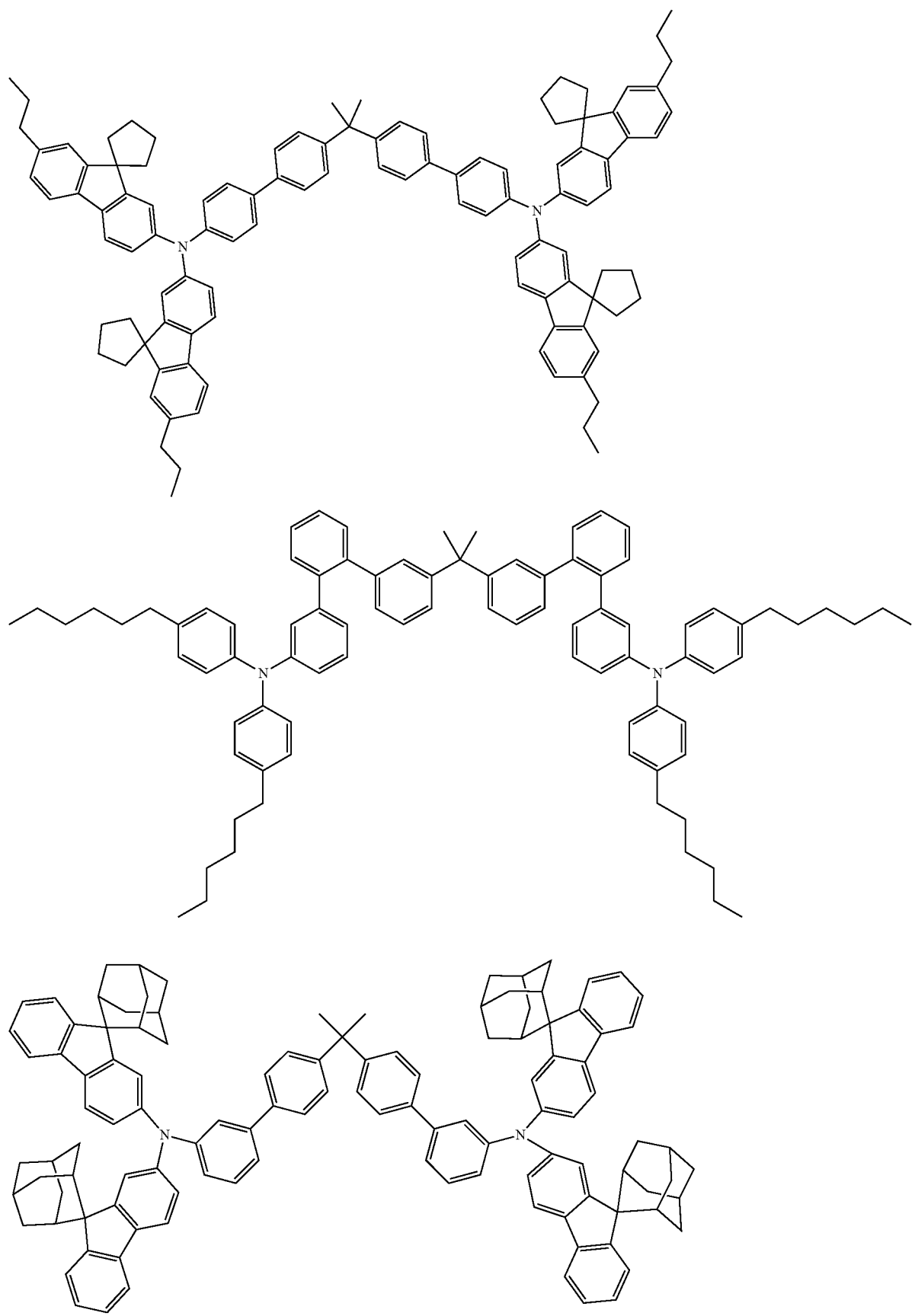

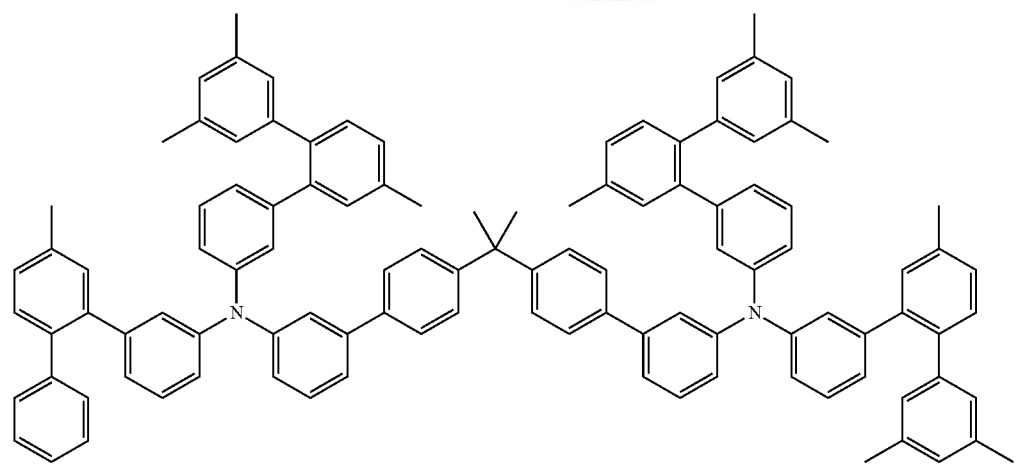
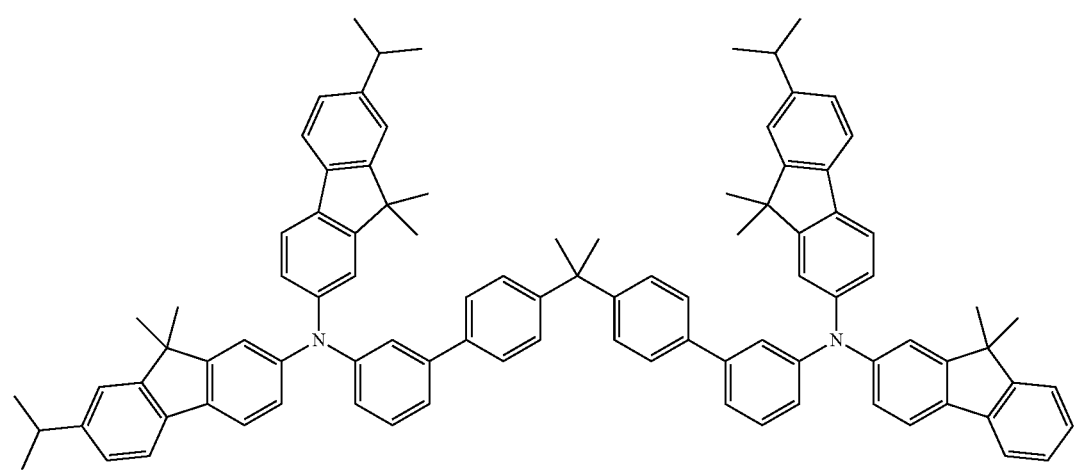
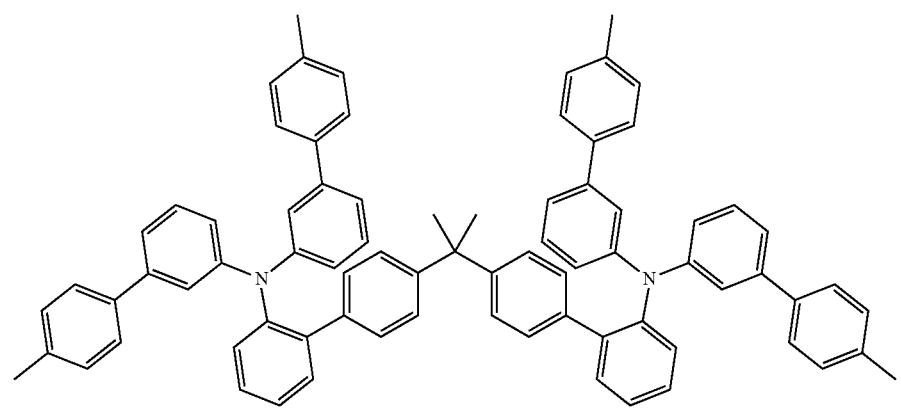

-continued
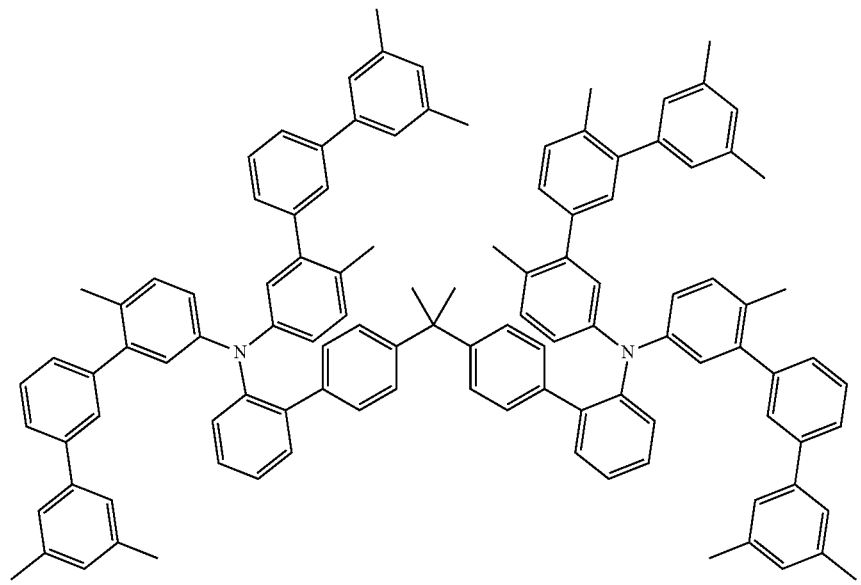
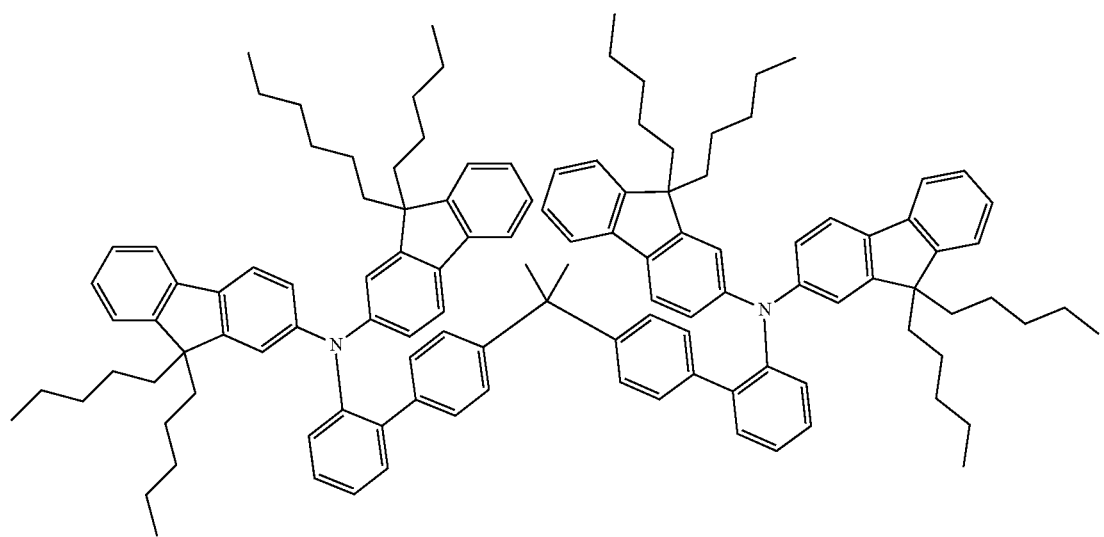

-continued
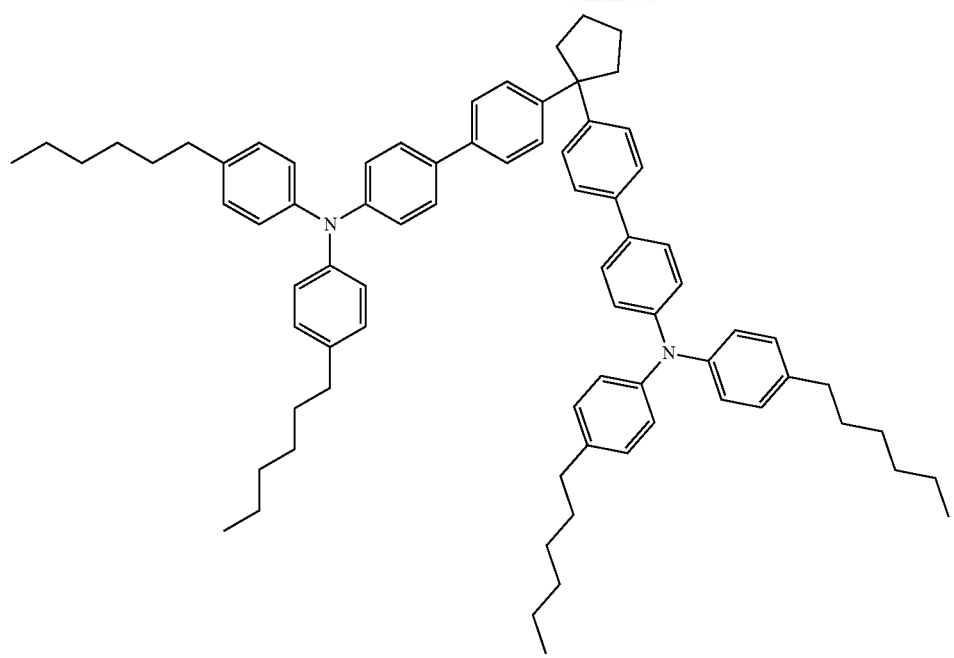
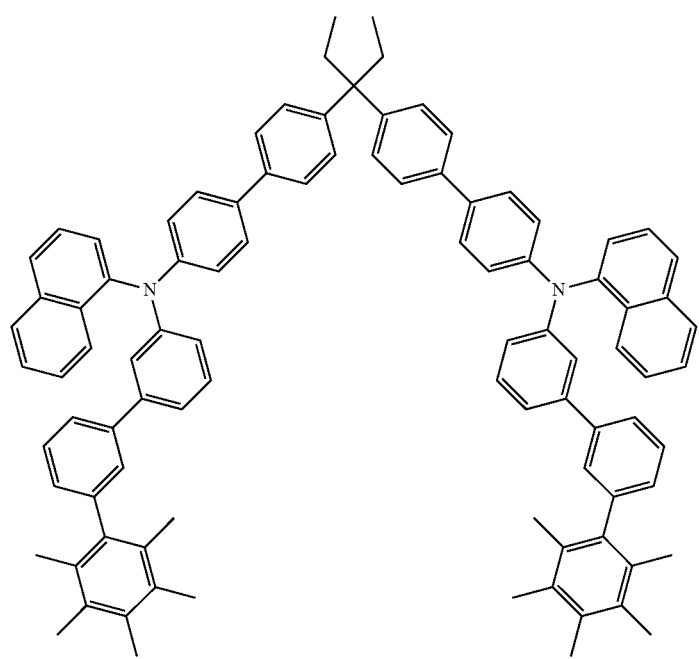

-continued
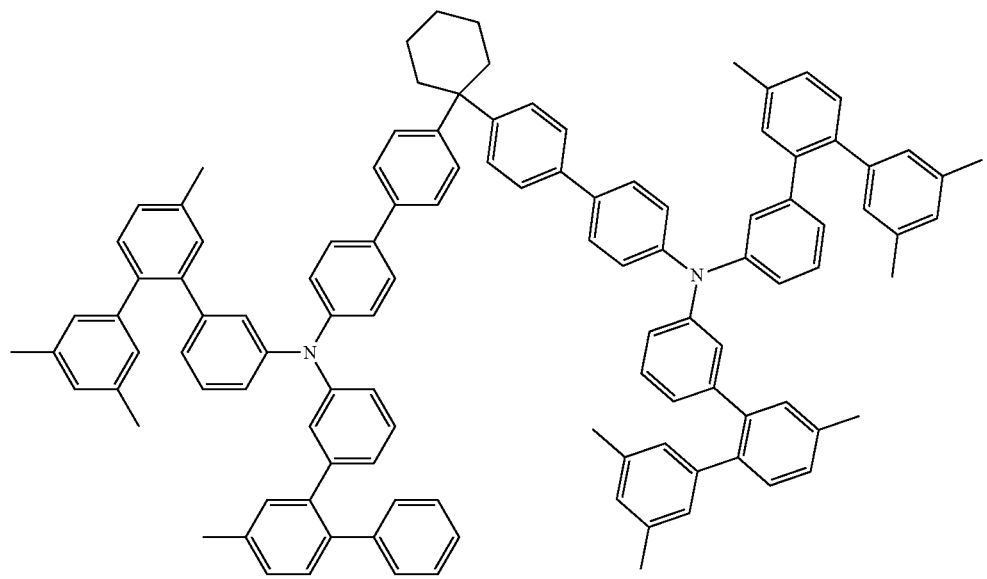
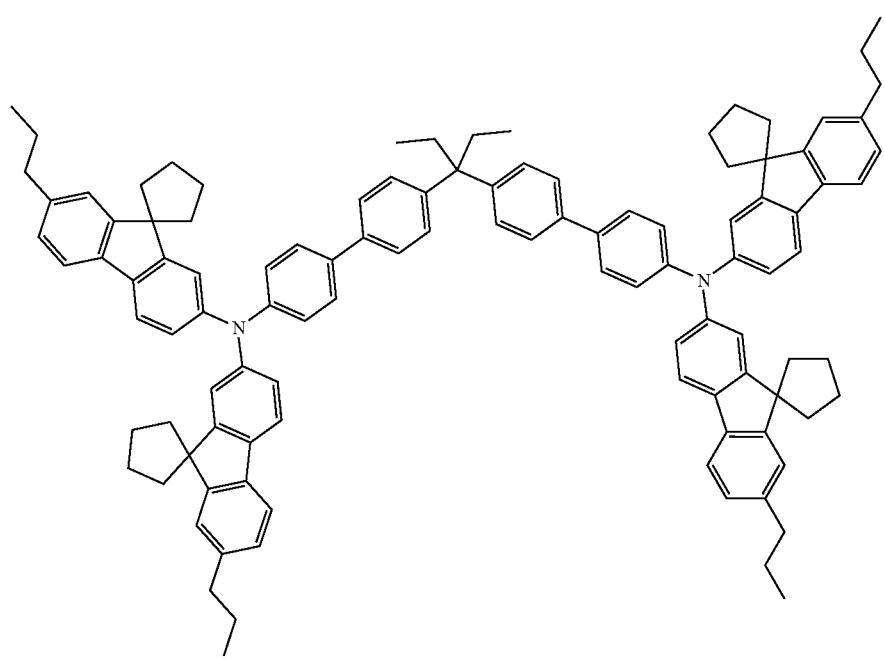

-continued
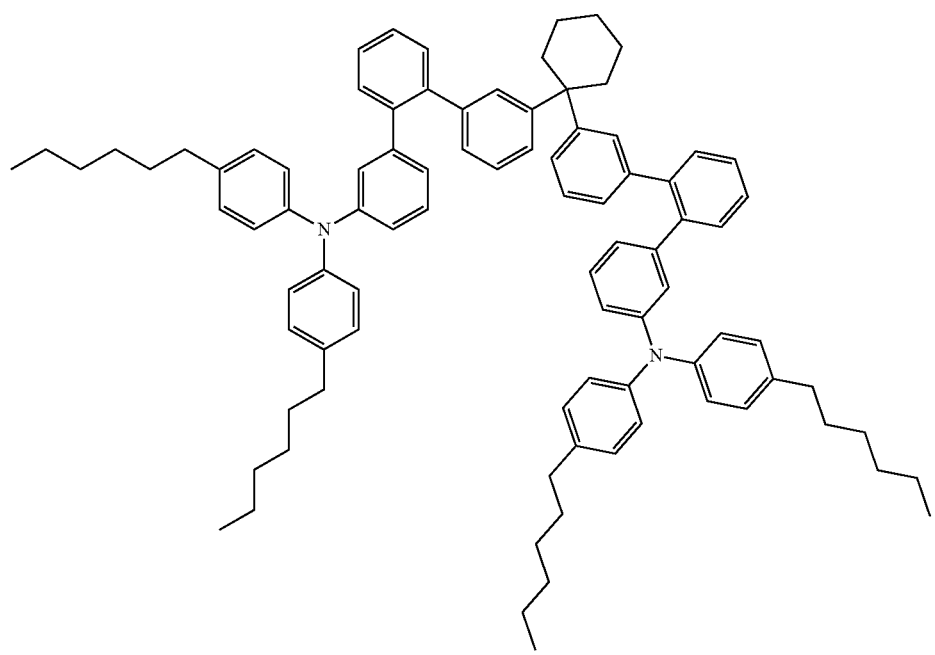
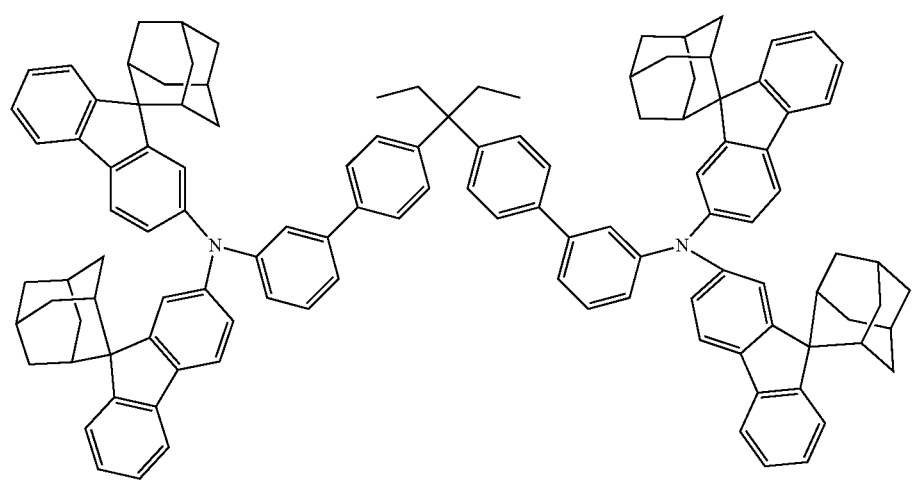

-continued
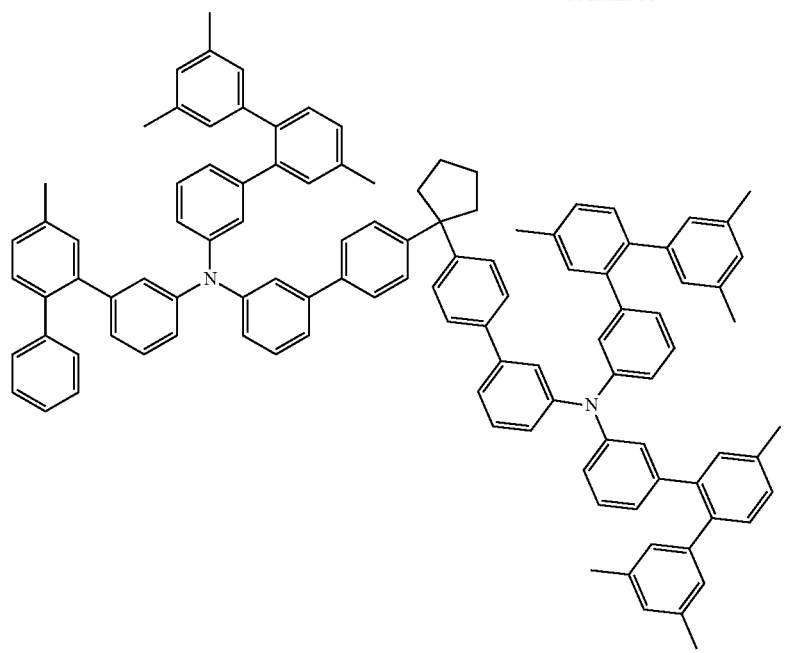
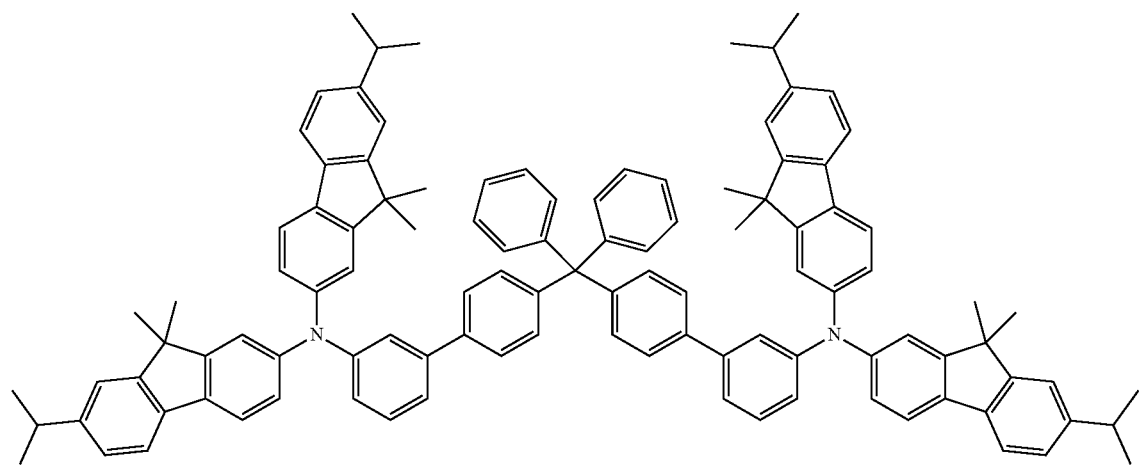
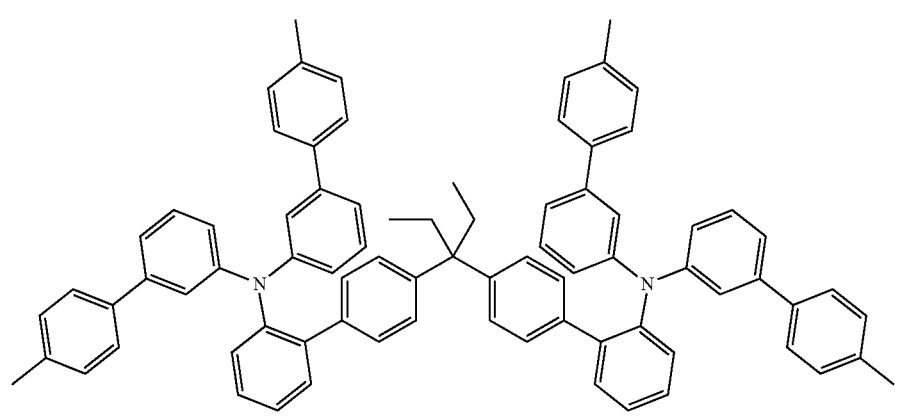

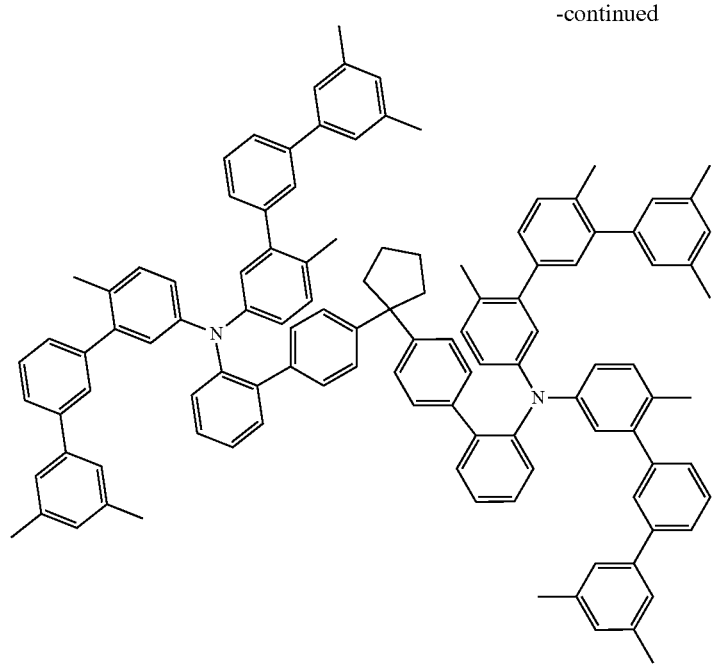
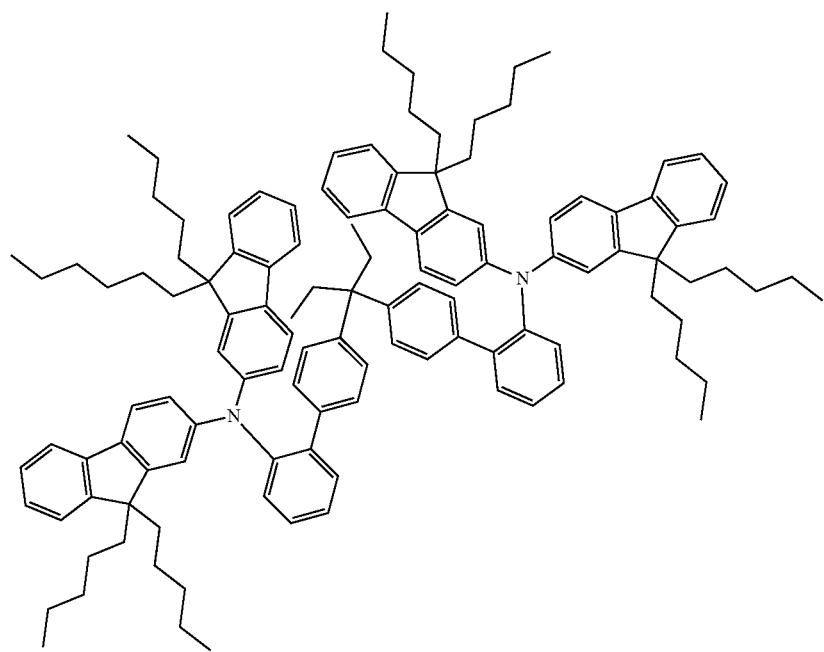

-continued
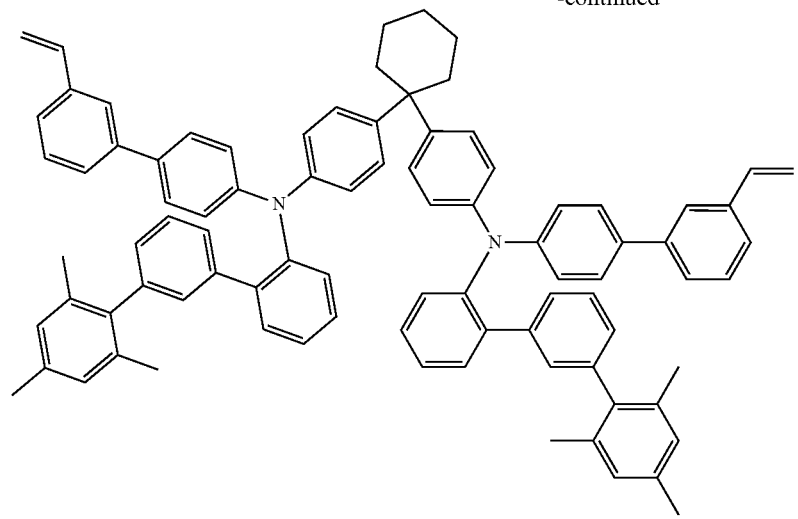
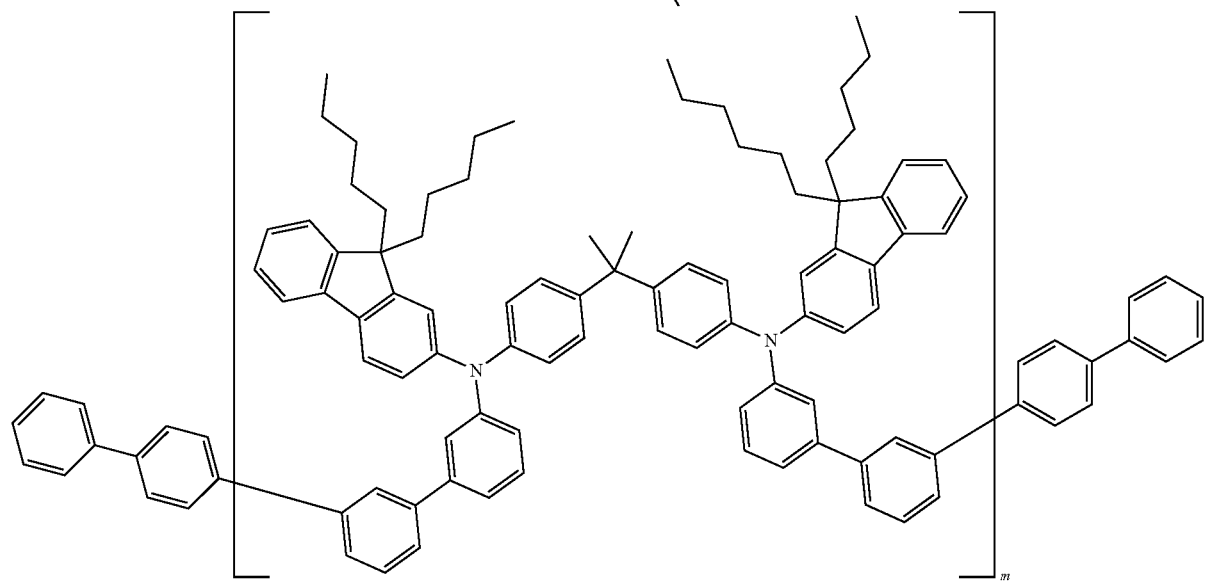
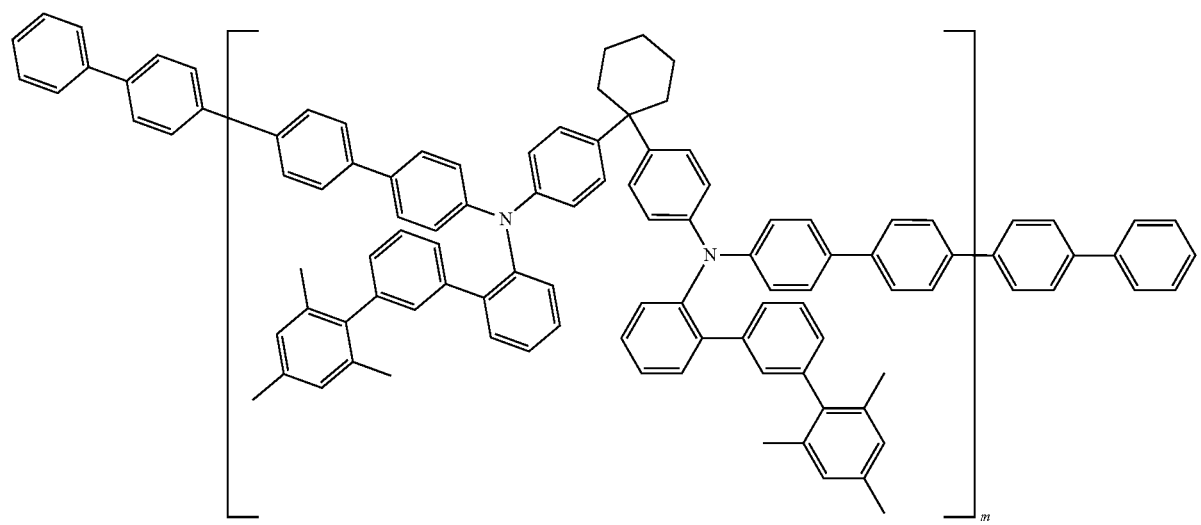

In the structural formulae, m is an integer of 2 or greater.

One embodiment of the present specification provides a composition including the compound of Chemical Formula 1.

In one embodiment of the present specification, the composition is for an organic light emitting device.

In one embodiment of the present specification, the composition includes the compound of Chemical Formula 1 and a solvent.

In one embodiment of the present specification, the composition may be a liquid phase. The "liquid phase" means in a liquid state at room temperature and atmospheric pressure.

In one embodiment of the present specification, examples of the solvent may include chlorine-based solvents such as chloroform, methylene chloride, 1,2-dichloroethane, 1,1,2-trichloroethane, chlorobenzene or o-dichlorobenzene; ether-based solvents such as tetrahydrofuran or dioxane; aromatic hydrocarbon-based solvents such as toluene, xylene, trimethylbenzene or mesitylene; aliphatic hydrocarbon-based solvents such as cyclohexane, methylcyclohexane, n-pentane, n-hexane, n-heptane, n-octane, n-nonane or n-decane; ketone-based solvents such as acetone, methyl ethyl ketone or cyclohexanone; ester-based solvents such as ethyl acetate, butyl acetate or ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin or 1,2-hexanediol, and derivatives thereof; alcohol-based solvents such as methanol, ethanol, propanol, isopropanol or cyclohexanol; sulfoxide-based solvents such as dimethyl sulfoxide; amide-based solvents such as N-methyl-2-pyrrolidone or N,N-dimethylformamide; benzoate-based solvents such as methyl benzoate, butyl benzoate or 3-phenoxybenzoate; tetraline, and the like, however, the solvent is not limited thereto as long as it is a solvent capable of dissolving or dispersing the compound according to one embodiment of the present disclosure.

In another embodiment, the solvent may be used either alone as one type, or as a mixture mixing two or more solvent types.

In another embodiment, the solvent preferably has a boiling point of 40° C. to 250° C. and more preferably 60° C. to 230° C., however, the boiling point is not limited thereto.

In another embodiment, viscosity of the single or mixed solvent is preferably from 1 CP to 10 CP and more preferably from 3 CP to 8 CP, but is not limited thereto.

In another embodiment, the composition preferably has a concentration of 0.1 wt/v % to 20 wt/v % and more preferably 0.5 wt/v % to 5 wt/v %, however, the concentration is not limited thereto.

Another embodiment of the present specification provides an organic light emitting device including the composition.

In one embodiment of the present specification, the organic light emitting device includes a first electrode; a second electrode; and an organic material layer having one or more layers provided between the first electrode and the second electrode, wherein one or more layers of the organic material layer include the composition or a cured material thereof.

In one embodiment of the present specification, the organic material layer including the composition or a cured material thereof is a hole transfer layer, a hole injection layer, or a layer carrying out hole transfer and hole injection at the same time.

In one embodiment of the present specification, the organic material layer includes a light emitting layer, and the light emitting layer includes a: fluorescent dopant or a phosphorescent dopant.

In one embodiment of the present specification, the light emitting layer includes a fluorescent dopant, and the fluorescent dopant is an arylamine compound including an anthracene group or a chrysene group.

In one embodiment of the present specification, the light emitting layer includes a phosphorescent dopant, and the phosphorescent dopant is a metal complex.

In one embodiment of the present specification, the organic material layer includes an electron transfer layer, and the electron transfer layer includes a compound including a phosphine oxide group or a compound including an N-including monocyclic ring.

In one embodiment of the present specification, the organic material layer includes an electron transfer layer, and the electron transfer layer includes a compound including a phosphine oxide group; a compound including pyrimidine; or a compound including triazine.

In one embodiment of the present specification, the organic material layer includes an electron transfer layer, and the electron transfer layer includes a compound represented by the following Chemical Formula 2 or 3.

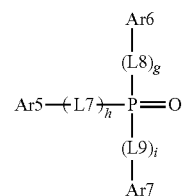

[Chemical Formula 2]

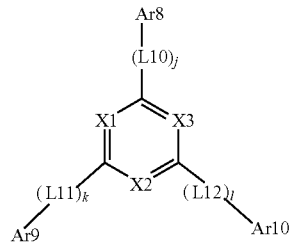

[Chemical Formula 3]

In Chemical Formulae 2 and 3, at least two of X1 to X3 are N, and the remaining one is CR, R is hydrogen; deuterium; a halogen group; a substituted or unsubstituted alkyl group; or a substituted or unsubstituted aryl group, L7 to L12 are the same as or different from each other, and are each independently a direct bond; a substituted or unsubstituted alkylene group; a substituted or unsubstituted divalent cycloalkyl group; a substituted or unsubstituted arylene group; or a substituted or unsubstituted divalent heteroaryl group, Ar5 to Ar10 are the same as or different from each other, and are each independently hydrogen; deuterium; a substituted or unsubstituted alkyl group; a substituted or unsubstituted cycloalkyl group; a substituted or unsubstituted aryl group; or a substituted or unsubstituted heteroaryl group, and g to l are each an integer of 0 to 5, and when g to l are 2 or greater, linking groups in the parentheses are the same as or different from each other.

In one embodiment of the present specification, the compound represented by Chemical Formula 2 is selected from among the following structural formulae.
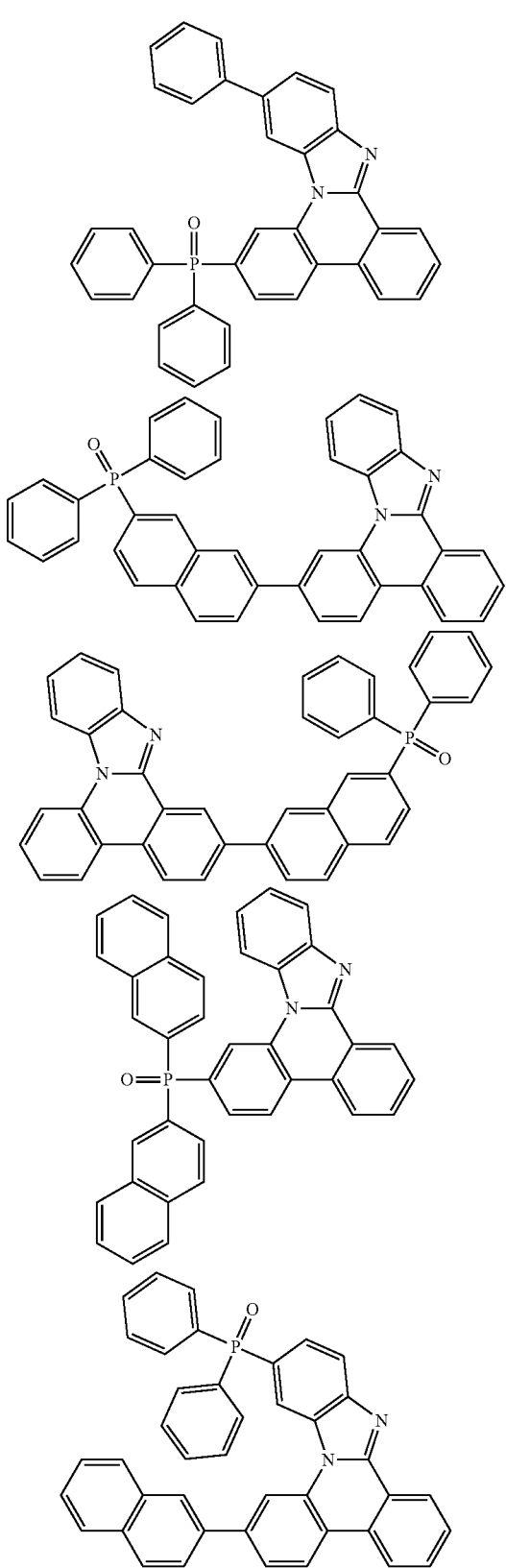
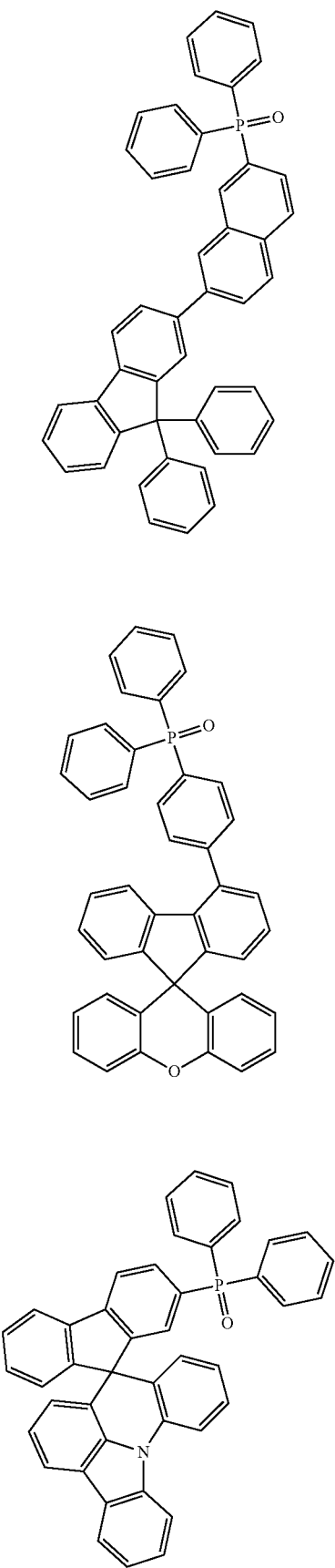

-continued
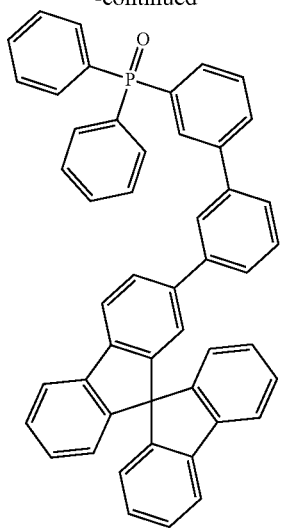
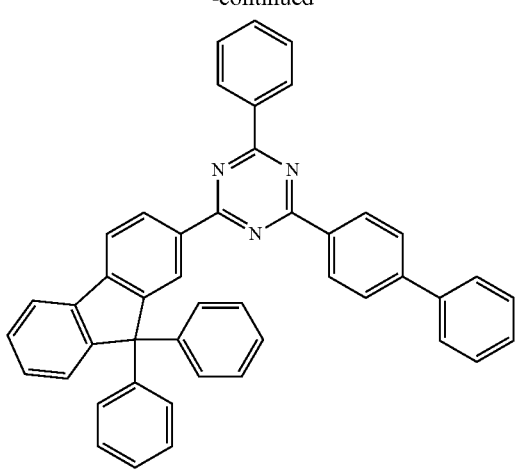
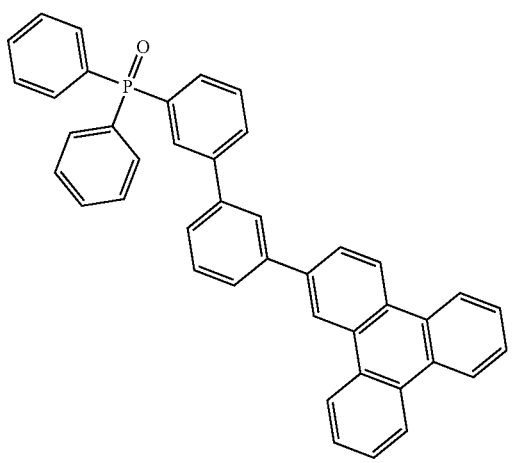
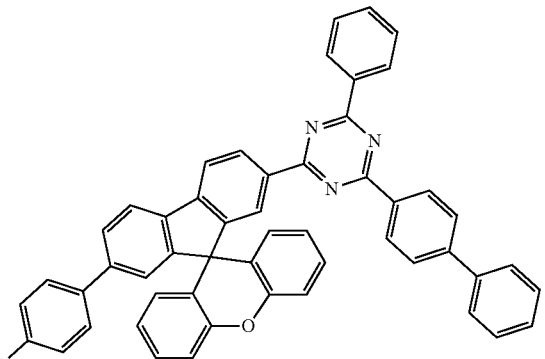
In one embodiment of the present specification, the compound represented by Chemical Formula 3 is selected from among the following structural formulae.
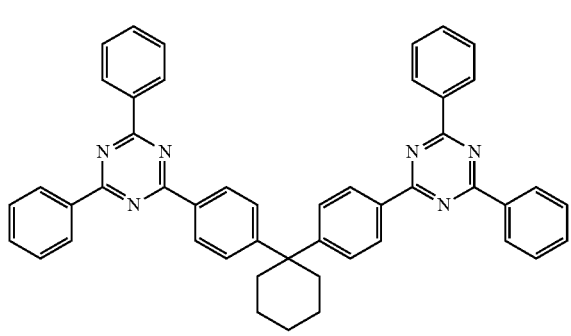
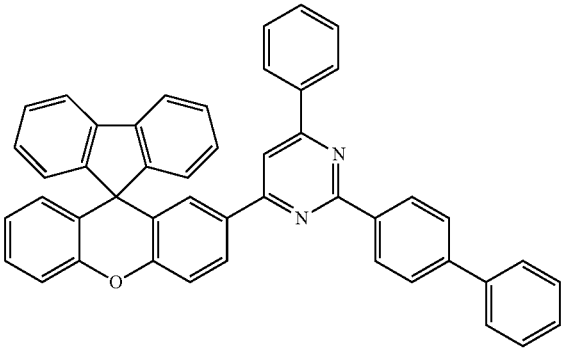

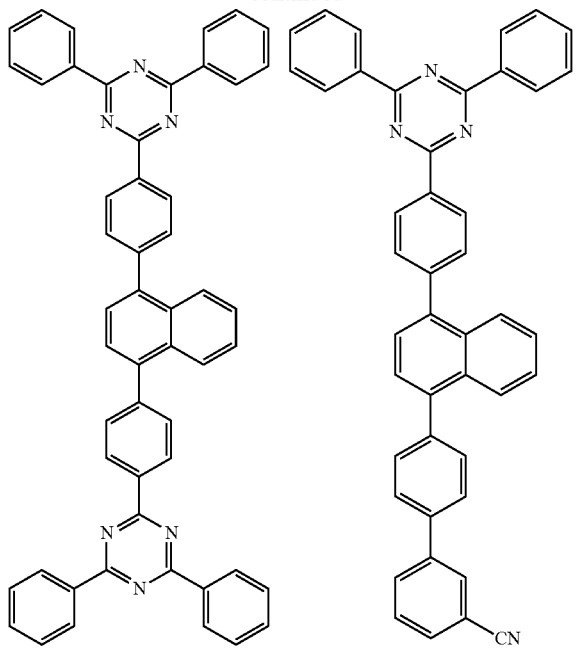
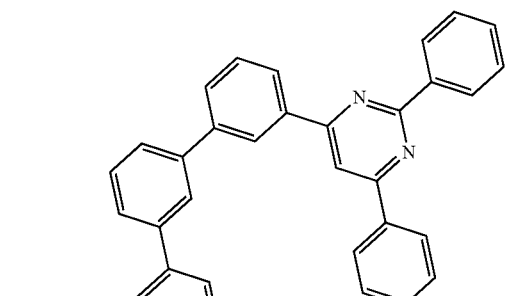
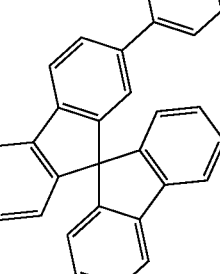
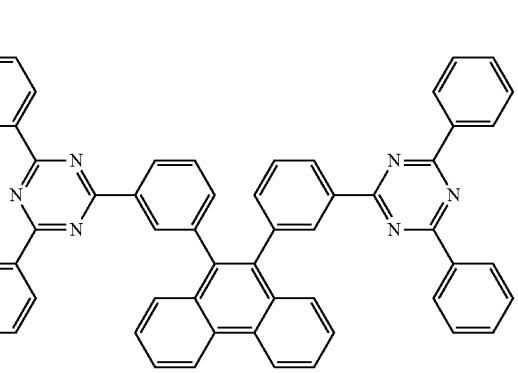
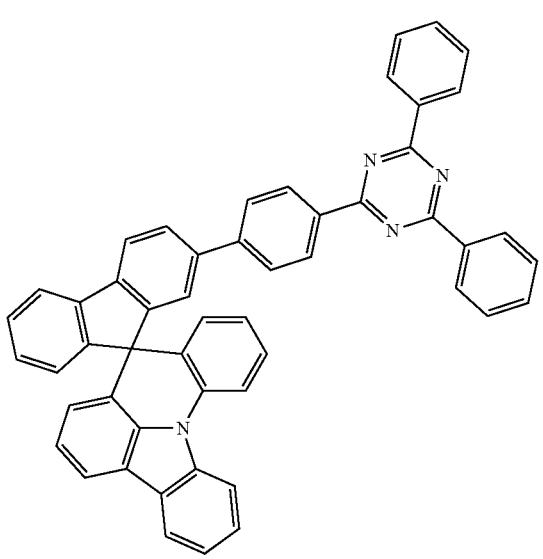
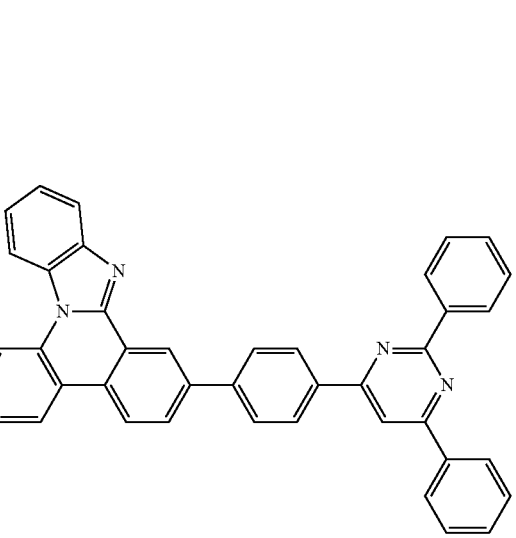

-continued

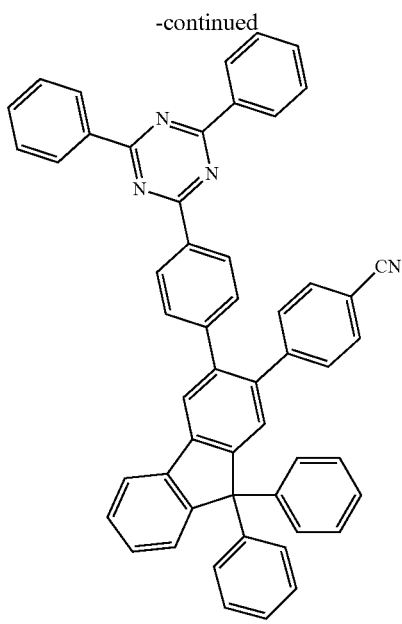

In one embodiment of the present specification, the organic light emitting device has a maximum light emission peak at 380 nm to 750 nm.

In one embodiment of the present specification, the organic light emitting device further includes one, two or more layers selected from the group consisting of a light emitting layer a hole injection layer, a hole transfer layer, an electron transfer layer, an electron injection layer, an electron blocking layer and a hole blocking layer.

In one embodiment of the present specification, the first electrode is a cathode, and the second electrode is an anode.

In one embodiment of the present specification, the first electrode is an anode, and the second electrode is a cathode.

In another embodiment, the organic light emitting device may be an organic light emitting device having a structure in which an anode, an organic material layer having one or more layers, and a cathode are consecutively laminated on a substrate (normal type).

In another embodiment, the organic light emitting device may be an organic light emitting device having a structure in a reverse direction in which a cathode, an organic material layer having one or more layers, and an anode are consecutively laminated on a substrate (inverted type).

The organic material layer of the organic light emitting device of the present specification may be formed in a single layer structure, but may also be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include a smaller number of organic material layers.

For example, a structure of the organic light emitting device according to one embodiment of the present specification is illustrated in FIG. 1.

FIG. 1 illustrates a structure of the organic light emitting device in which an anode (201), a hole transfer layer (301), a light emitting layer (501) and a cathode (601) are consecutively laminated on a substrate (101).

In FIG. 1, the hole transfer layer (301) includes the composition or a cured material thereof.

FIG. 2 illustrates a structure of the organic light emitting device in which an anode (201), a first hole transfer layer (302), a second hole transfer layer (303), a light emitting layer (501), an electron transfer layer (401) and a cathode (601) are consecutively laminated on a substrate (101).

In FIG. 2, the second hole transfer layer (303) includes the composition or a cured material thereof.

FIG. 1 and FIG. 2 illustrate the organic light emitting device, however, the organic light emitting device is not limited thereto.

When the organic light emitting device includes a plurality of organic material layers, the organic material layers may be formed with materials that are the same as or different from each other.

The organic light emitting device of the present specification may be manufactured using materials and methods known in the art, except that one or more layers of the organic material layer include the composition including the compound.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

Another embodiment of the present specification provides a method for manufacturing an organic light emitting device including the composition or a cured material thereof.

Specifically, in one embodiment of the present specification, the method for manufacturing an organic light emitting device includes preparing a substrate; forming a cathode or an anode on the substrate; forming an organic material layer having one or more layers on the cathode or the anode; and forming an anode or a cathode on the organic material layer, wherein one or more layers of the organic material layer include the composition or a cured material thereof.

In one embodiment of the present specification, the organic material layer including the composition is formed using spin coating.

In another embodiment, the organic material layer including the composition is formed using a printing method.

In an embodiment of the present specification, examples of the printing method include inkjet printing, nozzle printing, offset printing, transfer printing, screen printing or the like, but are not limited thereto.

The composition according to one embodiment of the present specification is suited for a solution process due to its structural properties and may be formed using a printing method, and therefore, is economically effective in terms of time and costs when manufacturing a device.

In one embodiment of the present specification, the forming of an organic material layer including the composition includes coating the composition on the cathode or the anode; and heat treating or light treating the coated composition.

In one embodiment of the present specification, the composition is dried by heat treatment.

In one embodiment of the present specification, the time of heat treating the organic material layer including the composition is preferably within 1 hour and more preferably within 30 minutes.

In one embodiment of the present specification, the atmosphere of heat treating the organic material layer formed using the composition is preferably inert gas such as argon or nitrogen.

When the forming of organic material layers using the composition includes the heat treating or light treating, a plurality of fluorene groups included in the composition form crosslinking, and an organic material layer including a thin-filmed structure may be provided. In this case, being dissolved by a solvent deposited on a surface of the organic material layer formed using the composition, or being morphologically influenced or decomposed may be prevented.

Accordingly, when the organic material layer including the composition is formed including the heat treating or light treating, resistance for a solvent increases, and a multilayer may be formed by repeatedly performing solution deposition and crosslinking method, and as a result, lifetime properties of a device may be enhanced due to increased stability.

In one embodiment of the present specification, the composition including the compound may use a composition mixed to a polymer binder and dispersed.

In one embodiment of the present specification, as the polymer binder, those that do not extremely inhibit charge transfer are preferred, and those that do not have strong absorption for visible light are preferably used. Examples of the polymer binder may include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride, polysiloxane and the like.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO: Al or $SnO_2$: Sb; conductive polymers such as poly(3-methylthiophene), poly [3,4-(ethylene-1,2-dioxy)thiophene] (PEDOT), polypyrrole and polyaniline, and the like, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes and thereby has a hole injection effect in an anode and an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and when the organic light emitting device of the present specification includes an additional hole transfer layer or hole transfer material in addition to the hole transfer layer including the composition including the compound represented by Chemical Formula 1 or a cured material thereof, materials capable of receiving holes from an anode or a hole injection layer, moving the holes to a light emitting layer, and having high mobility for the holes are suited as the hole transfer material. Specific examples thereof include arylamine-based organic materials, conductive polymers such as poly(3,4-ethylenedioxythiophene)-polystyrene sulfonate, and block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene, rubrene, or the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto. In addition, a polymer compound may be used, and polymer compounds such as poly-1,4-phenylene or polyfluorene may be included, however, the polymer compound is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group and includes arylamino group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suited. Specific examples thereof include Al complexes of 8-hydroxyquinoline; complexes including $Alq_3$; organic radical compounds; hydroxyflavon-metal complexes, or the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition thereto, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound includes 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato) beryllium, bis(10-hydroxybenzo[h] quinolinato) zinc, bis(2-methyl-8-quinolinato) chlorogallium, bis(2-methyl-8-quinolinato) (o-cresolato) gallium, bis(2-methyl-8-quinolinato) (1-naphtholato)aluminum, bis(2-methyl-8-quinolinato) (2-naphtholato) gallium and the like, but is not limited thereto.

The hole blocking layer is a layer blocking holes from reaching a cathode, and generally, may be formed under the same condition as the hole injection layer. Specifically, oxadiazole derivatives or triazole derivatives, phenanthroline derivatives, BCP, aluminum complexes and the like are included, however, the material is not limited thereto.

The organic light emitting device according to the present specification may be a top-emission type, a bottom-emission type or a dual-emission type depending on the materials used.

In one embodiment of the present specification, the compound may be included in an organic solar cell or an organic transistor in addition to the organic light emitting device.

Hereinafter, the present specification will be described in detail with reference to examples in order to specifically describe the present specification. However, the examples according to the present specification may be modified to various different forms, and the scope of the present specification is not to be construed as being limited to the examples described below. Examples of the present specification are provided in order to more fully describe the present specification to those having average knowledge in the art.

Preparation Example 1. Synthesis of Compound 1

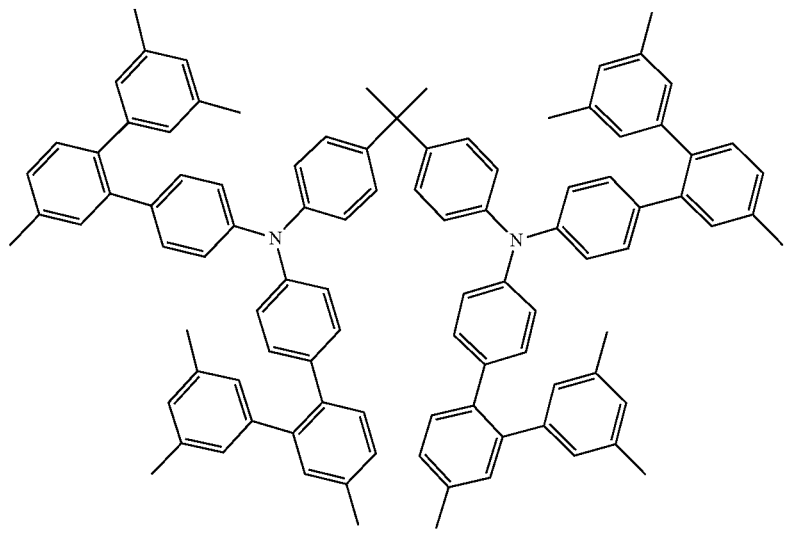

4,4'-(Propane-2,2-diyl)dianiline (100 g, 333.5 mmol), 4"-bromo-3,4', 5-trimethyl-1,1': 2', 1"-terphenyl (100 g, 333.5 mmol) and sodium-t-butoxide (5.3 g, 55.37 mmol) were introduced to xylene, stirred while heating, and then refluxed, and [bis(tri-t-butylphosphine)] palladium (404 mg, 2 mmol %) was introduced thereto. The temperature was lowered to room temperature, and after terminating the reaction, the solvent was removed through vacuum distillation, and the residue was purified by silica gel column chromatography using hexane/chloroform (10:1 to 1:1). The produced material was recrystallized with hexane and methanol to obtain Compound 1 (19.6 g, 82%).

MS $[M+H]^+=1308.82$

Preparation Example 2. Synthesis of Compound 2
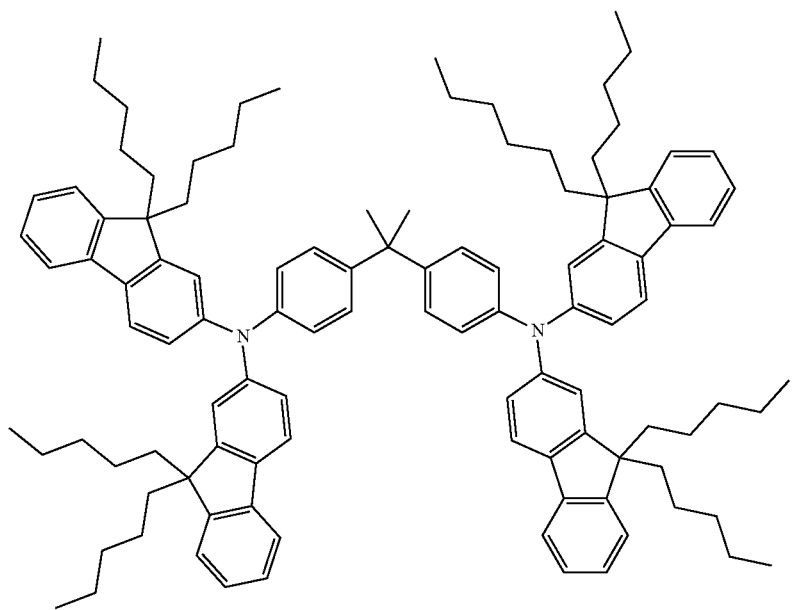 [SMILES: CCCCCCC1(CCCCC)c2ccccc2-c2ccc(N(c3ccc(C(C)(C)c4ccc(N(c5ccc6c(c5)C(CCCCC)(CCCCC)c5ccccc5-6)c5ccc6c(c5)C(CCCCC)(CCCCC)c5ccccc5-6)cc4)cc3)c3ccc4c(c3)C(CCCCC)(CCCCC)c3ccccc3-4)cc21]
Compound 2 was prepared in the same manner as in Preparation Example 1 except that 2-bromo-9,9'-dipentyl-9H-fluorene was used instead of 4"-bromo-3,4', 5-trimethyl-1,1': 2', 1"-terphenyl.
MS [M+H]$^+$=1459.26
Preparation Example 3. Synthesis of Compound 3
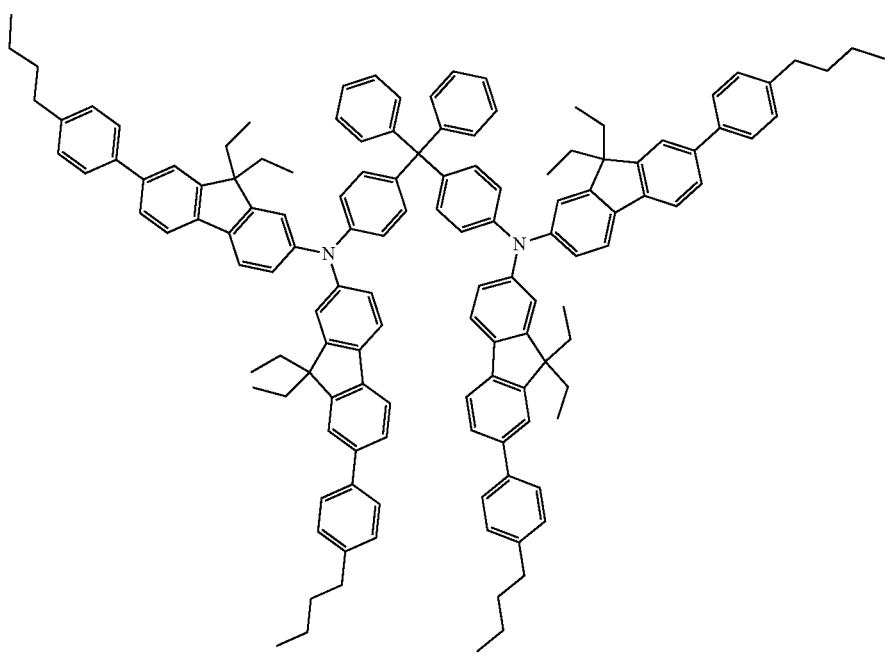 [SMILES: CCCCc1ccc(-c2ccc3c(c2)C(CC)(CC)c2cc(N(c4ccc(C(c5ccccc5)(c5ccccc5)c5ccc(N(c6ccc7c(c6)C(CC)(CC)c6cc(-c8ccc(CCCC)cc8)ccc6-7)c6ccc7c(c6)C(CC)(CC)c6cc(-c8ccc(CCCC)cc8)ccc6-7)cc5)cc4)c4ccc5c(c4)C(CC)(CC)c4cc(-c6ccc(CCCC)cc6)ccc4-5)ccc2-3)cc1]

Compound 3 was prepared in the same manner as in Preparation Example 1 except that 4,4°-(diphenylmethylene)dianiline was used instead of 4,4'-(propane-2,2-diyl) dianiline, and 2-bromo-7-(4-butylphenyl)-9,9-diethyl-9H-fluorene was used instead of 4"-bromo-3,4', 5-trimethyl-1,1': 2', 1"-terphenyl.

MS [M+H]$^+$=1761.55

Preparation Sample 4. Synthesis of Compound 4

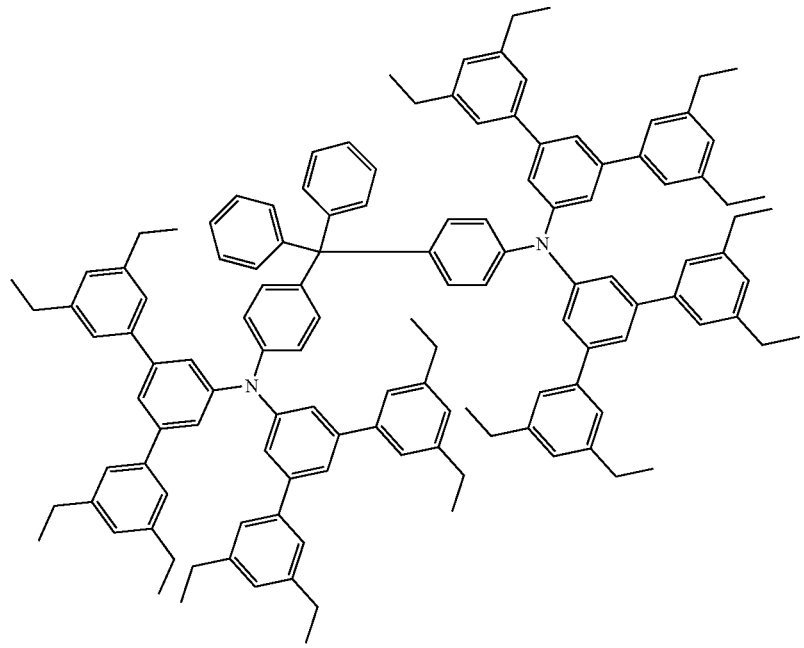 [SMILES: CCc1cc(CC)cc(-c2cc(-c3cc(CC)cc(CC)c3)cc(N(c3ccc(C(c4ccccc4)(c4ccccc4)c4ccc(N(c5cc(-c6cc(CC)cc(CC)c6)cc(-c6cc(CC)cc(CC)c6)c5)c5cc(-c6cc(CC)cc(CC)c6)cc(-c6cc(CC)cc(CC)c6)c5)cc4)cc3)c3cc(-c4cc(CC)cc(CC)c4)cc(-c4cc(CC)cc(CC)c4)c3)c2)c1]

Compound 4 was prepared in the same manner as in Preparation Example except 5'-bromo-3,3", 5,5"-3 that tetraethyl-1, l': 3', 1"-terphenyl was used instead of 2-bromo-/-(4-butylphenyl)-9,9-diethyl-9H-fluorene.

MS [M+H]$^+$=1713.51

Preparation Example 5. Synthesis of Compound 5

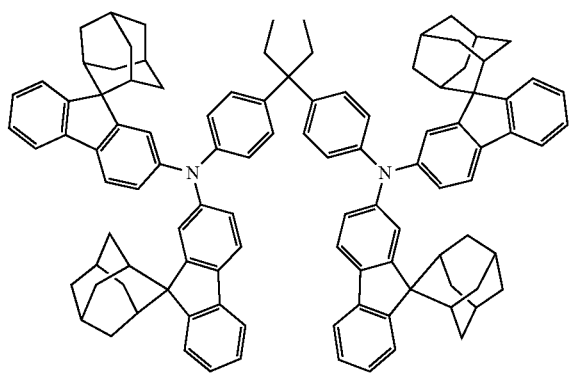 [SMILES: CCC(CC)(c1ccc(N(c2ccc3c(c2)C2(c4ccccc4-3)C3CC4CC(C3)CC2C4)c2ccc3c(c2)C2(c4ccccc4-3)C3CC4CC(C3)CC2C4)cc1)c1ccc(N(c2ccc3c(c2)C2(c4ccccc4-3)C3CC4CC(C3)CC2C4)c2ccc3c(c2)C2(c4ccccc4-3)C3CC4CC(C3)CC2C4)cc1]

Compound 5 was prepared in the same manner as in Preparation Example 1 except that 4,4'-(pentane-3,3-diyl) dianiline was used instead of 4,4'-(propane-2,2- and (1R, 3S, 5r, 7r)-2'-bromospiro [adamantane-diyl)dianiline, 2,9'-fluorene] was used instead of 4"-bromo-3,4', 5-trimethyl-1,1': 2', 1"-terphenyl.

MS [M+H]$^+$=1392.99

Preparation Example 6. Synthesis of Compound 6

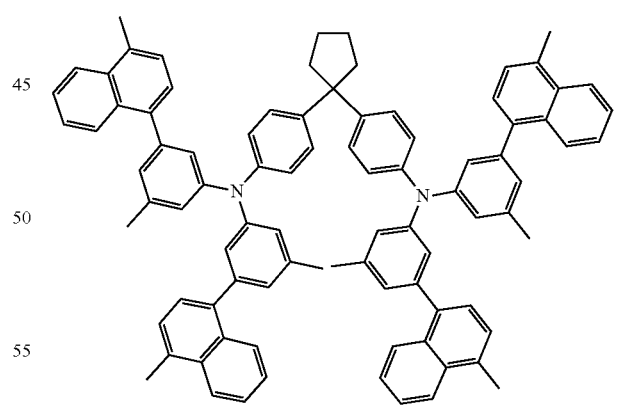

Compound 6 was prepared in the same manner as in Preparation Example 1 except that 4,4'-(cyclopentane-1,1-diyl)dianiline was used instead of 4,4'-(propane-2,2-diyl) dianiline, and 1-(3-bromo-5-methylphenyl)-4-naphthalene was used instead of 4"-bromo-3,4', 5-trimethyl-1,1': 2', 1"-terphenyl.

MS [M+H]$^+$=1174.60

Preparation Example 7. Synthesis of Compound 7

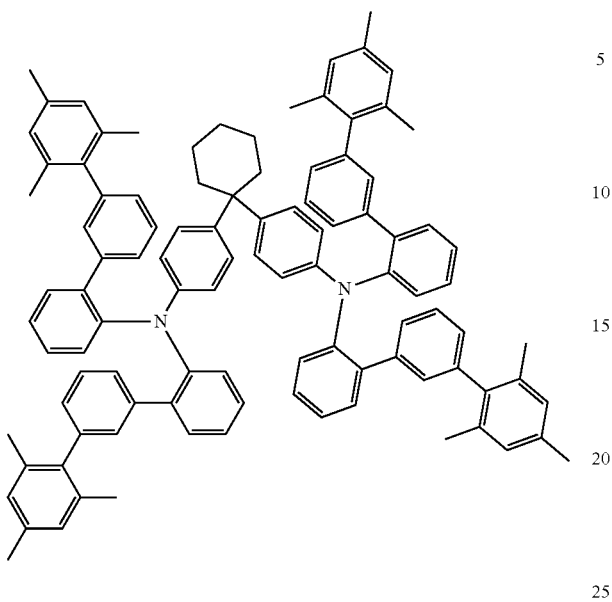

Compound 7 was prepared in the same manner as in Preparation Example 1 except that 4,4'-(cyclohexane-1,1-diyl)dianiline was used instead of 4,4'-(propane-2,2-diyl)dianiline, and 2"-bromo-2,4,6-trimethyl-1,1': 3', 1"-terphenyl was used instead of 4"-bromo-3,4', 5-trimethyl-1,1': 2', 1"-terphenyl.

MS [M+H]$^+$=1348.89

Preparation Example 8. Synthesis of Compound 8

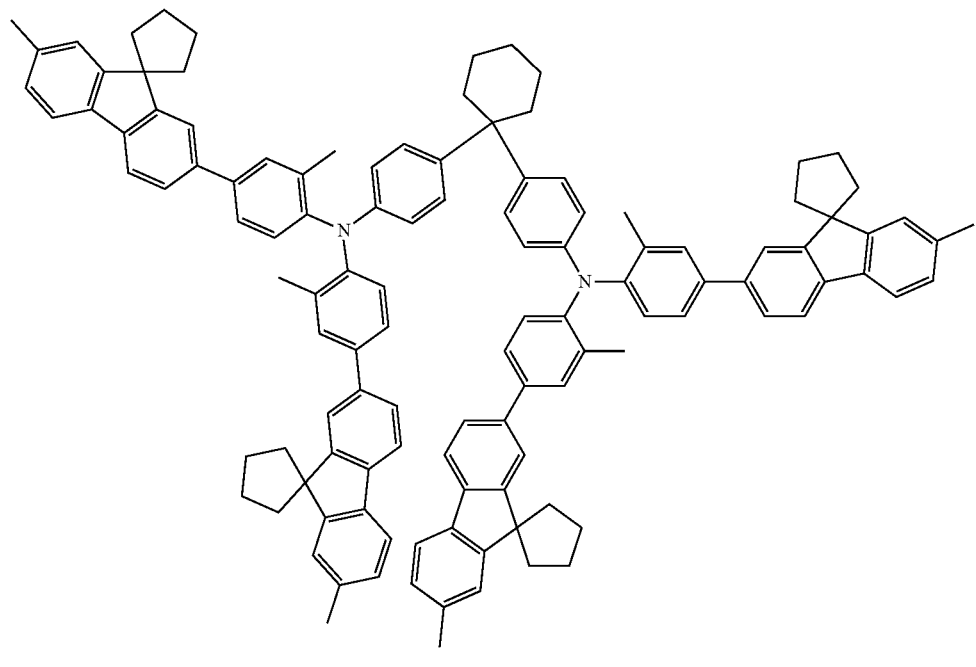

Compound 8 was prepared in the same manner as in Preparation Example 7 except that 2'-(4-bromo-3-methylphenyl)-7'-methylspiro [cyclopentane-1,9'-fluorene] was used instead of 2"-bromo-2,4,6-trimethyl-1,1': 3', 1"-terphenyl.

MS [M+H]$^+$=1557.19

Preparation Sample 9. Synthesis of Compound 9
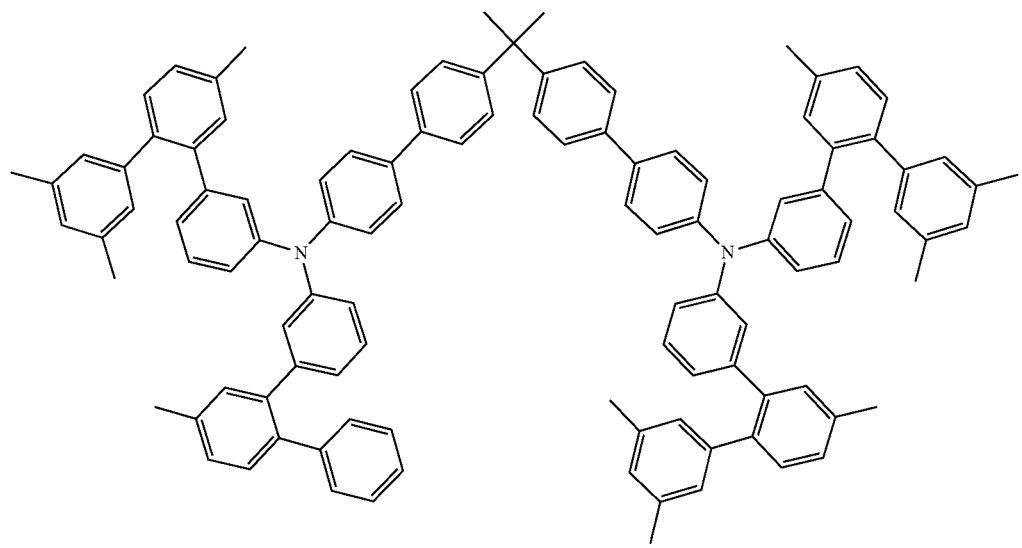
Compound 9 was prepared in the same manner as in Preparation Example 1 except that 4', 4"-(propane-2,2-diyl) bis(4-bromo-1,1'-biphenyl) was used instead of 4,4'-(propane-2,2-diyl)dianiline, and bis(3", 5', 5"-trimethyl-[1,1': 2', 1"-terphenyl]-3-yl)amine was used instead of 4"-bromo-3,4', 5-trimethyl-1,1': 2', 1"-terphenyl.
MS [M+H]$^+$=1432.97
Preparation Example 10. Synthesis of Compound 10
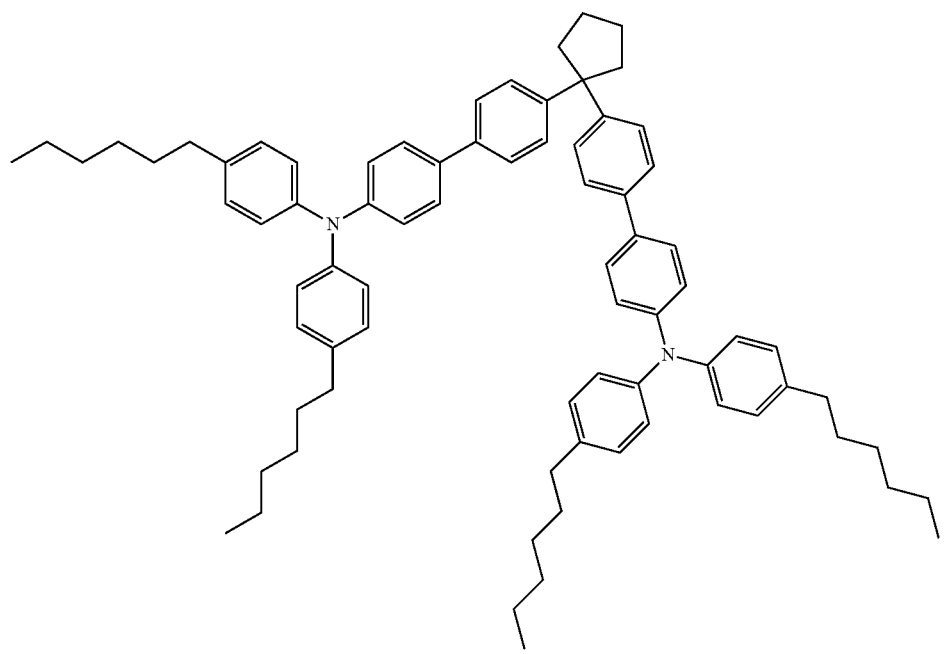 [SMILES: CCCCCCc1ccc(N(c2ccc(CCCCCC)cc2)c2ccc(-c3ccc(C4(c5ccc(-c6ccc(N(c7ccc(CCCCCC)cc7)c7ccc(CCCCCC)cc7)cc6)cc5)CCCC4)cc3)cc2)cc1]

Compound 10 was prepared in the same manner as in Preparation Example 9 except that 4', 4"-(cyclopentane-1,1-diyl)bis(4-bromo-1,1'-biphenyl) was used instead of 4',4"-(propane-2,2-diyl)bis(4-bromo-1,1'-biphenyl), and bis(4-hexylphenyl)amine was used instead of bis(3", 5', 5"-trimethyl-[1,1': 2', 1"-terphenyl]-3-yl)amine.

MS [M+H]⁺=1046.60

Preparation Example 11. Synthesis of Compound 11

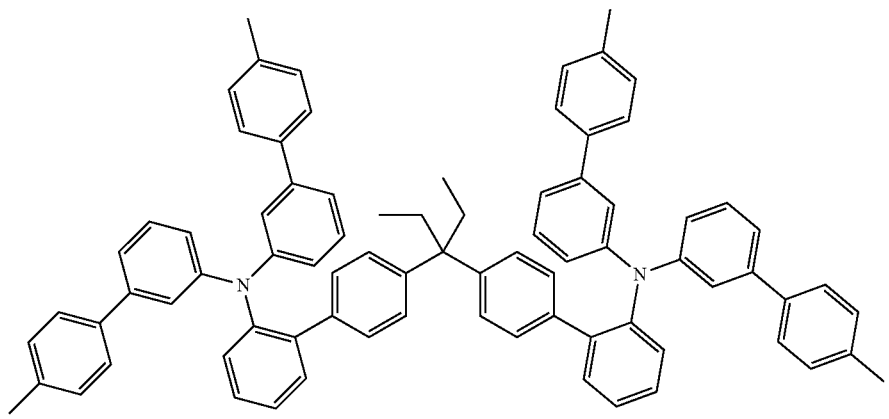

Compound 11 was prepared in the same manner as in Preparation Example 9 except that 4', 4"-([pentane-3,3-diyl) bis(3-bromo-1,1'-biphenyl) was used instead of 4', 4"-(propane-2,2-diyl)bis(4-bromo-1,1'-biphenyl), and bis(4'-methyl-[1,1'-biphenyl]-3-yl)amine was used instead of bis (3", 5', 5"-trimethyl-[1,1': 2', 1"-terphenyl]-3-yl)amine.

MS [M+H]⁺=1072.47

Preparation Example 12. Synthesis of Compound 12

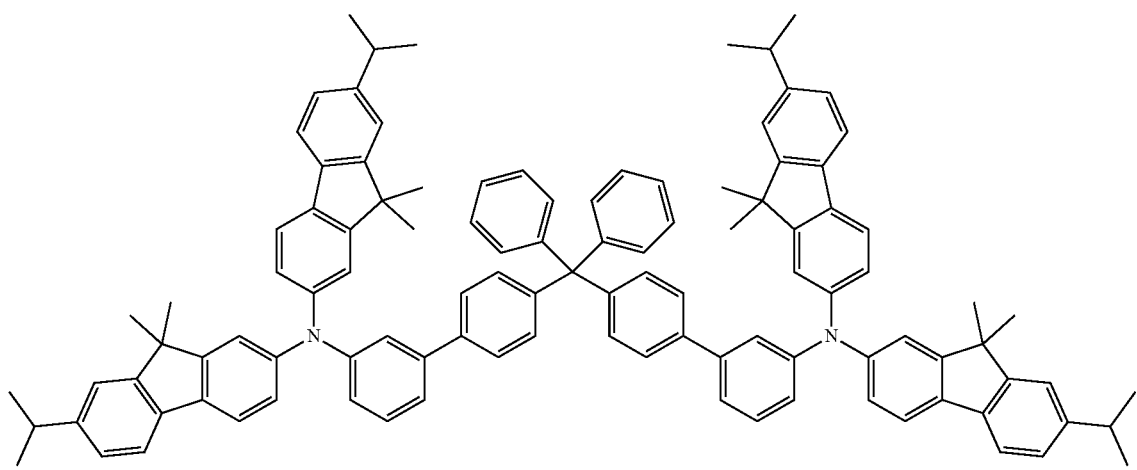 [SMILES: CC(C)c1ccc2c(c1)C(C)(C)c1cc(N(c3cccc(-c4ccc(C(c5ccccc5)(c5ccccc5)c5ccc(-c6cccc(N(c7ccc8c(c7)C(C)(C)c7cc(C(C)C)ccc7-8)c7ccc8c(c7)C(C)(C)c7cc(C(C)C)ccc7-8)c6)cc5)cc4)c3)c3ccc4c(c3)C(C)(C)c3cc(C(C)C)ccc3-4)ccc1-2]

Compound 12 was prepared in the same manner as in Preparation Example 9 except that bis(3'-bromo [1,1'-biphenyl]-4-yl)diphenylmethane was used instead of 4', 4"-(propane-2,2-diyl)bis(4-bromo-1,1'-biphenyl), and bis(7-isopropyl-9,9-dimethyl-9H-fluoren-2-yl)amine was used instead of bis(3", 5', 5"-trimethyl-[1,1': 2', 1"-terphenyl]-3-yl)amine.

MS [M+H]⁺=1441.03

Preparation Example 13. Syntheses of Compounds 13 and P1
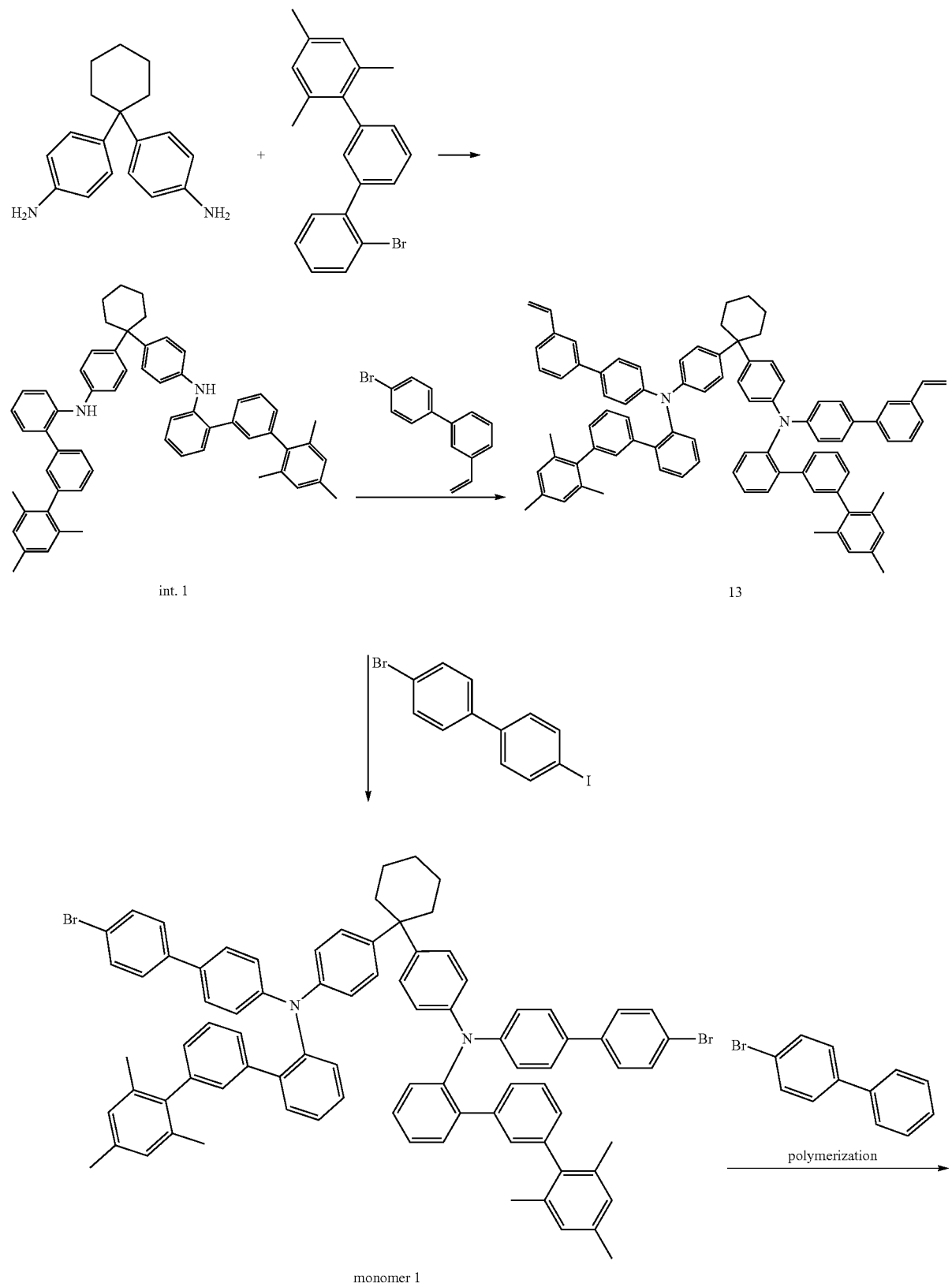

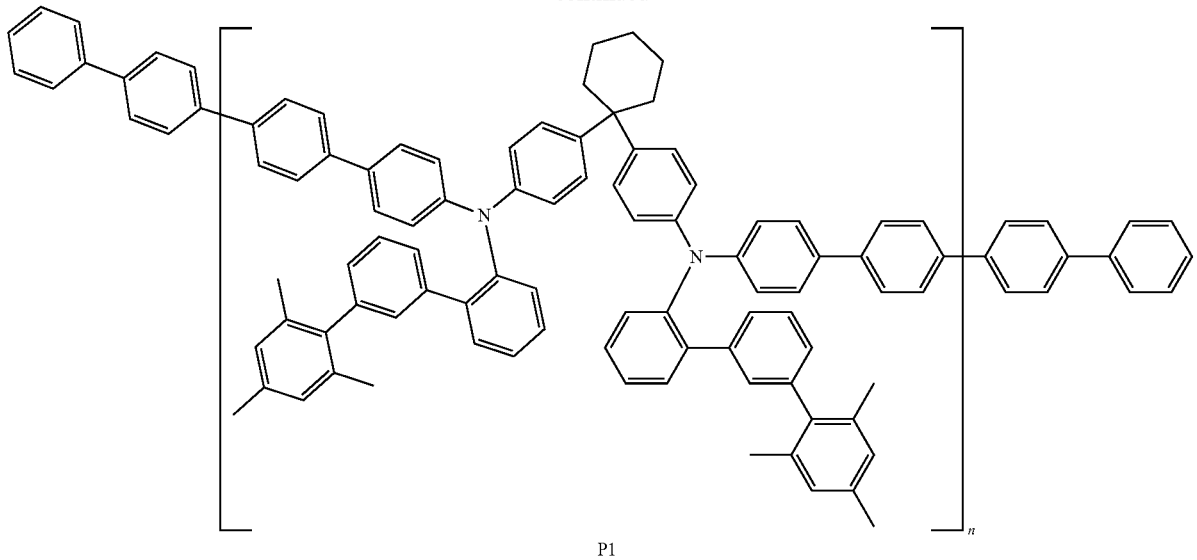

P1

1) Synthesis of Int.1

Int.1 was prepared in the same manner as in Preparation Example 7 except that 2″-bromo-2,4,6-trimethyl-1,1′: 3′, 1″-terphenyl was used in 1 eq. instead of 2 eq . . .

MS [M+H]⁺=808.14

2) Synthesis of Compound 13

Compound 13 was prepared in the same manner as in Synthesis of Int.1 except that Int.1 was used instead of 4,4′-(cyclohexane-1,1-diyl)dianiline, and 4′-bromo-3-vinyl-1,1′-biphenyl was used instead of 2″-bromo-2,4,6-trimethyl-1,1′: 3′, 1″-terphenyl.

MS [M+H]⁺=1164.61

3) Synthesis of Monomer 1

Monomer 1 was prepared in the same manner as in Synthesis of Compound 13 except that 4-bromo-4′-iodo-1,1′-biphenyl was used instead of 4′-bromo-3-vinyl-1,1′-biphenyl.

MS [M+H]⁺=1270.32

4) Synthesis of P1

Monomer 1 (0.848 mmol) and 4-bromobiphenyl (0.053 mmol) were added to a scintillation vial, and dissolved in toluene (15 mL). A transparent dry 50 mL schlenk tube was filled with bis(1,5-cyclooctadiene) nickel (0) (1.63 mmol). 2,2′-Dipyridyl (1.63 mmol) and 1,5-cyclooctadiene (1.63 mmol) were added into a scintillation vial, and dissolved in N, N′-dimethylformamide (12 mL). The solution was added to the schlenk tube, the tube was inserted to an aluminum block and heated to an inner temperature of 60° C., and the temperature was maintained for 30 minutes. The monomer solution in the toluene was added to the schlenk tube, and the tube was sealed. The polymerization mixture was stirred for 3 hours at 60° C. Then, the schlenk tube was removed from the block, and cooled to room temperature. The contents were poured into HCl/methanol (5% v/v, concentrated HCl). After stirring the result for 30 minutes, the polymer was collected by vacuum filtration, and dried under high vacuum. The polymer was dissolved in toluene (1% wt/v), and passed through a column substituted with triethylamine. (10 g) was laminated on silica gel (15 g). The polymer/toluene filtrate was concentrated (3% wt/v toluene) and made into powder with 3-pentanone. The toluene/3-pentanone solution was transferred from the semi-solid polymer, then dissolved in toluene (10 mL), and then poured into stirring methanol to obtain P1 in a 62% yield.

GPC analysis using polystyrene standard Mn=58, 892; Mw=110,872; PDI=1.88

Preparation Example 14. Synthesis of P2

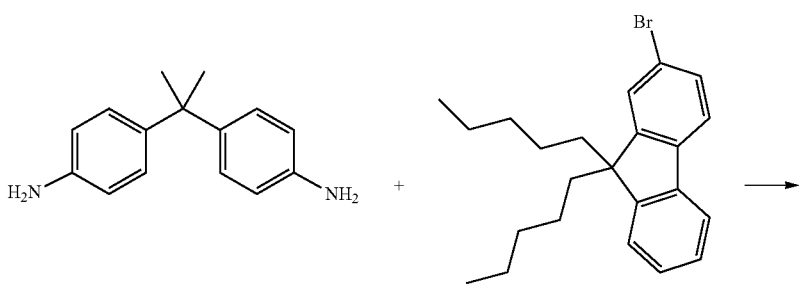

-continued
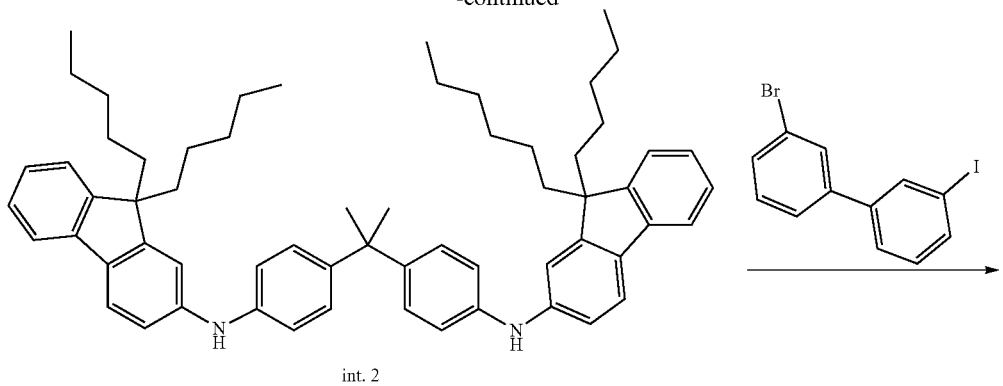
int. 2
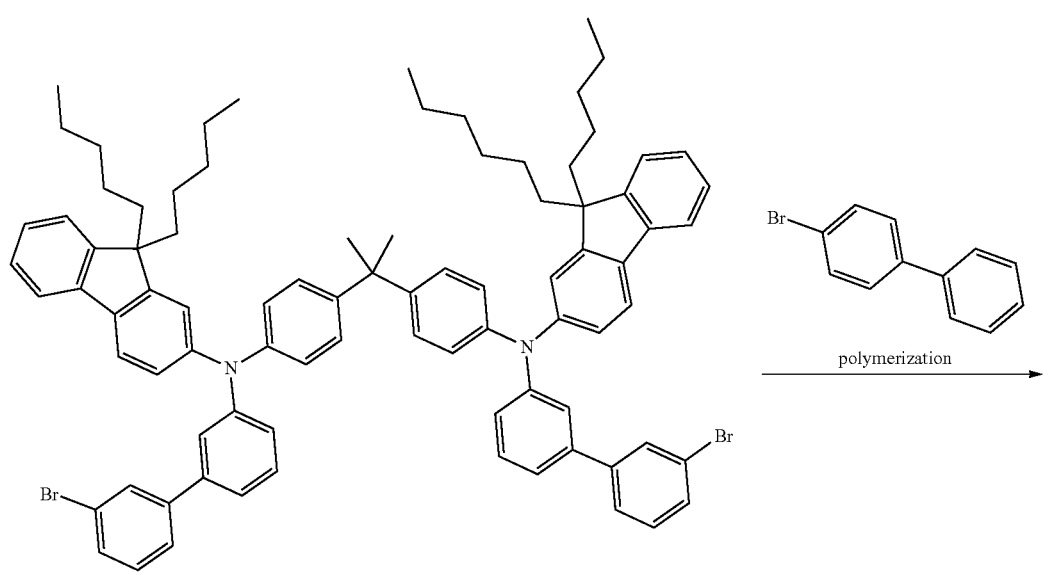
monomer 2
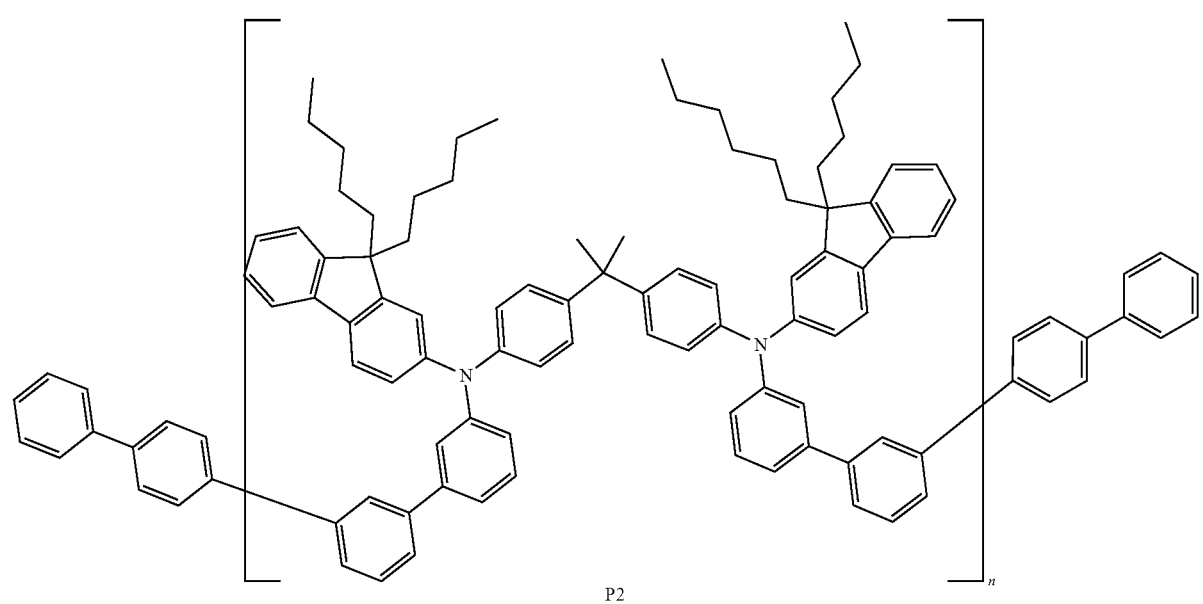
P2

1) Synthesis of Int.2

Int.2 was prepared in the same manner as in Synthesis of Int.1 except that 4,4'-(propane-2,2'-diyl)dianiline was used instead of 4,4'-(cyclohexane-1,1-diyl)dianiline, and 2-bromo-9,9-dipentyl-9H-fluorene was used instead of 2"-bromo-2,4,6-trimethyl-1,1': 3', 1"-terphenyl.

MS [M+H]$^+$=850.30

2) Synthesis of Monomer 2

Monomer 2 was prepared in the same manner as in Synthesis of Monomer 1 except that Int.2 was used instead of Int.1, and 3-bromo-3'-iodo-1,1'-biphenyl was used instead of 4-bromo-4'-iodo-1,1'-biphenyl.

MS [M+H]$^+$=1312.49

3) Synthesis of P2

P2 was prepared in the same manner as in Synthesis of P1 except that Monomer 2 was used instead of Monomer 1. GPC analysis using polystyrene standard Mn=68.325; Mw=113.225; PDI=1.65

EXAMPLE 1

A glass substrate on which indium tin oxide (ITO) was coated as a thin film to a thickness of 1,300 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a solution in which poly(3,4-ethylenedioxythiophene)-polystyrene sulfonate (PEDOT/PSS, manufactured by Bayer AG, Baytron P Al 4083) is diluted to 70% with pure water was spin coated for 30 seconds at 3000 rpm to form a film, and the result was dried for 1 hour at 200° C. to obtain a first hole transfer layer having a film thickness of 30 nm. Subsequently, a solution of a Compound 1 synthesized in Preparation Example 1 (xylene solution, 1 wt %) was spin coated, and dried for 30 minutes at 210° C. under the nitrogen atmosphere to form a second hole transfer layer having a thickness of 20 nm.

The substrate was masked and placed in a vacuum chamber, and host BH1 and dopant BD1 compounds (25:1) were vacuum deposited to a thickness of 300 Å. Then, ET1 (300 Å) was deposited with LiQ in a ratio of 2:1, and thermal vacuum deposited to an electron transfer layer. A cathode was formed on the electron transfer layer by consecutively depositing lithium fluoride (LiF) having a thickness of 12 Å and aluminum having a thickness of 2,000 Å, and as a result, an organic light emitting device was manufactured. The vacuum chamber was evacuated, and the device was encapsulated using a glass lid, a desiccant and UV curable epoxy.

In the above-mentioned process, the deposition rates of the organic materials were maintained at 0.4 Å/sec to 0.7 Å/sec, the deposition rate of the aluminum was maintained at 2 Å/sec, and the degree of vacuum during the deposition was maintained at 1×10$^{-7}$ torr to 5×10$^{-8}$ torr.

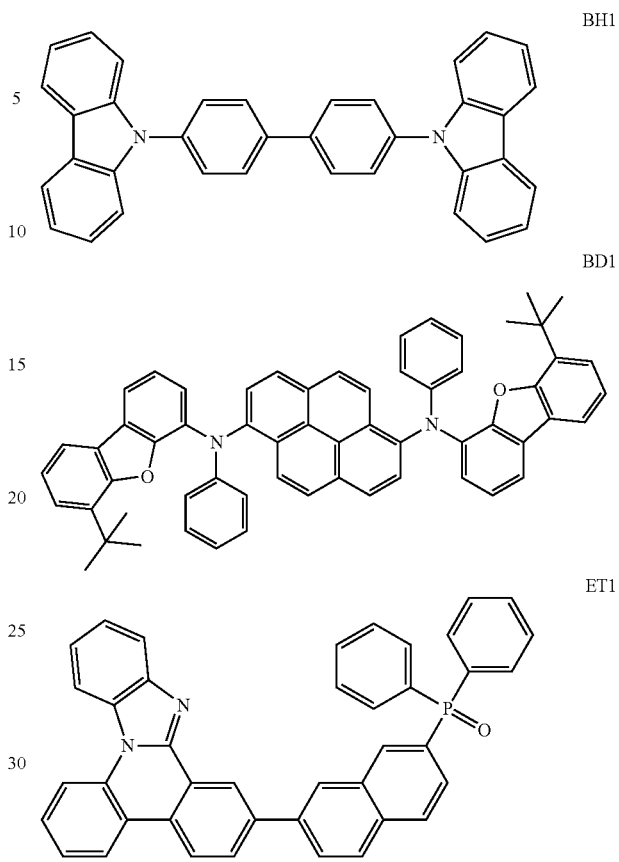

EXAMPLE 2 same manner as in Example 1 except that Compound 2 was used instead of Compound 1 as the second hole transfer layer.

EXAMPLE 3

An organic light emitting device was manufactured in the same manner as in Example 1 except that Compound 3 was used instead of Compound 1 as the second hole transfer layer.

EXAMPLE 4

An organic light emitting device was manufactured in the same manner as in Example 1 except that Compound 4 was used instead of Compound 1 as the second hole transfer layer.

EXAMPLE 5

An organic light emitting device was manufactured in the same manner as in Example 1 except that Compound 5 was used instead of Compound 1 as the second hole transfer layer.

EXAMPLE 6

An organic light emitting device was manufactured in the same manner as in Example 1 except that Compound 6 was used instead of Compound 1 as the second hole transfer layer.

EXAMPLE 7

An organic light emitting device was manufactured in the same manner as in Example 1 except that Compound 7 was used instead of Compound 1 as the second hole transfer layer.

EXAMPLE 8 same manner as in Example 1 except that Compound 8 was used instead of Compound 1 as the second hole transfer layer.

EXAMPLE 9

An organic light emitting device was manufactured in the same manner as in Example 1 except that Compound 9 was used instead of Compound 1 as the second hole transfer layer.

EXAMPLE 10

An organic light emitting device was manufactured in the same manner as in Example 1 except that Compound 10 was used instead of Compound 1 as the second hole transfer layer.

EXAMPLE 11

An organic light emitting device was manufactured in the same manner as in Example 1 except that Compound 11 was used instead of Compound 1 as the second hole transfer layer.

EXAMPLE 12

An organic light emitting device was manufactured in the same manner as in Example 1 except that Compound 12 was used instead of Compound 1 as the second hole transfer layer.

EXAMPLE 13

An organic light emitting device was manufactured in the same manner as in Example 1 except that Compound 13 was used instead of Compound 1 as the second hole transfer layer and crosslinked for 30 minutes at 150° C.

EXAMPLE 14 same manner as in Example 1 except that P1 was used instead of

Compound 1 as the second hole transfer layer.

EXAMPLE 15

An organic light emitting device was manufactured in the same manner as in Example 1 except that P2 was used instead of Compound 1 as the second hole transfer layer.

EXAMPLE 16

An organic light emitting device was manufactured in the same manner as in Example 1 except that ET2 was used instead of ET1 as the electron transfer layer.

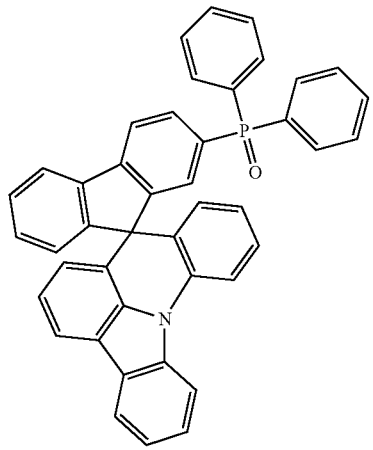

ET2

EXAMPLE 17

An organic light emitting device was manufactured in the same manner as in Example 1 except that Compound 3 was used instead of Compound 1 as the second hole transfer layer, and ET3 was used instead of ET1 as the electron transfer layer.

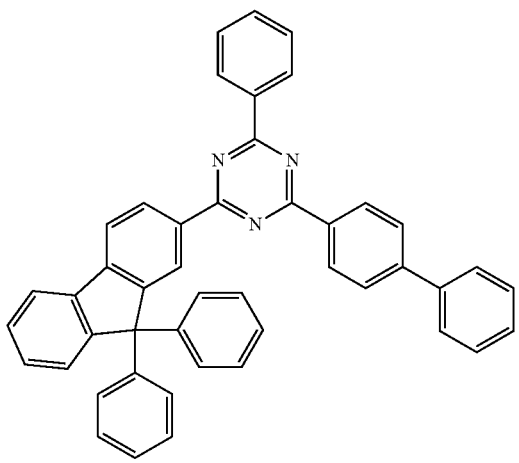

ET3

EXAMPLE 18

An organic light emitting device was manufactured in the same manner as in Example 1 except that Compound 4 was used instead of Compound 1 as the second hole transfer layer, and ET2 was formed as a film to a thickness of 50 Å as the electron transfer layer, and then ET1 and LiQ (2:1) were used to 250 Å as a second electron transfer layer.

EXAMPLE 19

An organic light emitting device was manufactured in the same manner as in Example 1 except that Compound 11 was used instead of Compound 1 as the second hole transfer layer, and ET4 was used alone instead of ET1 as the electron transfer layer.

ET4
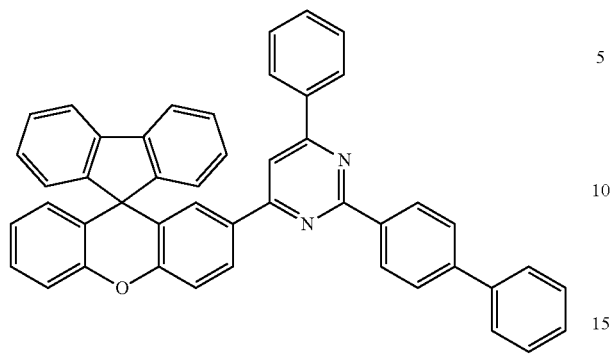
COMPARATIVE EXAMPLE 1
An organic light emitting device was manufactured in the same manner as in Example 1 except that HT1 was used instead of Compound 1 as the second hole transfer layer.
HT1
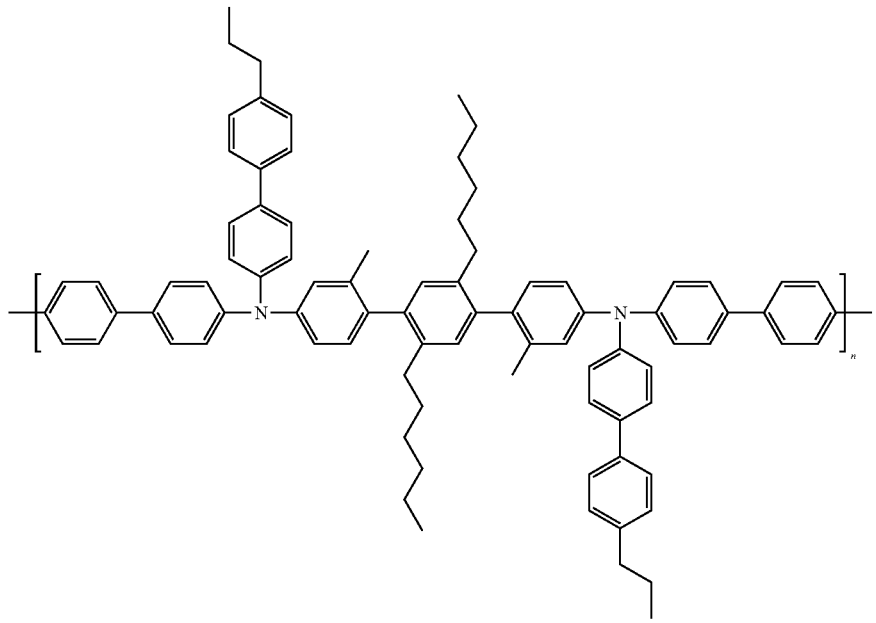
COMPARATIVE EXAMPLE 2
same manner as in Example 1 except that HT2 was used instead of Compound 1 as the second hole transfer layer.
HT2
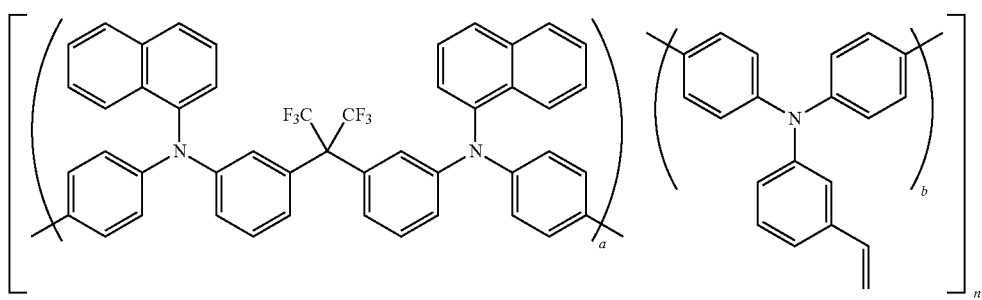
a:b = 2:1

Comparative Example 3

An organic light emitting device was manufactured in the same manner as in Example 1 except that HT3 was used instead of Compound 1 as the second hole transfer layer.

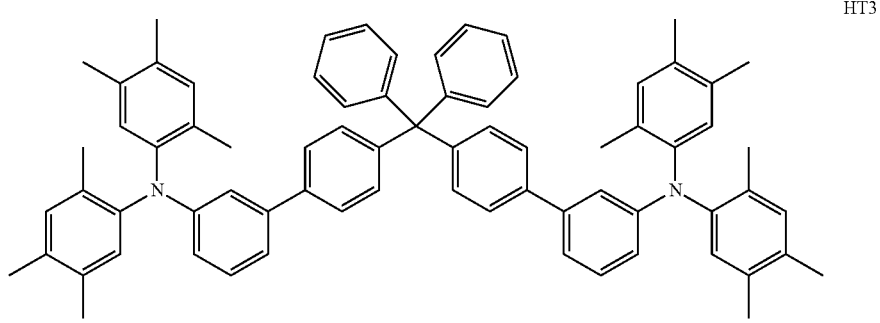

HT3

Comparative Example 4

An organic light emitting device was manufactured in the same manner as in Example 1 except that HT4 was used instead of Compound 1 as the second hole transfer layer.

HT4

Comparative Example 5

An organic light emitting device was manufactured in the same manner as in Example 1 except that HT5 was used instead of Compound 1 as the second hole transfer layer.

HT5

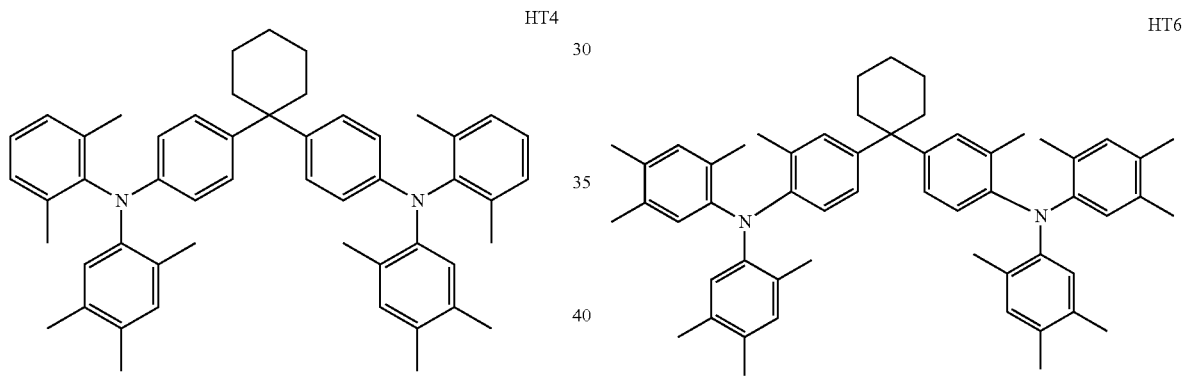

Comparative Example 6

An organic light emitting device was manufactured in the same manner as in Example 1 except that HT6 was used instead of Compound 1 as the second hole transfer layer.

HT6

Comparative Example 7

An organic light emitting device was manufactured in the same manner as in Example 1 except that HT7 was used instead of Compound 1 as the second hole transfer layer.

HT7

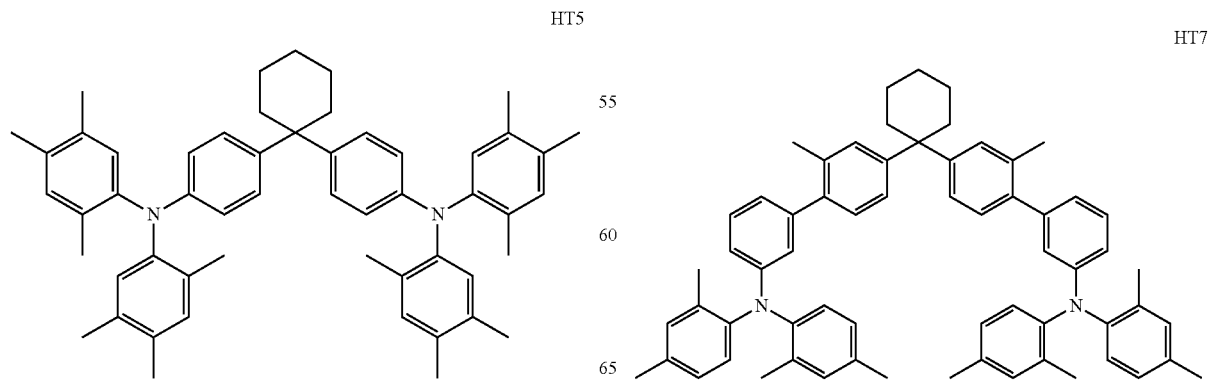
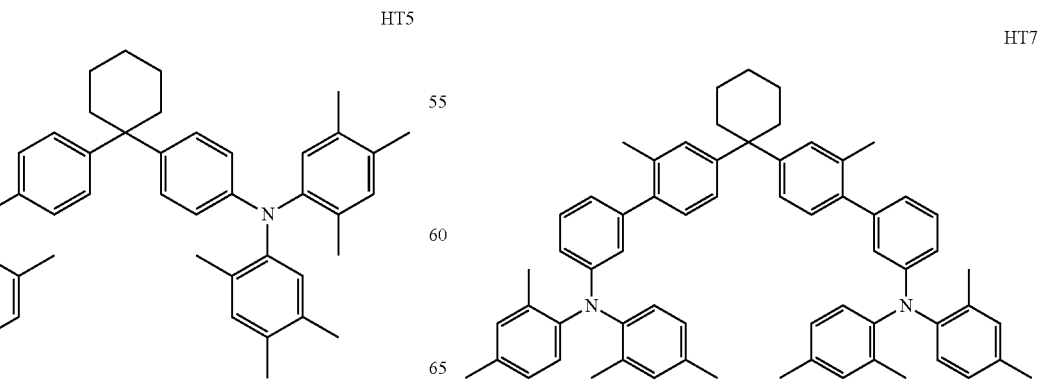

Comparative Example 8

An organic light emitting device was manufactured in the same manner as in Example 1 except that HT8 was used instead of Compound 1 as the second hole transfer layer.

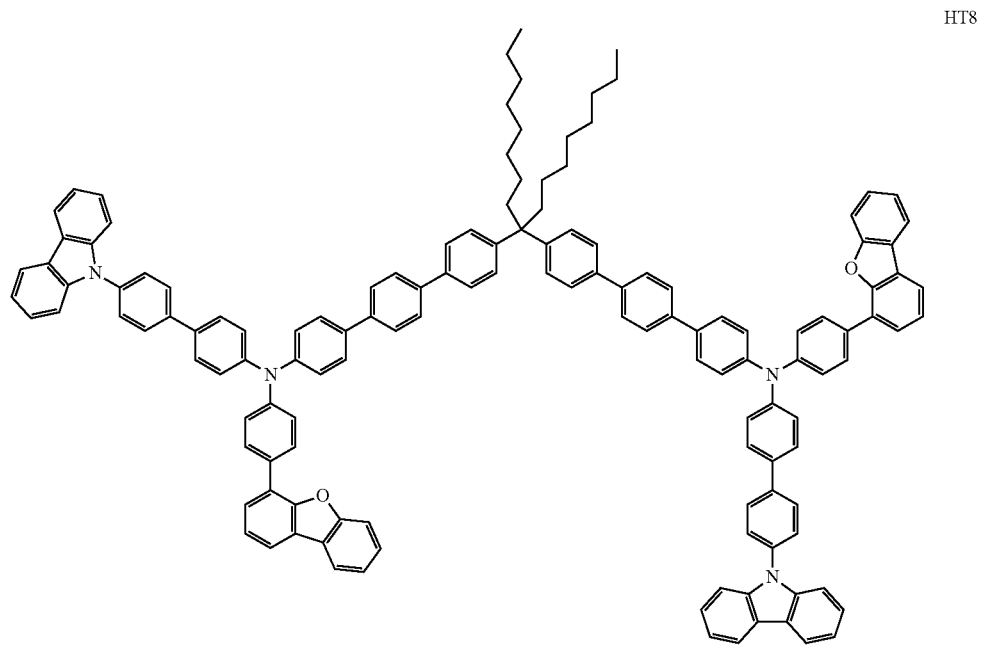 [SMILES: CCCCCCCCC(CCCCCCCC)(c1ccc(-c2ccc(-c3ccc(N(c4ccc(-c5ccc(-n6c7ccccc7c7ccccc76)cc5)cc4)c4ccc(-c5cccc6c5oc5ccccc56)cc4)cc3)cc2)cc1)c1ccc(-c2ccc(-c3ccc(N(c4ccc(-c5ccc(-n6c7ccccc7c7ccccc76)cc5)cc4)c4ccc(-c5cccc6c5oc5ccccc56)cc4)cc3)cc2)cc1]

HT8

Results of experimenting with the blue organic light emitting devices of Examples 1 to 19 and Comparative Examples 1 to 8 are shown in Table 1.

TABLE 1

| Experimental Example 10 mA/cm$^2$ | Second Hole Transfer Layer | Electron Transfer Layer (+LiQ) | Voltage (V) | Efficiency (Cd/A) | Color Coordinate (x, y) | Lifetime (T80, h) (@1000 nit) |
|---|---|---|---|---|---|---|
| Example 1 | Compound 1 | ET1 | 4.53 | 6.71 | (0.135, 0.138) | 12300 |
| Example 2 | Compound 2 | ET1 | 4.42 | 6.63 | (0.134, 0.137) | 11800 |
| Example 3 | Compound 3 | ET1 | 4.49 | 6.58 | (0.135, 0.138) | 11320 |
| Example 4 | Compound 4 | ET1 | 4.55 | 6.82 | (0.134, 0.138) | 12450 |
| Example 5 | Compound 5 | ET1 | 4.51 | 6.72 | (0.136, 0.139) | 9825 |
| Example 6 | Compound 6 | ET1 | 4.55 | 6.52 | (0.135, 0.138) | 10305 |
| Example 7 | Compound 7 | ET1 | 4.52 | 6.69 | (0.133, 0.139) | 12407 |
| Example 8 | Compound 8 | ET1 | 4.46 | 6.78 | (0.135, 0.138) | 8795 |
| Example 9 | Compound 9 | ET1 | 4.39 | 6.58 | (0.134, 0.138) | 9984 |
| Example 10 | Compound 10 | ET1 | 4.45 | 6.67 | (0.136, 0.139) | 10345 |
| Example 11 | Compound 11 | ET1 | 4.57 | 6.77 | (0.136, 0.139) | 13782 |
| Example 12 | Compound 12 | ET1 | 4.33 | 6.72 | (0.135, 0.138) | 13210 |
| Example 13 | Compound 13 (Crosslinked) | ET1 | 4.88 | 6.52 | (0.135, 0.138) | 12348 |

TABLE 1-continued

| Experimental Example 10 mA/cm² | Second Hole Transfer Layer | Electron Transfer Layer (+LiQ) | Voltage (V) | Efficiency (Cd/A) | Color Coordinate (x, y) | Lifetime (T80, h) (@1000 nit) |
|---|---|---|---|---|---|---|
| Example 14 | P1 | ET1 | 4.52 | 6.69 | (0.133, 0.139) | 13450 |
| Example 15 | P2 | ET1 | 4.48 | 6.71 | (0.134, 0.139) | 13820 |
| Example 16 | Compound 1 | ET2 | 4.51 | 6.69 | (0.133, 0.139) | 10568 |
| Example 17 | Compound 3 | ET3 | 4.38 | 6.71 | (0.134, 0.139) | 10068 |
| Example 18 | Compound 4 | ET2/ET1 | 4.68 | 7.12 | (0.135, 0.138) | 12388 |
| Example 19 | Compound 11 | ET4 (Alone) | 5.12 | 6.23 | (0.134, 0.138) | 9210 |
| Comparative Example 1 | HT1 | ET1 | 5.88 | 5.12 | (0.136, 0.139) | 6234 |
| Comparative Example 2 | HT2 | ET1 | 6.03 | 5.88 | (0.135, 0.138) | 7210 |
| Comparative Example 3 | HT3 | ET1 | 7.83 | 3.23 | (0.135, 0.138) | 3410 |
| Comparative Example 4 | HT4 | ET1 | 10.23 | 4.00 | (0.135, 0.138) | 2380 |
| Comparative Example 5 | HT5 | ET1 | 9.87 | 4.12 | (0.135, 0.138) | 1860 |
| Comparative Example 6 | HT6 | ET1 | 8.23 | 3.88 | (0.135, 0.138) | 2025 |
| Comparative Example 7 | HT7 | ET1 | 9.44 | 3.54 | (0.135, 0.138) | 3012 |
| Comparative Example 8 | HT8 | ET1 | 8.23 | 3.68 | (0.135, 0.138) | 2312 |

Examples 1 to 19 and Comparative Examples 1 to 8 of Table 1 are results of a hybrid device in which the hole transfer layer was prepared using a solution process, and the light emitting layer and the electron transfer layer were prepared using a deposition process.

EXAMPLE 20

On a transparent ITO electrode prepared as in Example 1, a solution in which poly(3,4-ethylenedioxythiophene)-polystyrene sulfonate (PEDOT/PSS, manufactured by Bayer AG, Baytron P Al 4083) is diluted to 70% with pure water was spin coated for 30 seconds at 3000 rpm to form a film, and the result was dried for 1 hour at 200° C. to prepare a first hole transfer layer having a film thickness of 30 nm. Subsequently, a solution of a Compound 1 material synthesized in Preparation Example 1 (xylene solution, 1 wt %) was spin coated, and dried for 30 minutes at 210° C. under the nitrogen atmosphere to form a second hole transfer layer having a thickness of 20 nm.

After cooling, the substrate was spin coated using a methyl benzoate solution of a dopant and a host, and the solvent was removed by heating. A light emitting layer solution was prepared as a 1 wt % methyl benzoate solution of BH2: BD2=2:1. The substrate was masked and placed in a vacuum chamber, and then ET1 (300 Å) was deposited with LiQ in a ratio of 2:1 and thermal vacuum deposited to an electron transfer layer. A cathode was formed on the electron transfer layer by consecutively depositing lithium fluoride (LiF) having a thickness of 12 Å and aluminum having a thickness of 2,000 Å, and as a result, an organic light emitting device was manufactured. The vacuum chamber was evacuated, and the device was encapsulated using a glass lid, a desiccant and UV curable epoxy.

In the above-mentioned process, the deposition rates of the organic materials were maintained at 0.4 Å/sec to 0.7 Å/sec, the deposition rate of the aluminum was maintained at 2 Å/sec, and the degree of vacuum during the deposition was maintained at $1 \times 10^{-7}$ torr to $5 \times 10^{-8}$ torr.

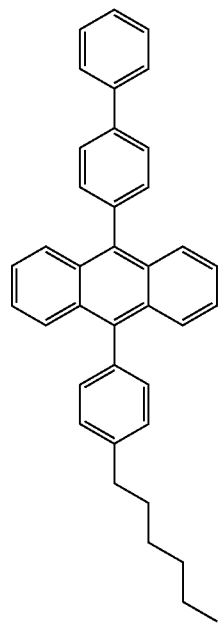

BH2

-continued

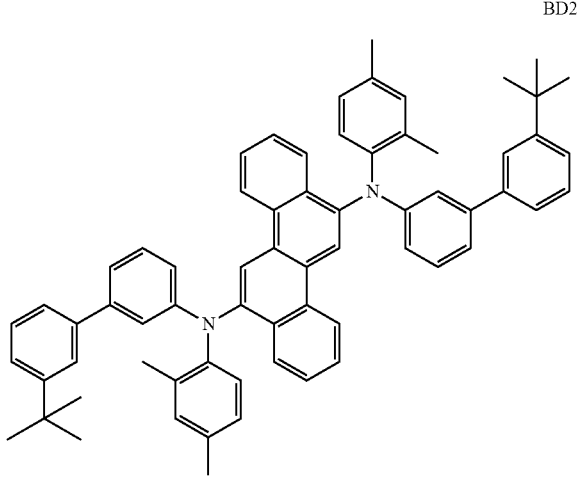
BD2

EXAMPLE 21

An organic light emitting device was manufactured in the same manner as in Example 20 except that Compound 3 was used instead of Compound 1 as the second hole transfer layer.

EXAMPLE 22

An organic light emitting device was manufactured in the same manner as in Example 20 except that Compound 4 was used instead of Compound 1 as the second hole transfer layer.

EXAMPLE 23

An organic light emitting device was manufactured in the same manner as in Example 20 except that Compound 7 was used instead of Compound 1 as the second hole transfer layer.

EXAMPLE 24

An organic light emitting device was manufactured in the same manner as in Example 20 except that Compound 9 was used instead of Compound 1 as the second hole transfer layer.

EXAMPLE 25

An organic light emitting device was manufactured in the same manner as in Example 20 except that Compound 11 was used instead of Compound 1 as the second hole transfer layer.

EXAMPLE 26

An organic light emitting device was manufactured in the same manner as in Example 20 except that Compound 12 was used instead of Compound 1 as the second hole transfer layer.

EXAMPLE 27

An organic light emitting device was manufactured in the same manner as in Example 20 except that ET3 was used instead of ET1 as the electron transfer layer.

EXAMPLE 28

An organic light emitting device was manufactured in the same manner as in Example 20 except that Compound 8 was used instead of Compound 1 as the second hole transfer layer, and ET5 was used instead of ET1 as the electron transfer layer.

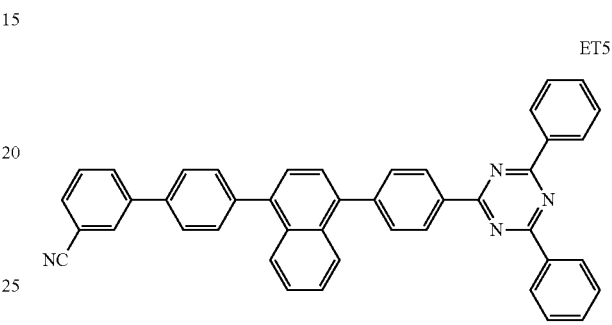
ET5

EXAMPLE 29

An organic light emitting device was manufactured in the same manner as in Example 20 except that Compound 13 was used instead of Compound 1 as the second hole transfer layer and crosslinked for 30 minutes at 150° C., and ET5 was used alone instead of ET1 as the electron transfer layer.

EXAMPLE 30

An organic light emitting device was manufactured in the same manner as in Example 20 except that Compound 12 was used instead of Compound 1 as the second hole transfer layer, and ET1 was formed as a film to a thickness of 50 Å as a first electron transfer layer, and then ET5 and LiQ (2:1) were used to 250 Å as a second electron transfer layer.

COMPARATIVE EXAMPLE 10

An organic light emitting device was manufactured in the same manner as in Example 20 except that HT1 was used instead of Compound 1 as the second hole transfer layer, and ET5 was used instead of ET1 as the electron transfer layer.

COMPARATIVE EXAMPLE 11

An organic light emitting device was manufactured in the same manner as in Example 20 except that HT2 was used instead of Compound 1 as the second hole transfer layer, and ET2 was formed as a film to a thickness of 50 Å as a first electron transfer layer, and then ET4 and LiQ (2:1) were used to 250 Å as a second electron transfer layer.

COMPARATIVE EXAMPLE 12

An organic light emitting device was manufactured in the same manner as in Example 20 except that the following HT9 was used instead of Compound 1 as the second hole transfer layer.

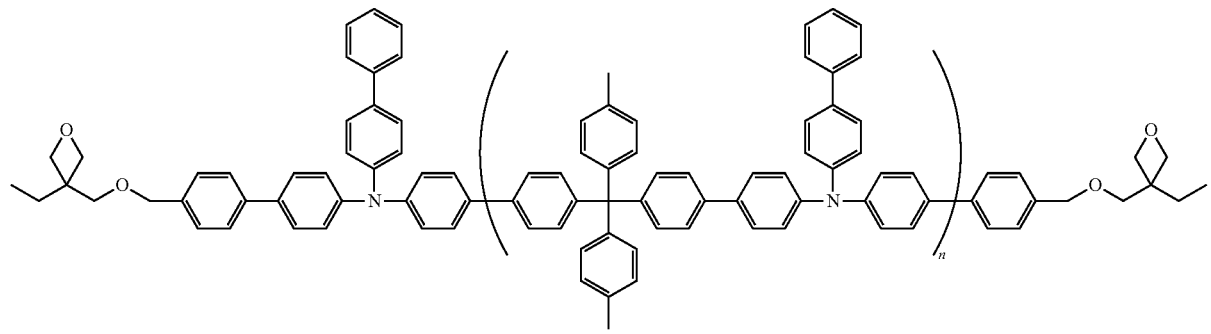

HT9

COMPARATIVE EXAMPLE 13

An organic light emitting device was manufactured in the same manner as in Example 20 except that the following HT10 was used instead of Compound 1 as the second hole transfer layer.

[HT10]

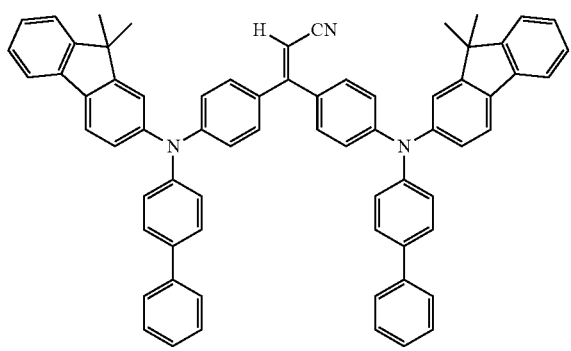 [SMILES: CC1(C)c2ccccc2-c2ccc(N(c3ccc(C(=CC#N)c4ccc(N(c5ccc(-c6ccccc6)cc5)c5ccc6c(c5)C(C)(C)c5ccccc5-6)cc4)cc3)c3ccc(-c4ccccc4)cc3)cc21]

COMPARATIVE EXAMPLE 14

An organic light emitting device was manufactured in the same manner as in Example 20 except that the following HT11 was used instead of Compound 1 as the second hole transfer layer.

[HT11]

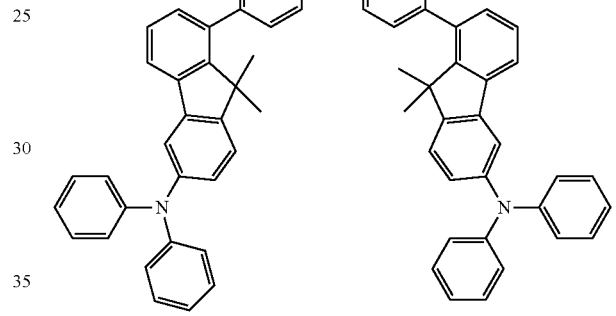

COMPARATIVE EXAMPLE 15

An organic light emitting device was manufactured in the same manner as in Example 20 except that the following HT12 was used instead of Compound 1 as the second hole transfer layer.

[HT12]

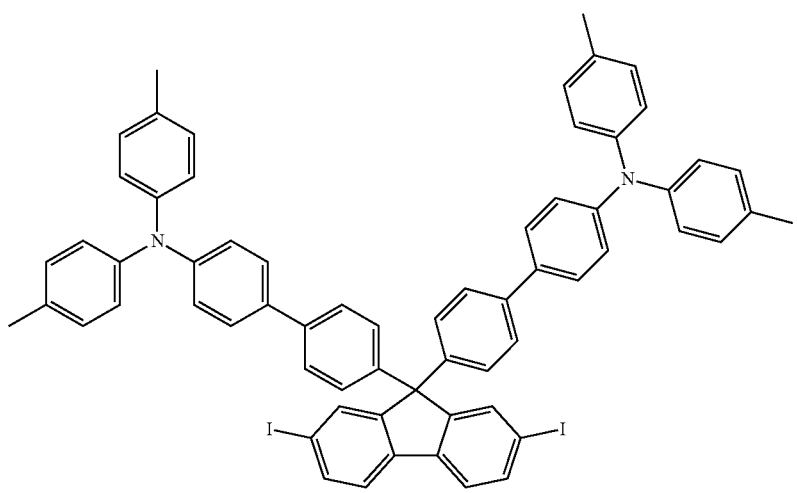

COMPARATIVE EXAMPLE 16

An organic light emitting device was manufactured in the same manner as in Example 20 except that the following HT13 was used instead of Compound 1 as the second hole transfer layer.

[HT13]

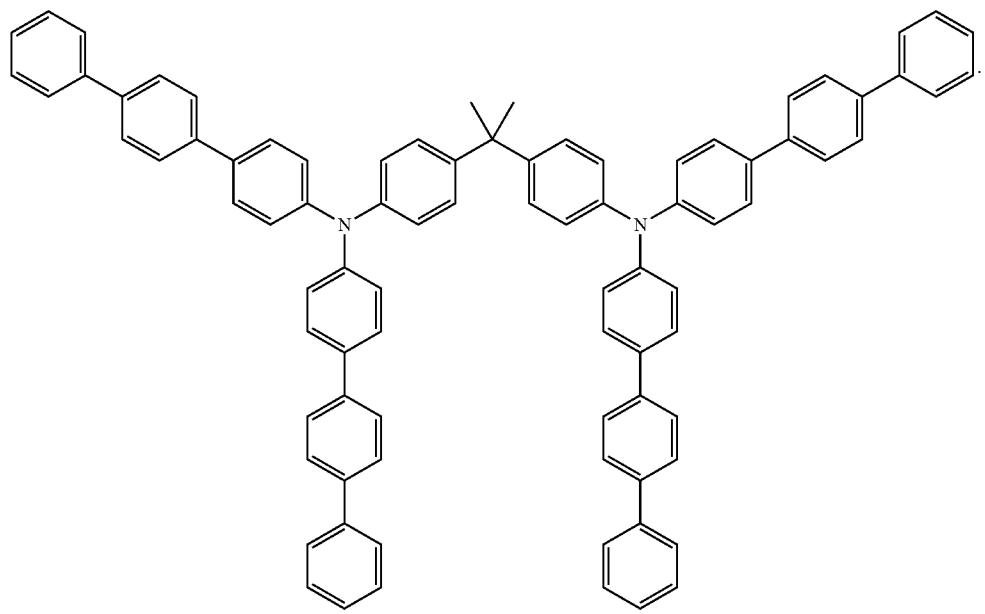 [SMILES: CC(C)(c1ccc(N(c2ccc(-c3ccc(-c4ccccc4)cc3)cc2)c2ccc(-c3ccc(-c4ccccc4)cc3)cc2)cc1)c1ccc(N(c2ccc(-c3ccc(-c4ccccc4)cc3)cc2)c2ccc(-c3ccc(-c4ccccc4)cc3)cc2)cc1]

COMPARATIVE EXAMPLE 17

An organic light emitting device was manufactured in the same manner as in Example 20 except that the following HT14 was used instead of Compound 1 as the second hole transfer layer.

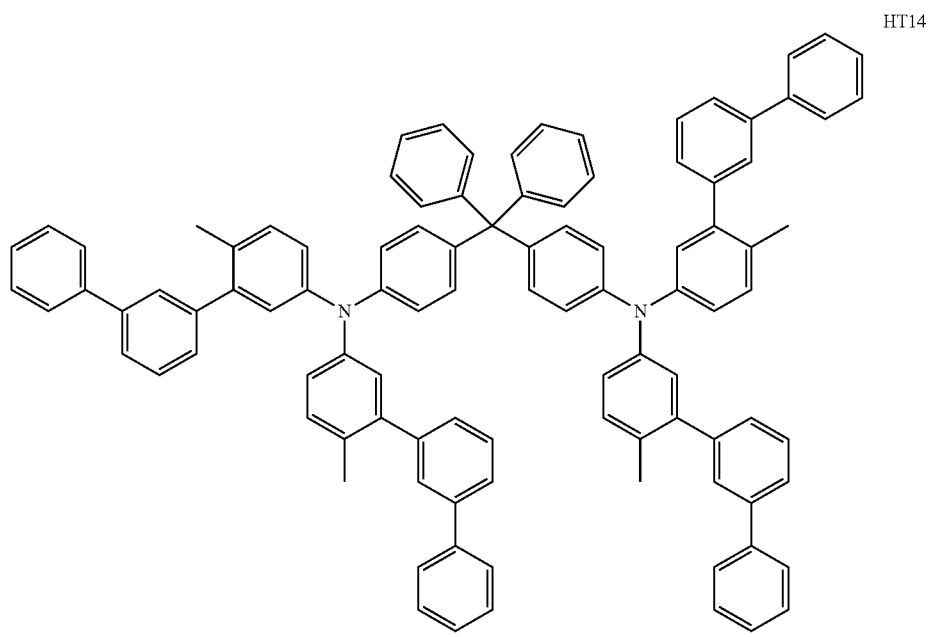 [SMILES: Cc1ccc(N(c2ccc(C(c3ccccc3)(c3ccccc3)c3ccc(N(c4ccc(C)c(-c5cccc(-c6ccccc6)c5)c4)c4ccc(C)c(-c5cccc(-c6ccccc6)c5)c4)cc3)cc2)c2ccc(C)c(-c3cccc(-c4ccccc4)c3)c2)cc1-c1cccc(-c2ccccc2)c1]

COMPARATIVE EXAMPLE 18

An organic light emitting device was manufactured in the same manner as in Example 20 except that the following HT15 was used instead of Compound 1 as the second hole transfer layer.

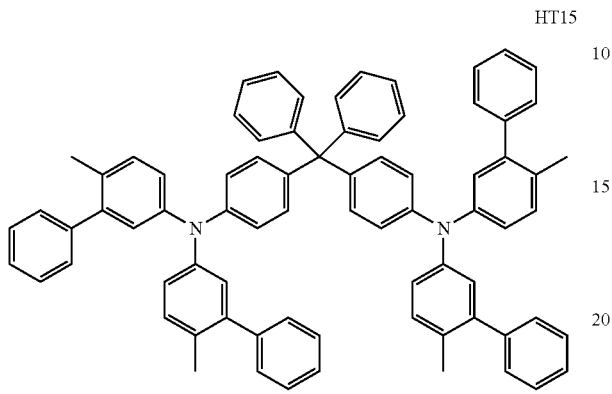

HT15

Results of experimenting with the blue organic light emitting devices of Examples 20 to 30 and Comparatives Examples to 18 are shown in Table 2.

TABLE 2

| Experimental Example 10 mA/cm² | Second Hole Transfer Layer | Electron Transfer Layer (+LiQ) | Voltage (V) | Efficiency (Cd/A) | Color Coordinate (x, y) | Lifetime (T80, h) (@1000 nit) |
|---|---|---|---|---|---|---|
| Example 20 | Compound 1 | ET1 | 4.67 | 6.71 | (0.135, 0.138) | 11234.0 |
| Example 21 | Compound 3 | ET1 | 4.72 | 6.63 | (0.134, 0.137) | 10823.0 |
| Example 22 | Compound 4 | ET1 | 4.62 | 6.58 | (0.135, 0.138) | 12482.0 |
| Example 23 | Compound 7 | ET1 | 4.68 | 6.82 | (0.134, 0.138) | 10547.0 |
| Example 24 | Compound 9 | ET1 | 4.59 | 6.72 | (0.136, 0.139) | 11057.0 |
| Example 25 | Compound 11 | ET1 | 4.61 | 6.52 | (0.135, 0.138) | 12034.0 |
| Example 26 | Compound 12 | ET1 | 4.57 | 6.69 | (0.133, 0.139) | 10258.0 |
| Example 27 | Compound 1 | ET3 | 4.66 | 6.78 | (0.135, 0.138) | 10348.0 |
| Example 28 | Compound 8 | ET5 | 4.72 | 6.58 | (0.134, 0.138) | 10544.0 |
| Example 29 | Compound 13 (Crosslinked) | ET5 (Alone) | 4.92 | 6.67 | (0.136, 0.139) | 9752.0 |
| Example 30 | Compound 12 | ET1/ET5 | 4.95 | 6.94 | (0.136, 0.139) | 13200.0 |
| Comparative Example 10 | HT1 | ET5 | 5.67 | 5.12 | (0.136, 0.139) | 7200 |
| Comparative Example 11 | HT2 | ET2/ET4 | 5.88 | 5.88 | (0.135, 0.138) | 7893 |
| Comparative Example 12 | HT9 | E1 | 8.11 | 4.51 | (0.135, 0.138) | 7893 |
| Comparative Example 13 | HT10 | E1 | 11.8 | 2.01 | (0.135, 0.138) | 1102 |
| Comparative Example 14 | HT11 | E1 | 10.5 | 2.33 | (0.135, 0.138) | 1208 |
| Comparative Example 15 | HT12 | E1 | 8.14 | 4.44 | (0.135, 0.138) | 7893 |
| Comparative Example 16 | HT13 | E1 | 10.23 | 4.23 | (0.135, 0.138) | 7893 |
| Comparative Example 17 | HT14 | E1 | 5.68 | 5.90 | (0.135, 0.138) | 9023 |
| Comparative Example 18 | HT15 | E1 | 6.12 | 6.00 | (0.135, 0.138) | 8102 |

Examples 20 to 30 and Comparative Examples 10 to 18 of Table 2 are results of a hybrid device in which the hole transfer layer and the light emitting layer were prepared using a solution process, and the electron transfer layer was in prepared using a deposition process.

The hole transfer layer presented in the present specification may be used in contact with the anode. In the examples, the device was formed with first and second hole transfer layers, and as the first hole transfer layer, widely known poly(3,4-ethylenedioxythiophene)-polystyrene sulfonate (PEDOT/PSS, manufactured by Bayer AG, Baytron P Al 4083) was used, and the results of Tables 1 and 2 are results of maximizing device performance by forming the second hole transfer layer (also referred to as buffer layer) between the first hole transfer layer and the light emitting layer. The electron transfer layer may also be formed in a plurality of layers as well as the hole transfer layer.

The hole transfer layer of the present specification is formed with a compound or polymer having Chemical Formula 1, or crosslinking of the compound or crosslinking of the polymer, and may be incorporated into a device manufactured using any of them. In the results of Tables 1 and 2, performance of the blue organic electroluminescent device was more superior compared to existing general hole transfer layers of a solution process. Particularly, this document showed that combinations with azine-based compounds and phosphine oxide-based compounds widely known as an electron transfer layer for deposition were more superior.

In addition, it was identified that the compound of the present specification was effective in terms of voltage, efficiency and lifetime when used in a hole transfer layer compared to the compounds of Comparative Examples 3 to 6 and 15 having a molecular weight of less than 1000 g/mol.

When comparing the compound of Comparative Example 8 in which Ar1 to Ar4 are heteroaryl with the compound of the present disclosure in which Ar1 to Ar2 are aryl, it was identified that the compound having Ar1 and Ar2 according to the present specification was effective in terms of voltage, efficiency and lifetime.

In addition, it was identified that Comparative Examples 13 to 15 using compounds different from R1 and R2 according to the present specification had higher voltage, lower efficiency and shorter lifetime compared to the organic light emitting device using the compound of the present specification. Particularly, it was seen that HT11, the compound of Comparative Example 14, had the highest occupied molecular orbital (HOMO) energy and thereby was not suitable as a hole transfer layer.

By the result of Comparative Example 12, it was identified that, when an end group of the compound according to the present specification did not satisfy E1 and E2, effects were reduced in terms of voltage, efficiency and lifetime compared to the compound of the present specification.

The compound of Comparative Example 16 is a compound in which L1 to L6 and Ar1 to Ar4 of the present specification are all unsubstituted, and it was seen that effects were reduced compared to the compound in which L1 to L6 and Ar1 to Ar4 of the present specification are substituted with at least one of an alkyl group, a cycloalkyl group or an adamantyl group.

The compounds of Comparative Examples 17 and 18 are compounds in which R1 and R2 of the present specification are a phenyl group and when n is 1, Ar1 to Ar4 are an unsubstituted phenyl group, and it was identified that effects were reduced compared to the compound in which R1 and R2 of the present specification are a phenyl group and when n is 1, Ar1 to Ar4 are a phenyl group substituted with an alkyl group or an alkenyl group, or a polycyclic aryl group.

The invention claimed is:
1. A compound of Chemical Formula 1, and having a molecular weight greater than or equal to 1,000 g/mol:

[Chemical Formula 1]

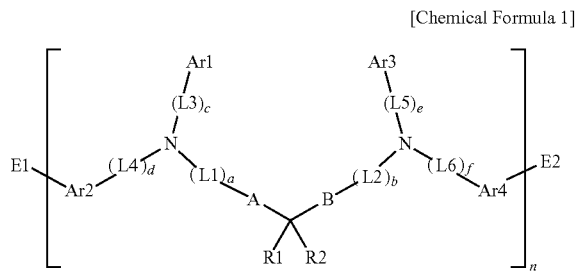

wherein, in Chemical Formula 1:
R1 and R2 are the same as each other, and are hydrogen, deuterium, an alkyl group having 1 to 15 carbon atoms, or an aryl group having 6 to 10 carbon atoms, or bond to each other to form a cycloalkyl group;
A and B are the same as each other, and are a substituted or unsubstituted phenylene group;
L1 and L2 are the same as each other, L3 and L5 are the same as each other, L4 and L6 are the same as each other, and L1 to L6 are a substituted or unsubstituted arylene group;
Ar2 and Ar4 are the same as each other, and a substituted or unsubstituted arylene group;
Ar1 and Ar3 are the same as each other, and are a substituted or unsubstituted aryl group;
at least one of L1, L2, L4, L6, Ar2 and Ar4 is substituted with an alkyl group, a cycloalkyl group, or an adamantyl group:
at least one of L3 and L5 is substituted with a cycloalkyl group or an adamantyl group:
at least one of Ar1 and Ar3 is substituted with an alkyl group or an adamantyl group:
E1 and E2 are the same as each other, and are hydrogen, deuterium, a halogen group, a substituted or unsubstituted alkyl group, a substituted or unsubstituted aryl group, or a substituted or unsubstituted siloxane group:
a and b are an integer of 1 to 5, and c to f are each an integer of 0 to 5, and when a to f are an integer of 2 to 5, linking groups in the parentheses are the same as or different from each other:
n is an integer of 1 or greater, and when n is 1, E1 and E2 are hydrogen or deuterium; and
when R1 and R2 are a phenyl group and n is 1, Ar1 and Ar3 are a phenyl group substituted with an alkyl group or an alkenyl group, or a substituted or unsubstituted polycyclic aryl group; and Ar2 and Ar4 are a phenylene group substituted with an alkyl group or an alkenyl group: or a substituted or unsubstituted polycyclic arylene group.

2. The compound of claim 1, which is 1% to 100% deuterated.

3. The compound of claim 1, wherein R1 and R2 are a linear or branched alkyl group having 1 to 10 carbon atoms, or an aryl group having 6 to 10 carbon atoms, or bond to each other to form a cycloalkyl group having 4 to 8 carbon atoms.

4. The compound of claim 1, wherein at least one of L1 to L6 and Ar1 to Ar4 is substituted with a linear or branched alkyl group having 1 to 10 carbon atoms, a cycloalkyl group, or an adamantyl group.

5. The compound of claim 1, wherein Ar1 and Ar3 are a substituted or unsubstituted phenyl group, a substituted or unsubstituted biphenyl group, a substituted or unsubstituted terphenyl group, a substituted or unsubstituted naphthyl group, a substituted or unsubstituted phenanthrene group, a substituted or unsubstituted triphenylene group, a substituted or unsubstituted chrysenyl group, or a substituted or unsubstituted fluorene group.

6. The compound of claim 1, wherein Ar2 and Ar4 are a substituted or unsubstituted phenylene group, a substituted or unsubstituted biphenylylene group, a substituted or unsubstituted terphenylylene group, a substituted or unsubstituted naphthylene group, a substituted or unsubstituted divalent phenanthrene group, a substituted or unsubstituted divalent triphenylene group, a substituted or unsubstituted divalent chrysenyl group, or a substituted or unsubstituted divalent fluorene group.

7. The compound of claim 1, wherein L1, L3 and L4 are the same as or different from each other, and are each independently a substituted or unsubstituted phenylene group, a substituted or unsubstituted biphenylylene group, a substituted or unsubstituted terphenylylene group, a substituted or unsubstituted naphthylene group, or a substituted or unsubstituted divalent fluorene group.

8. A composition comprising the compound of claim 1.

9. The composition of claim 8, which is used for an organic light emitting device.

10. An organic light emitting device comprising:
   a first electrode;
   a second electrode provided to face the first electrode; and
   an organic material layer having one or more layers provided between the first electrode and the second electrode,
   wherein one or more layers of the organic material layer include the composition of claim 8 or a cured material thereof.

11. The organic light emitting device of claim 10, wherein the organic material layer including the composition or a cured material thereof is a hole transfer layer, a hole injection layer, or a layer carrying out hole transfer and hole injection at the same time.

12. The organic light emitting device of claim 10, wherein the organic material layer includes a light emitting layer, and the light emitting layer includes a fluorescent dopant or a phosphorescent dopant.

13. The organic light emitting device of claim 12, wherein the light emitting layer includes a phosphorescent dopant, and the phosphorescent dopant is a metal complex.

14. The organic light emitting device of claim 12, wherein the light emitting layer includes a fluorescent dopant, and the fluorescent dopant is an arylamine compound including an anthracene group or a chrysene group.

15. The organic light emitting device of claim 10, wherein the organic material layer includes an electron transfer layer, and the electron transfer layer includes a compound represented by the following Chemical Formula 2 or 3:

[Chemical Formula 2]

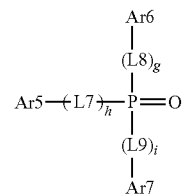

[Chemical Formula 3]

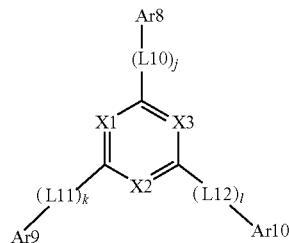

wherein in Chemical Formulae 2 and 3,
at least two of X1 to X3 are N, and the remaining one is CR,
R is hydrogen; deuterium; a halogen group; a substituted or unsubstituted alkyl group; or a substituted or unsubstituted aryl group,
L7 to L12 are the same as or different from each other, and are each independently a direct bond; a substituted or unsubstituted alkylene group; a substituted or unsubstituted divalent cycloalkyl group; a substituted or unsubstituted arylene group; or a substituted or unsubstituted divalent heteroaryl group,
Ar5 to Ar10 are the same as or different from each other, and are each independently hydrogen; deuterium; a substituted or unsubstituted alkyl group; a substituted or unsubstituted cycloalkyl group; a substituted or unsubstituted aryl group; or a substituted or unsubstituted heteroaryl group, and
g to l are each an integer of 0 to 5, and when g to l are 2 to 5, linking groups in the parentheses are the same as or different from each other.

16. The organic light emitting device of claim 10, which has a maximum light emission peak at 380 nm to 750 nm.

17. A compound of Chemical Formula 1, and having a molecular weight greater than or equal to 1,000 g/mol:

[Chemical Formula 1]

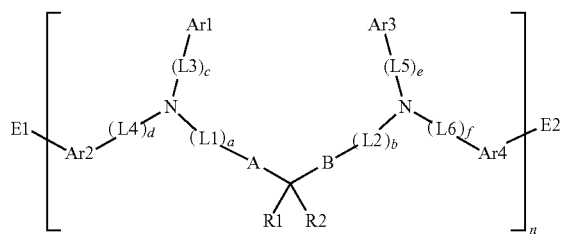

wherein, in Chemical Formula 1:
R1 and R2 are the same as each other, and are hydrogen, deuterium, an alkyl group having 1 to 15 carbon atoms, or an aryl group having 6 to 10 carbon atoms, or bond to each other to form a cycloalkyl group;

A and B are the same as each other, and are a substituted or unsubstituted phenylene group;

L1 and L2 are the same as each other, L3 and L5 are the same as each other, L4 and L6 are the same as each other, and L1 to L6 are a substituted or unsubstituted arylene group;

at least one of L1, L2, L4, L6, Ar2 and Ar4 is substituted with an alkyl group, a cycloalkyl group, or an adamantyl group;

at least one of L3 and L5 is substituted with a cycloalkyl group or an adamantyl group;

n is 1;

Ar1 and Ar3 are a phenyl group substituted with an alkyl group or an alkenyl group; or a substituted or unsubstituted polycyclic aryl group;

Ar2 and Ar4 are a phenylene group substituted with an alkyl group or an alkenyl group; or a substituted or unsubstituted polycyclic arylene group;

E1 and E2 are the same as each other, and are hydrogen or deuterium;

a and b are each an integer of 1 to 5, and c to f are each an integer of 0 to 5, and when a to f are an integer of 2 to 5, linking groups in the parentheses are the same as or different from each other.

18. A compound selected from the following structural formulae:

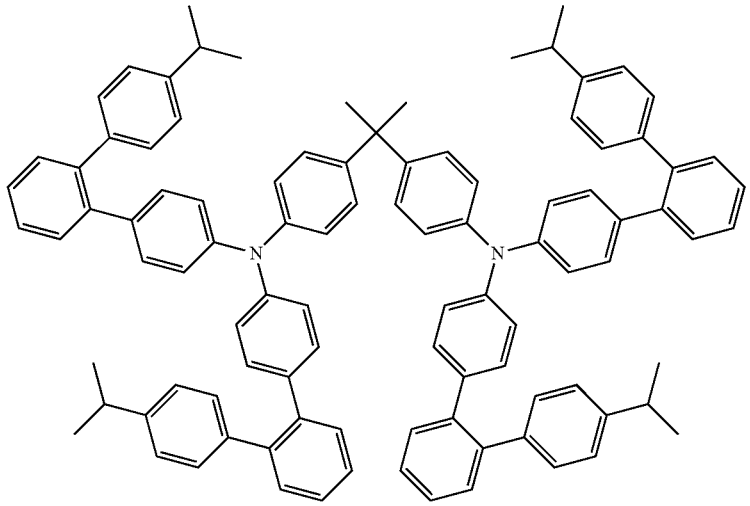

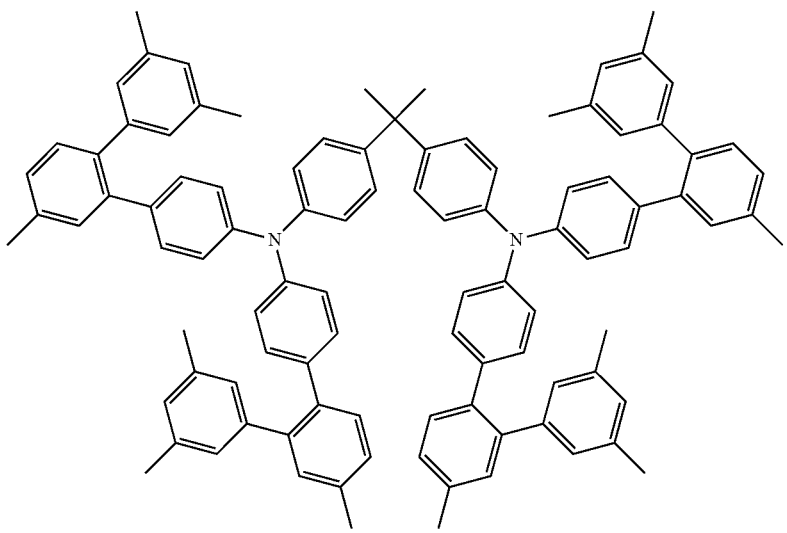

-continued
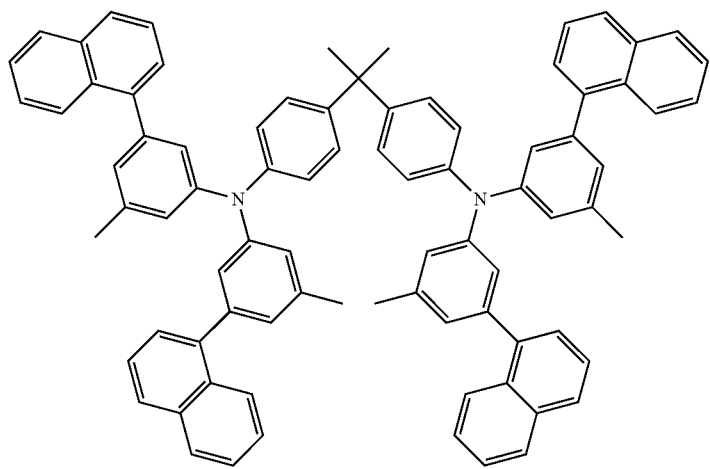

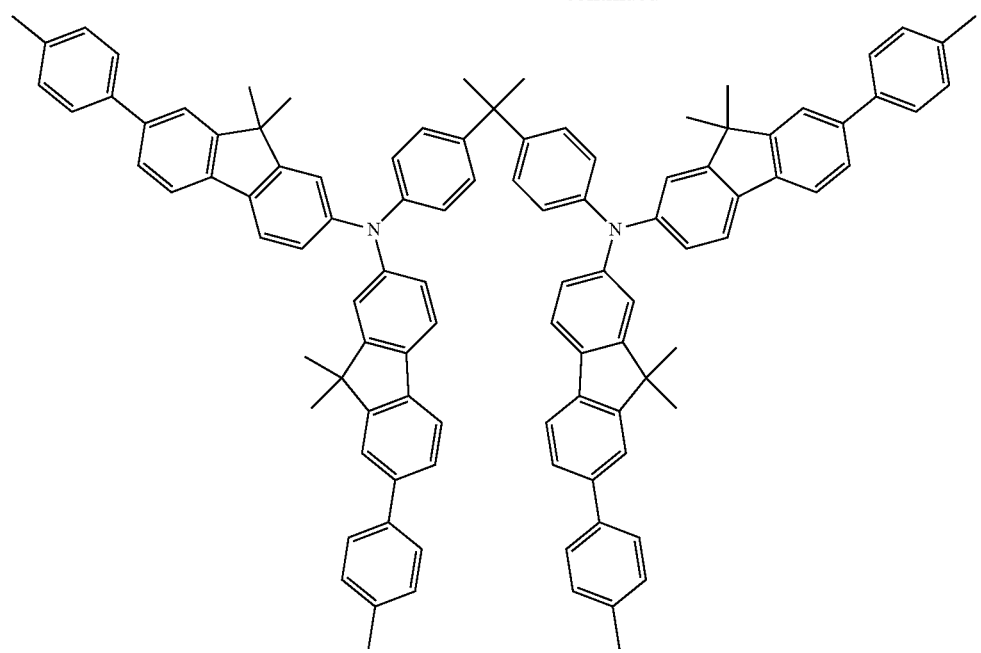
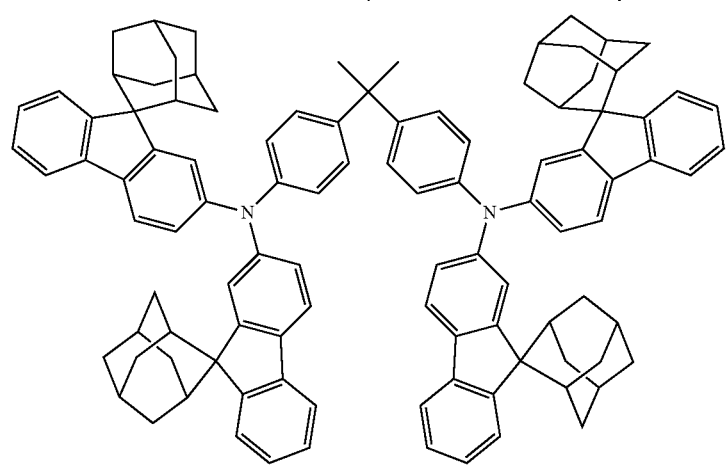
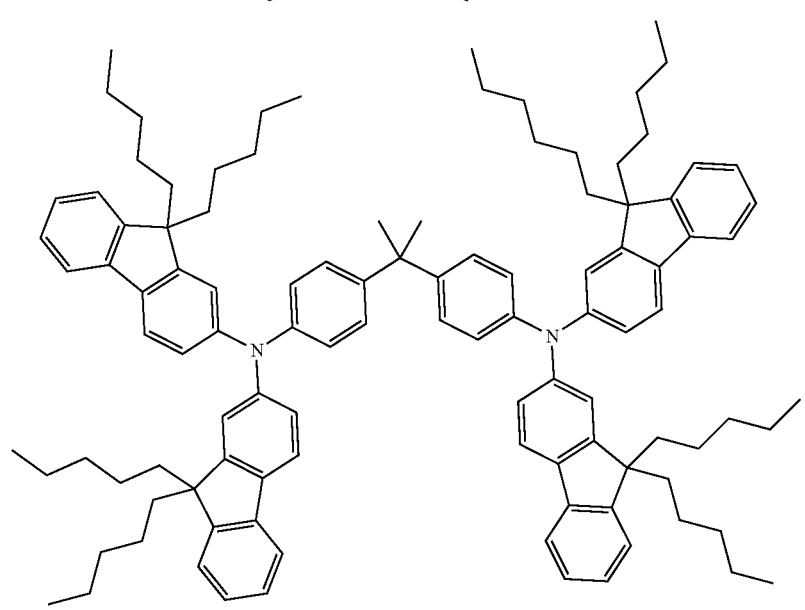

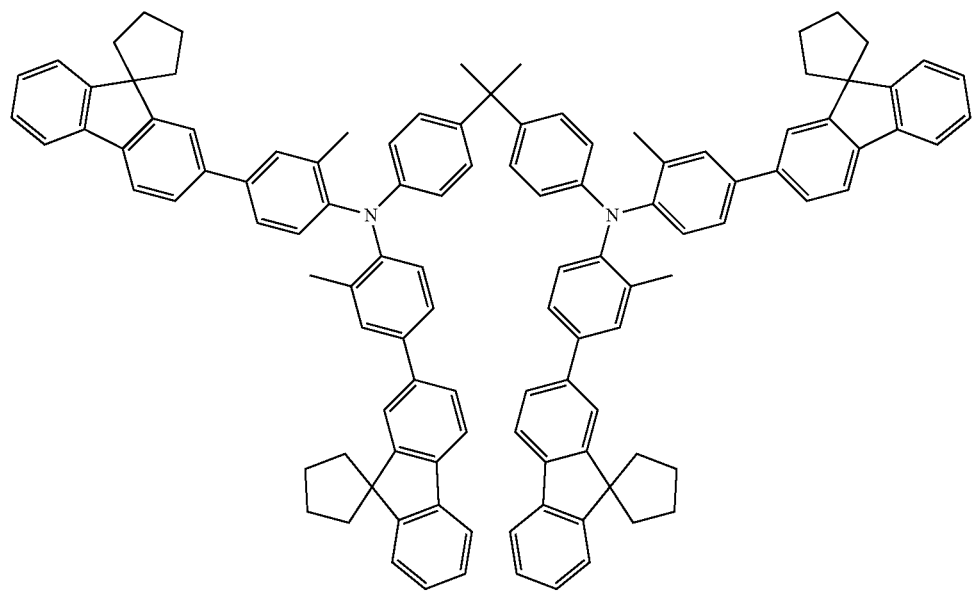
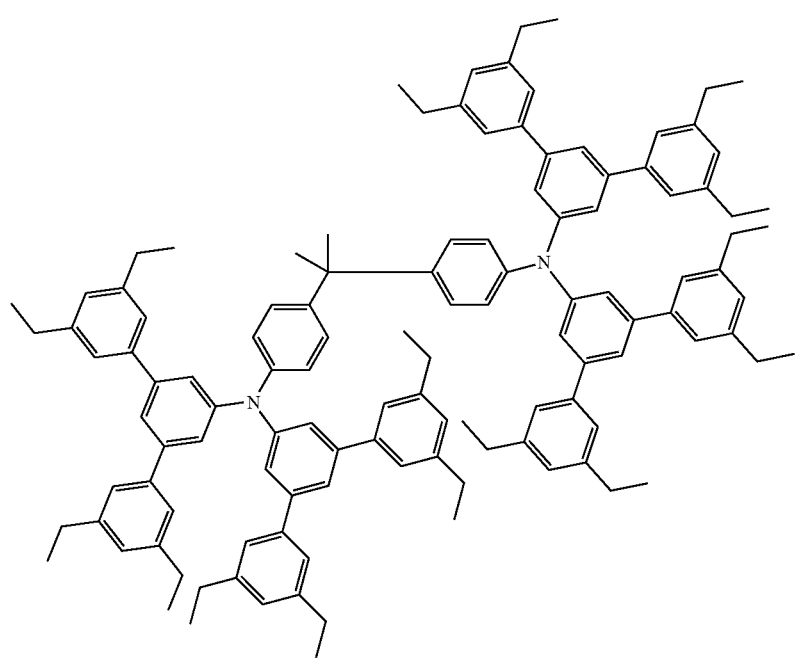

-continued
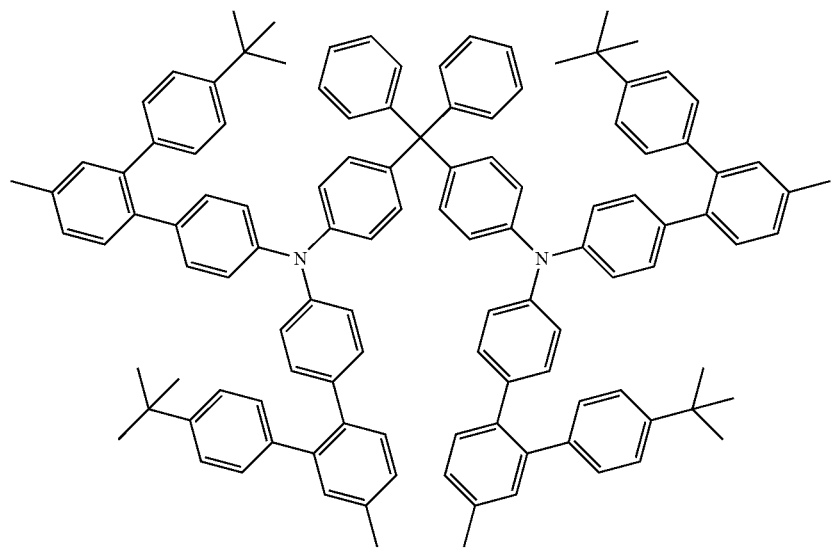
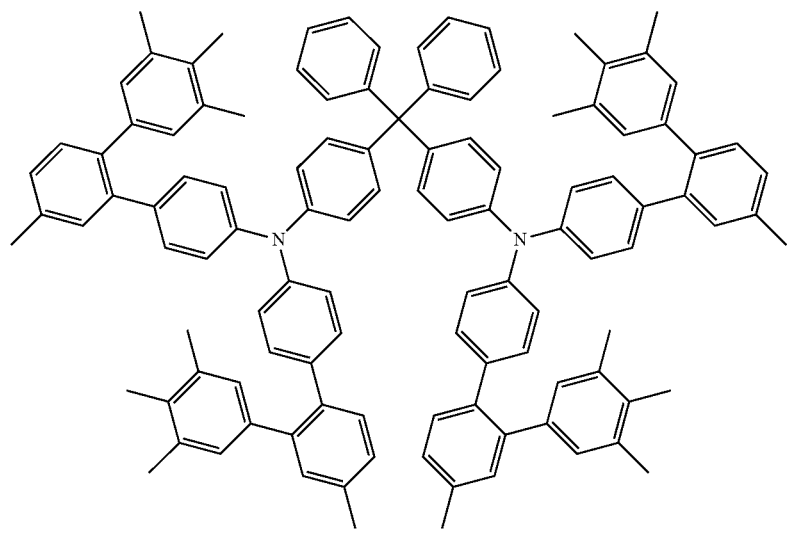
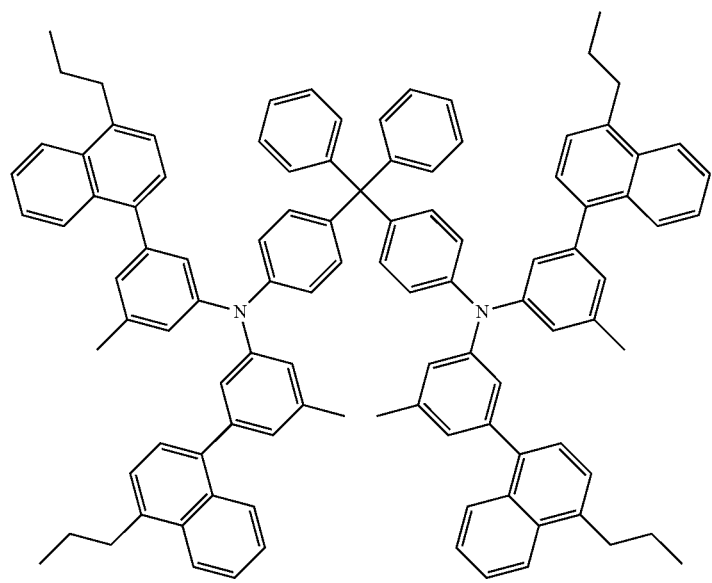

-continued
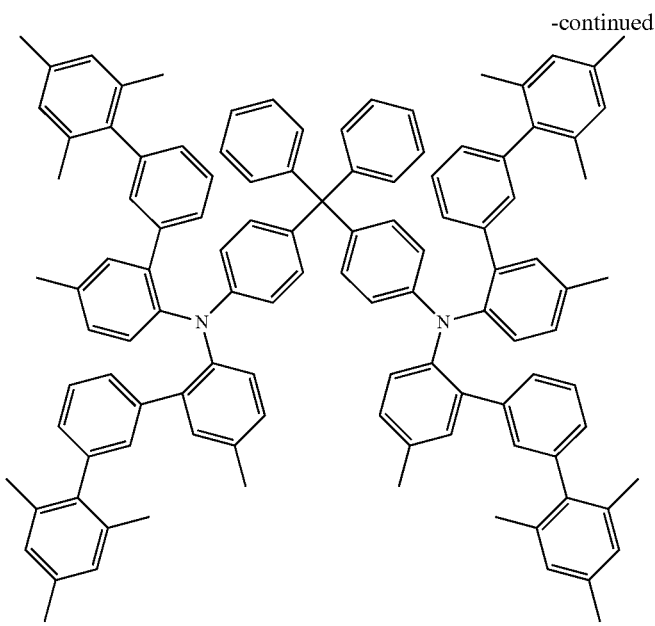
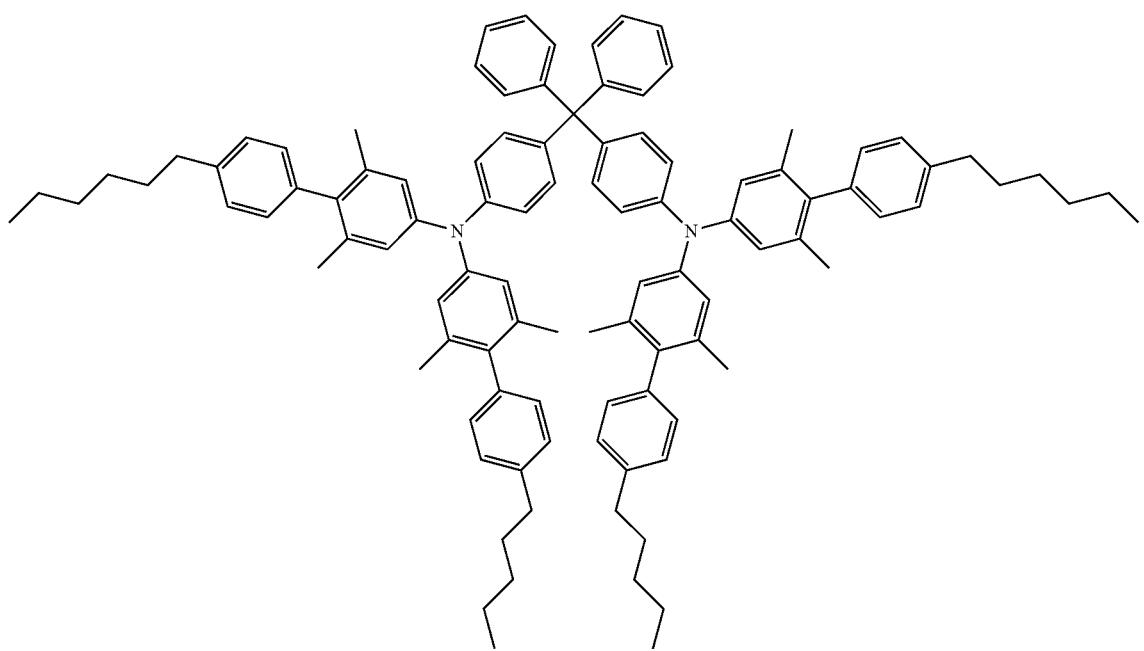

-continued
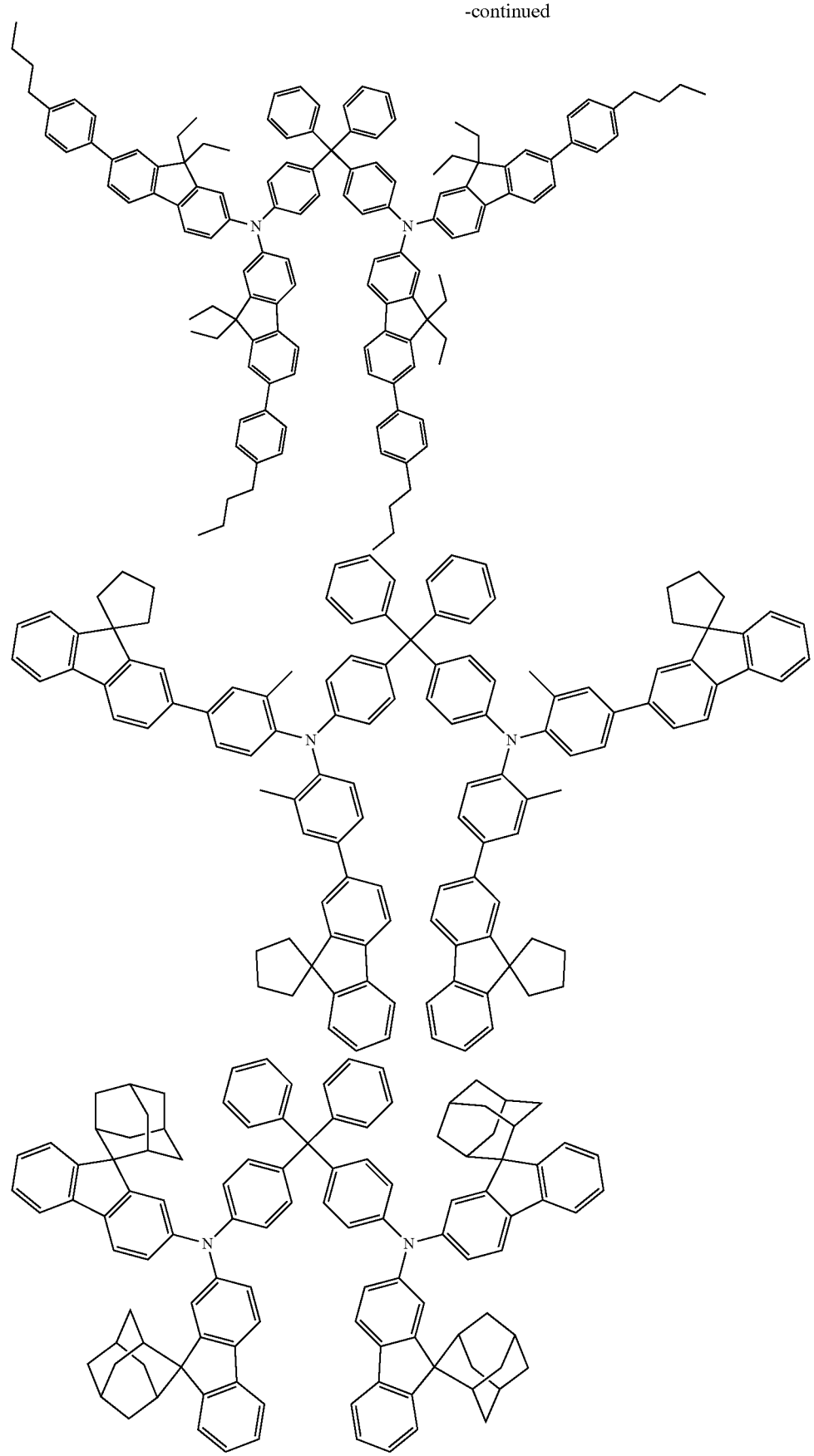

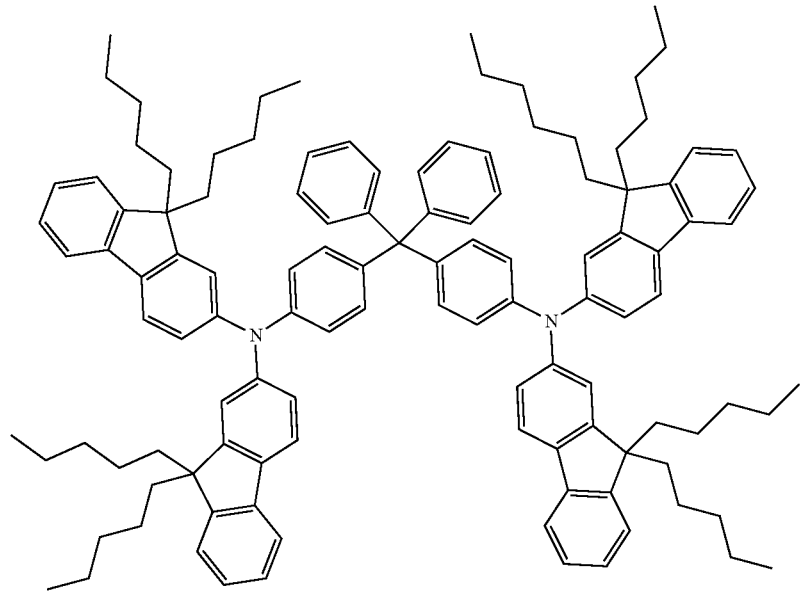
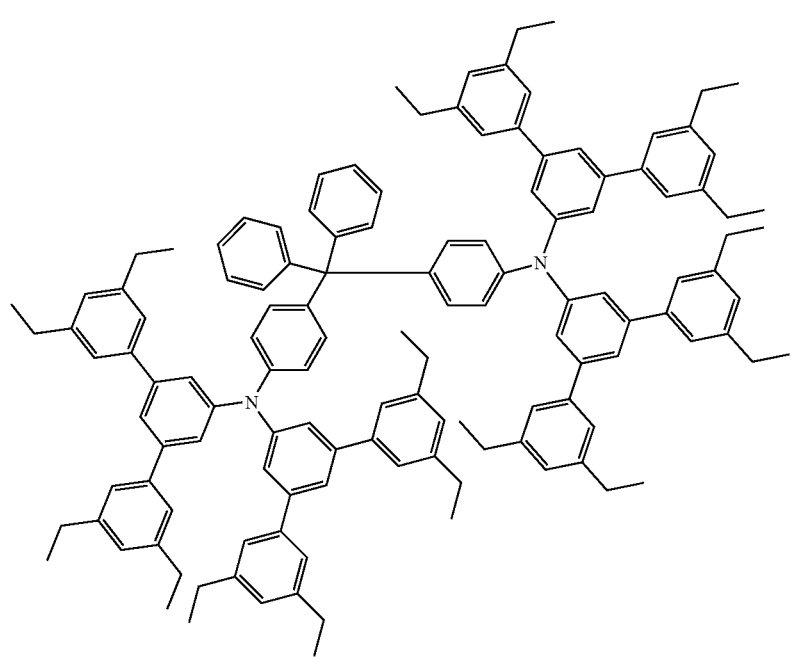

-continued
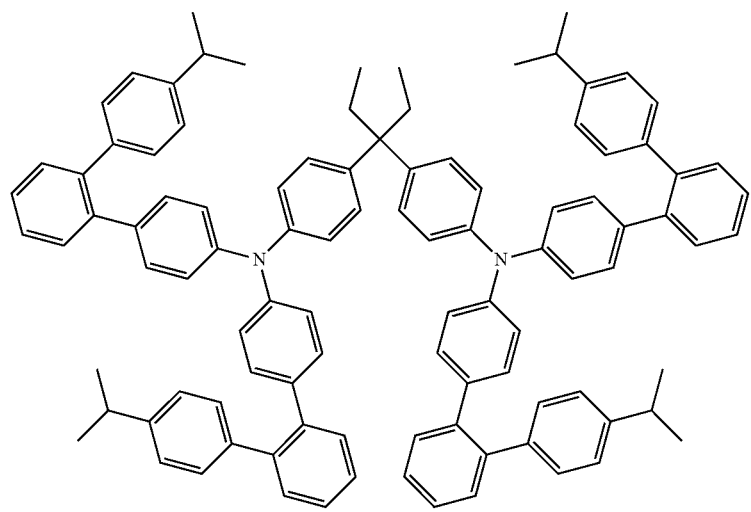
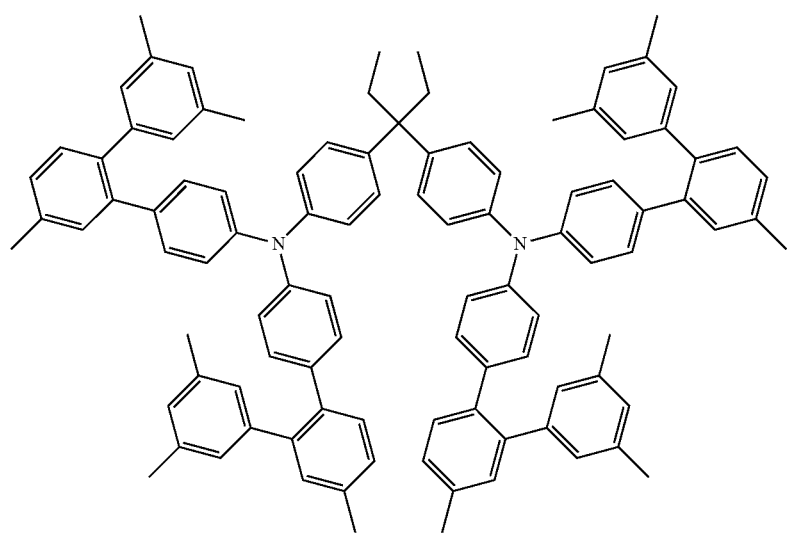
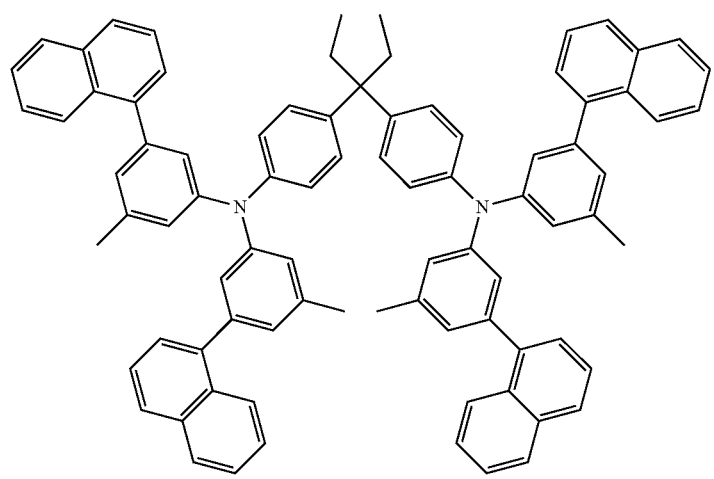

-continued
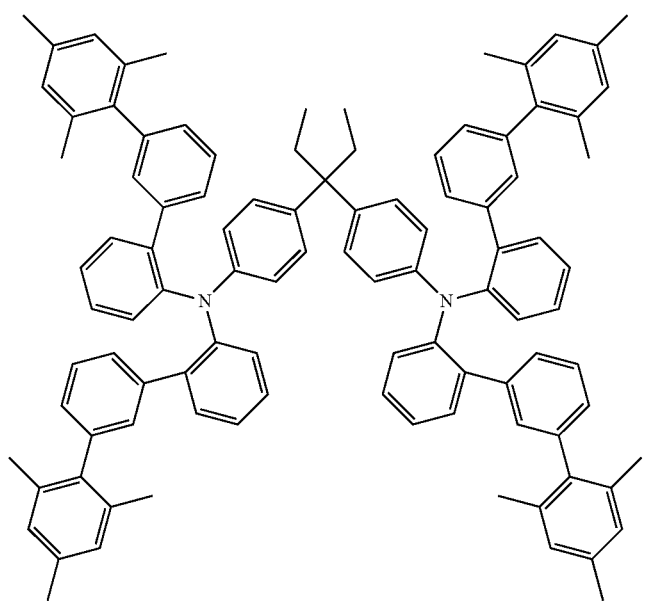
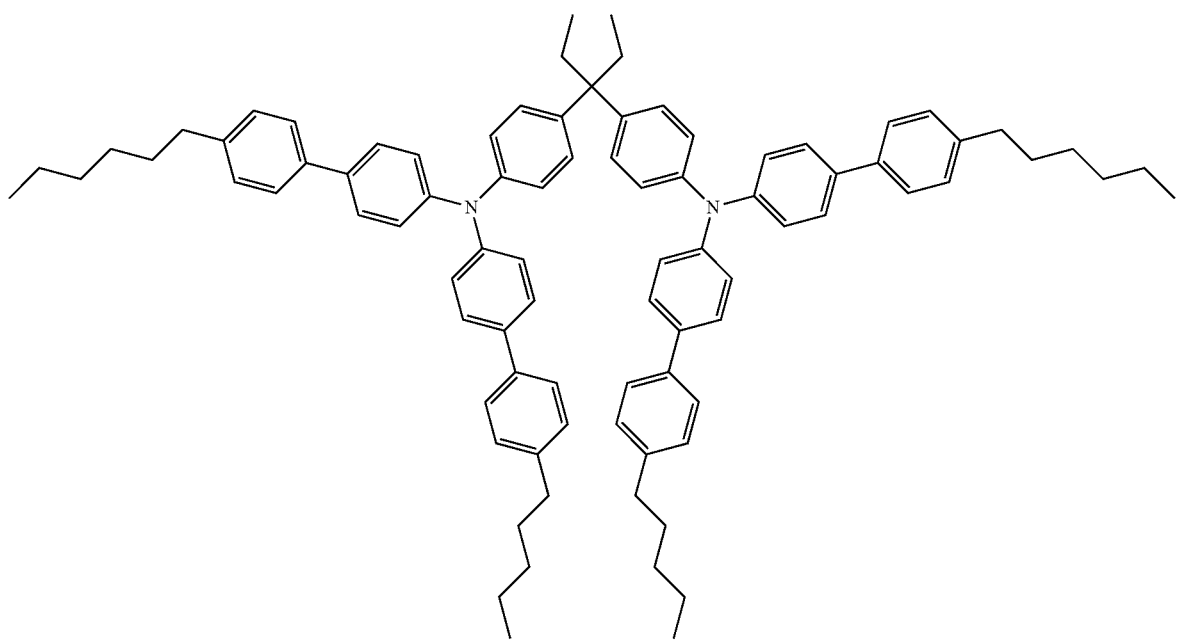

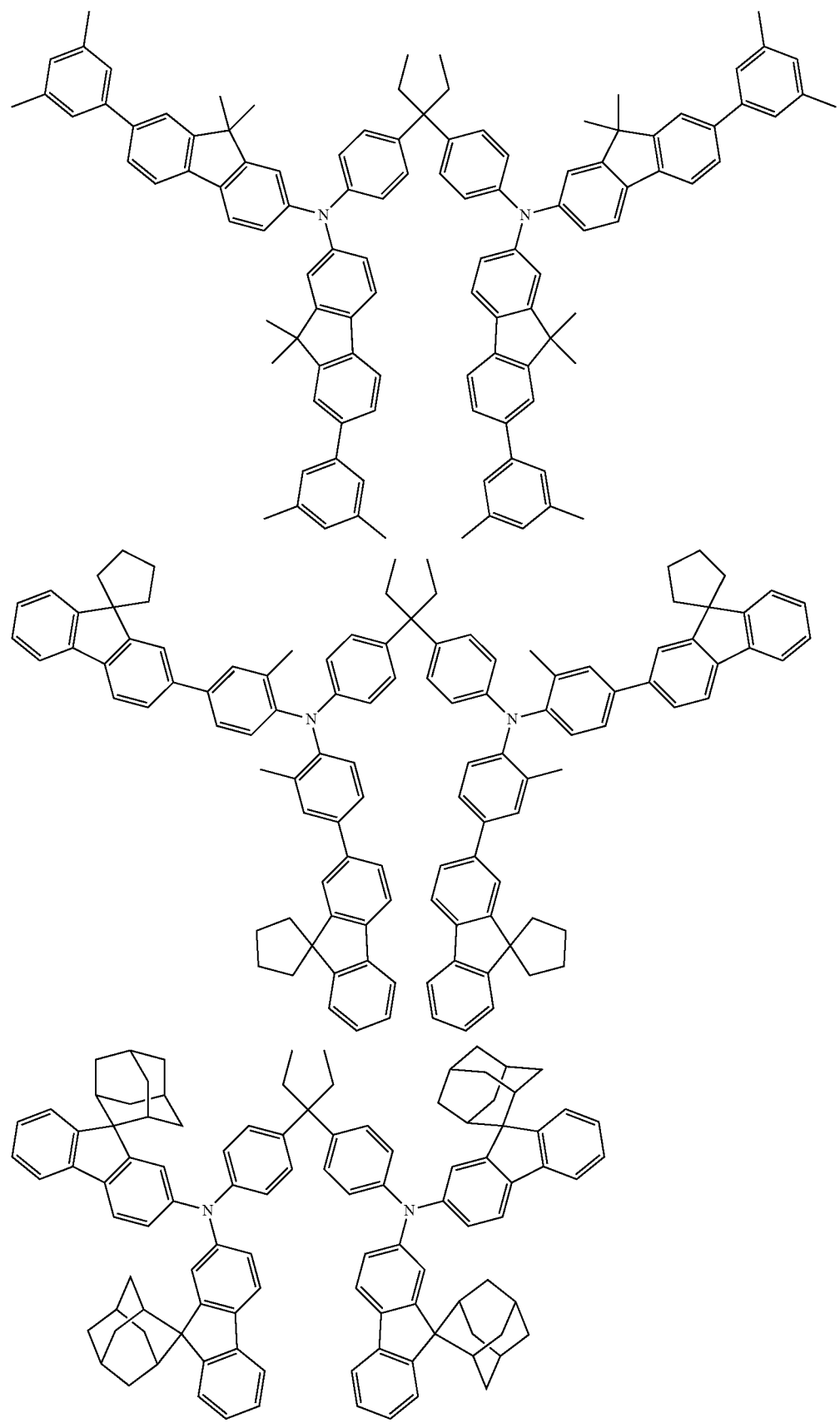

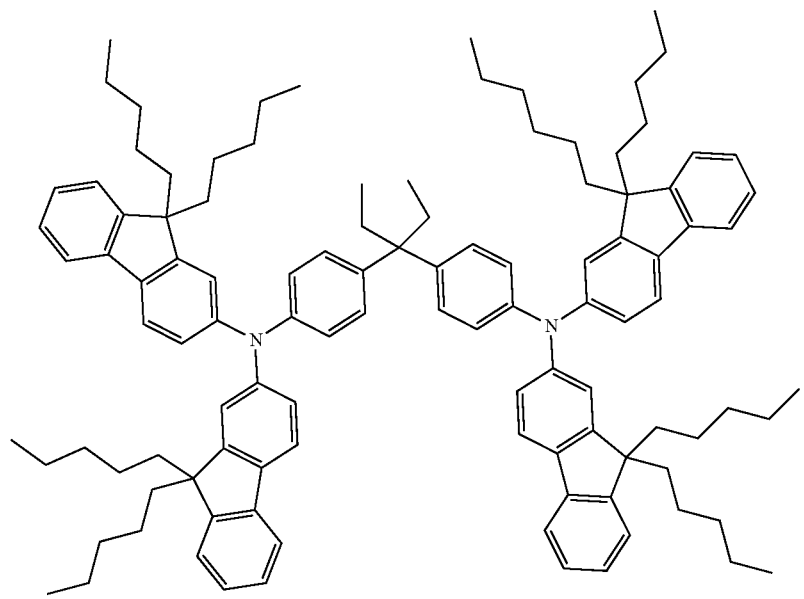
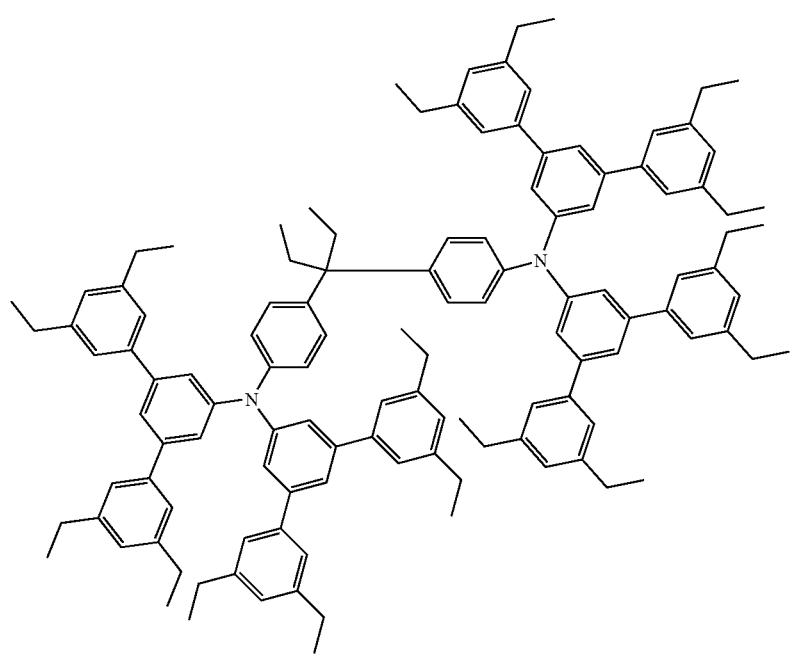

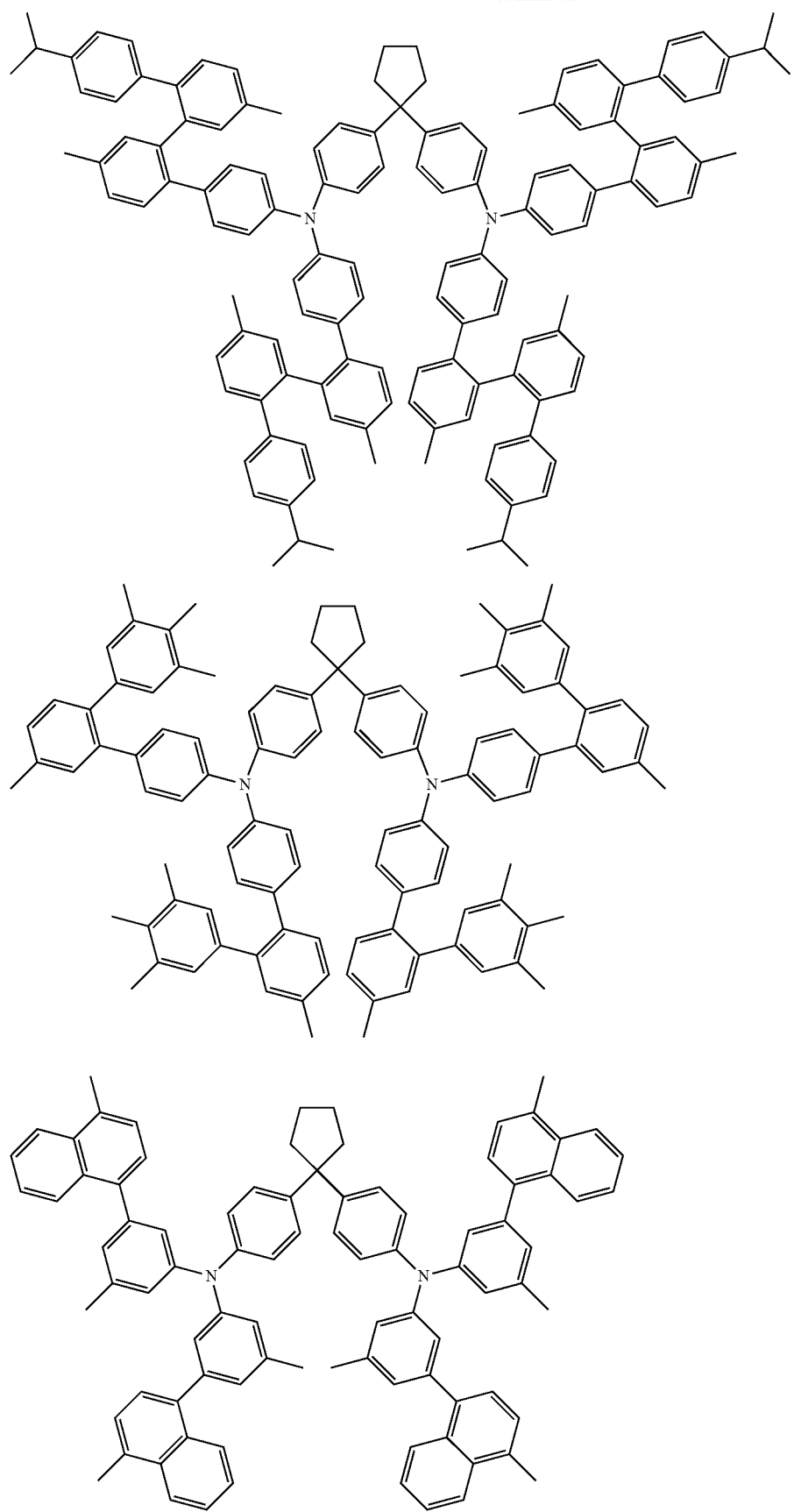

153
-continued
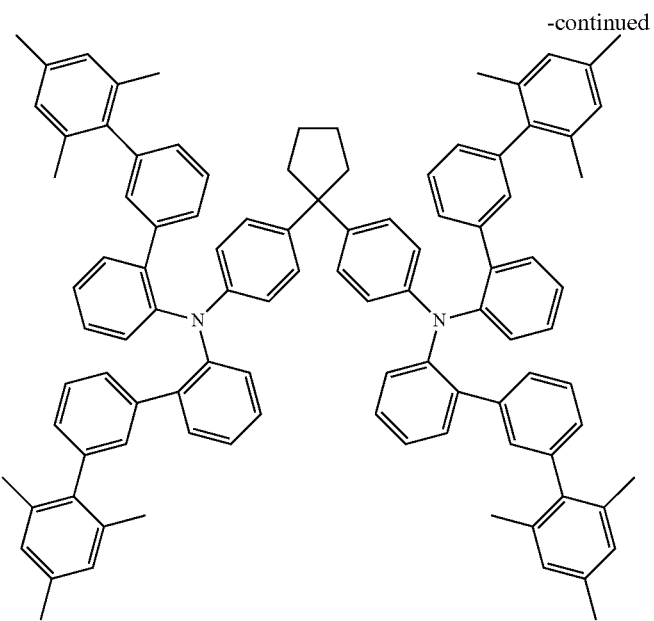
154
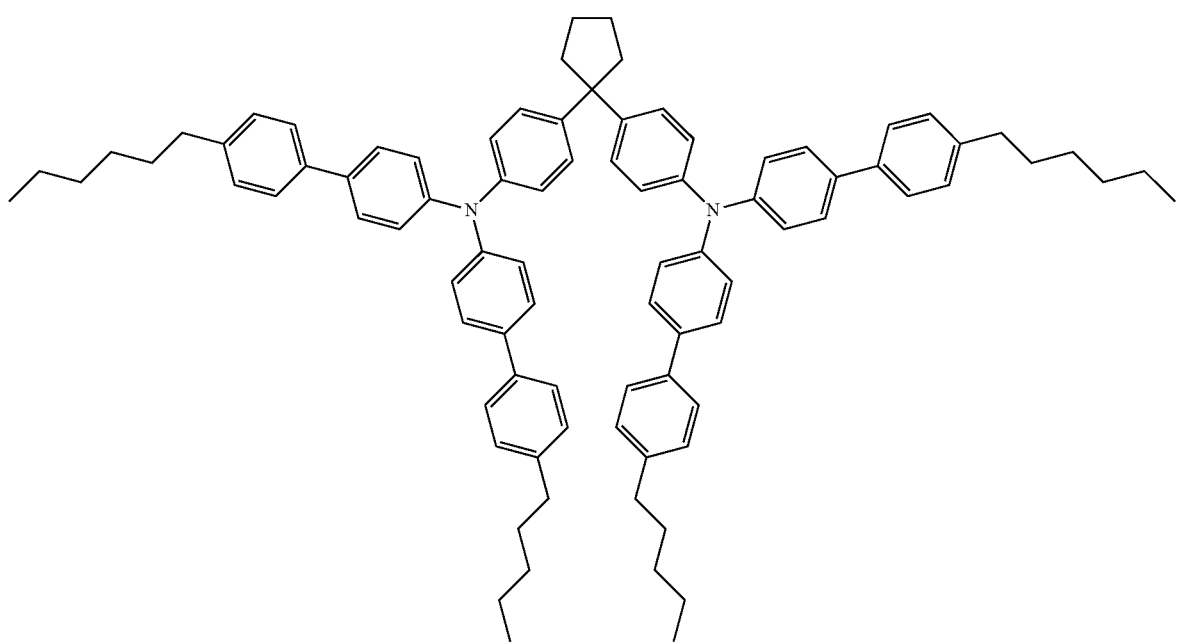

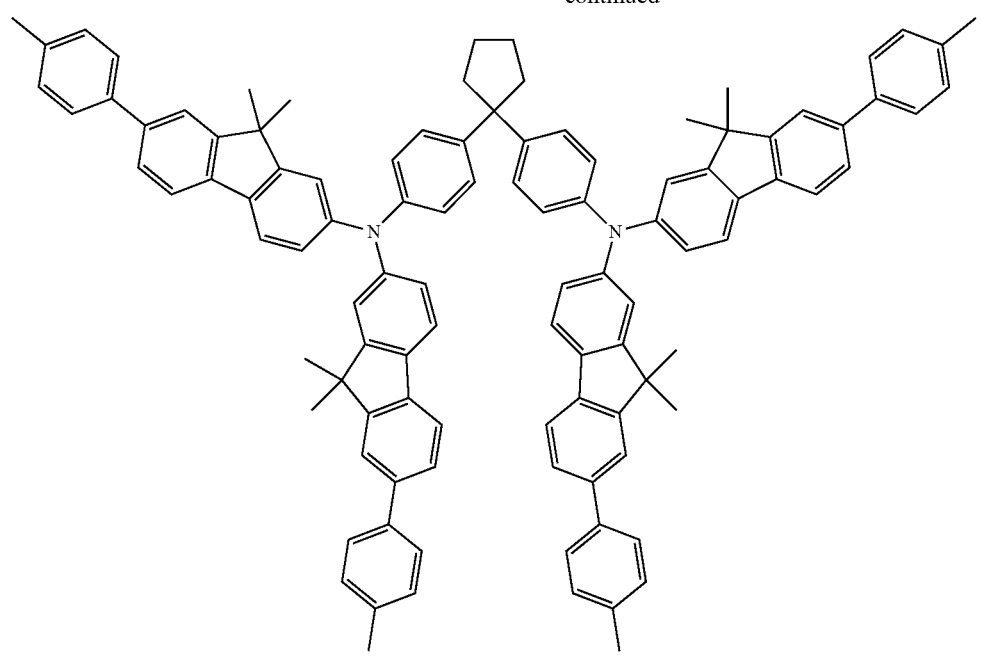
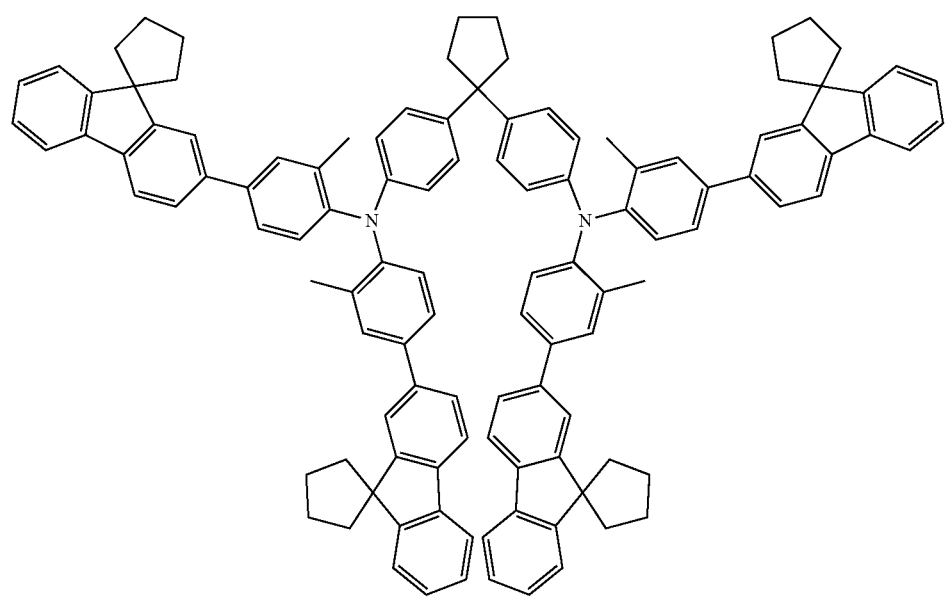
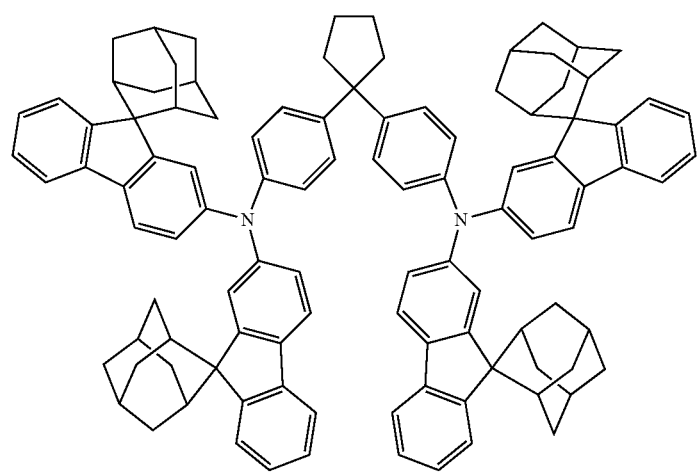

-continued
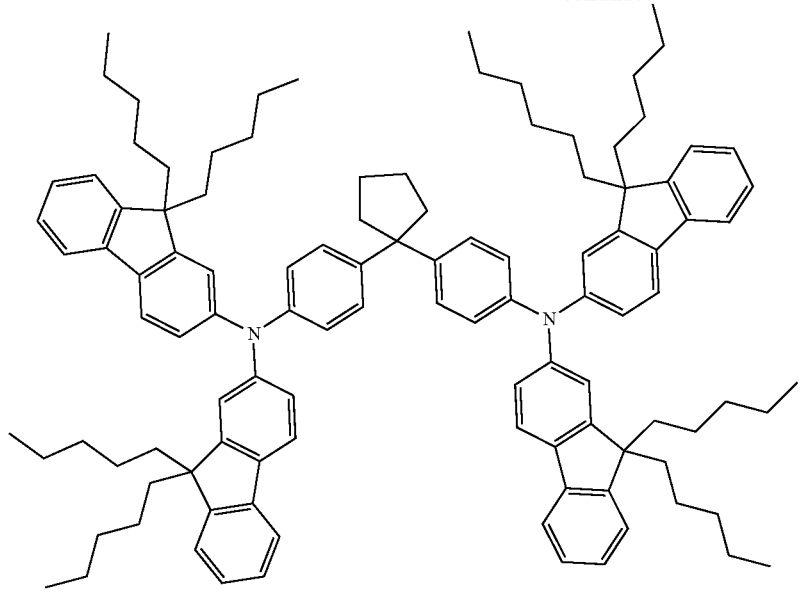
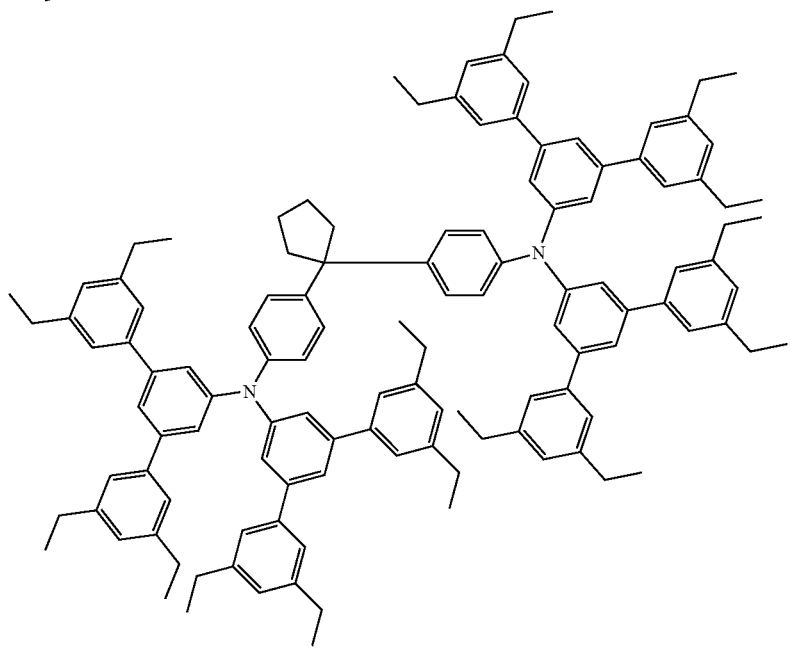
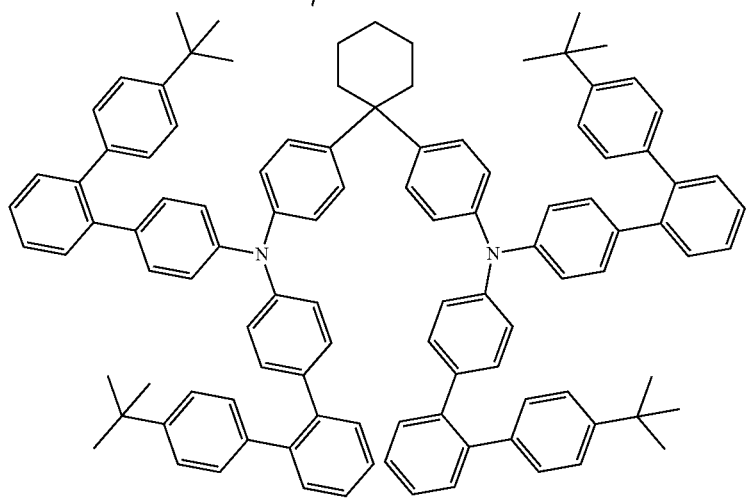

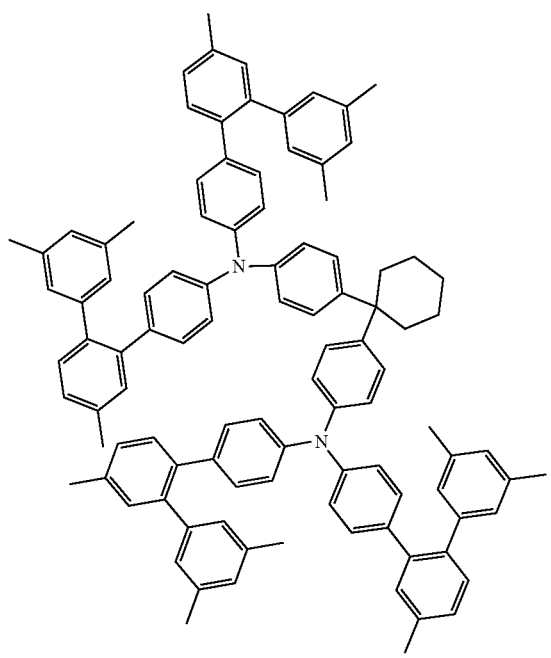
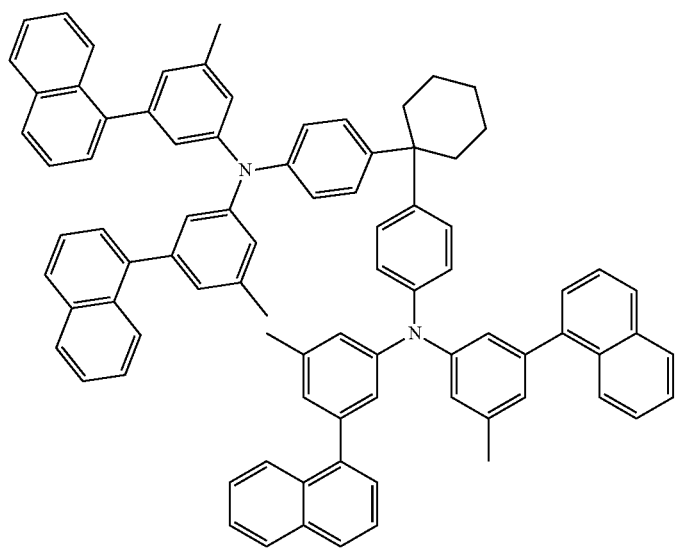

-continued
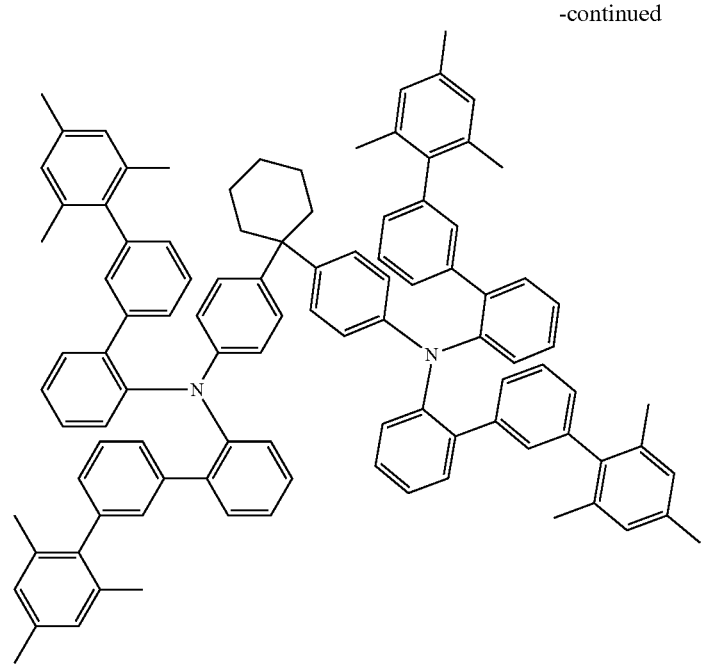
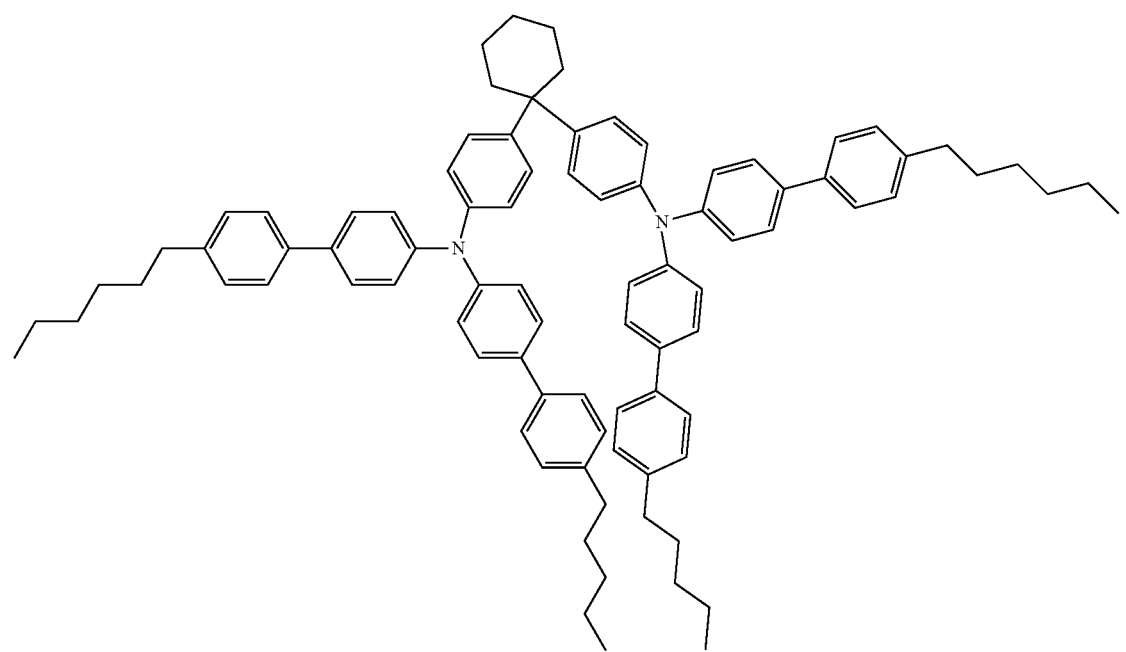

-continued
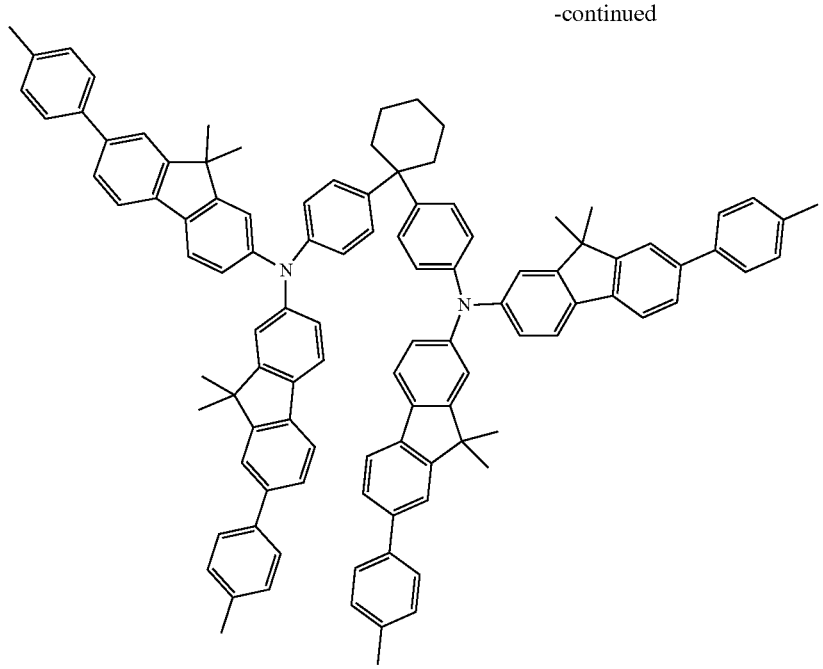
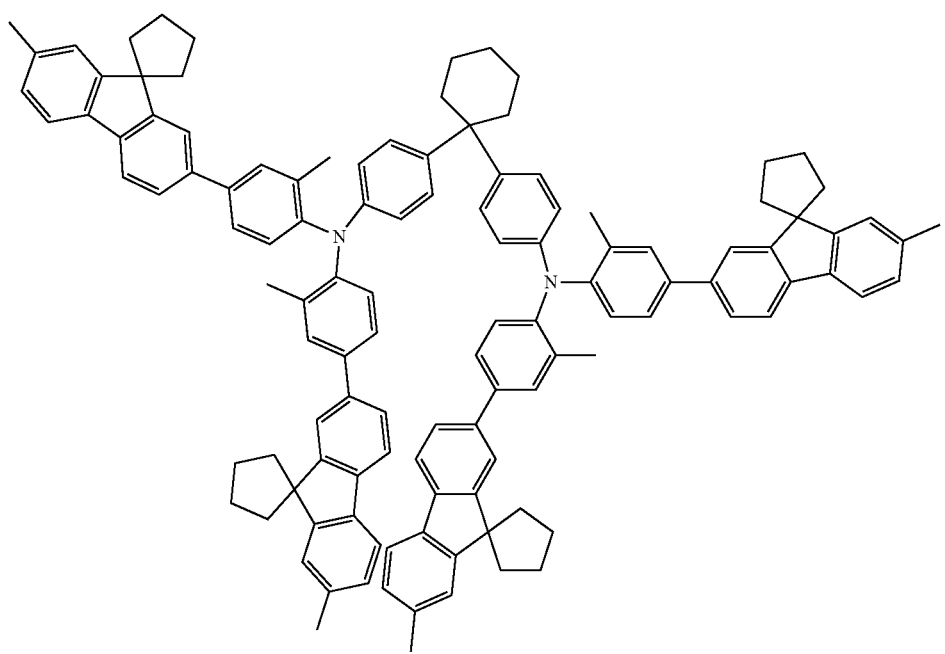

-continued
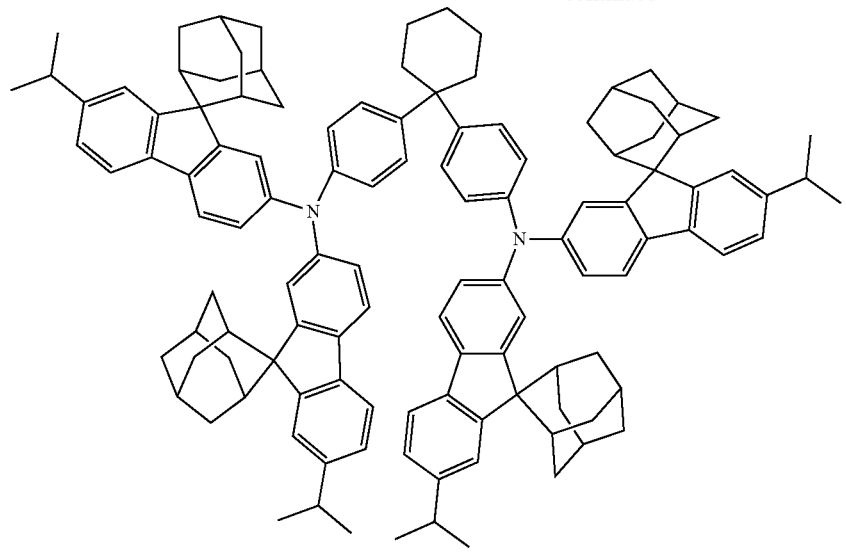
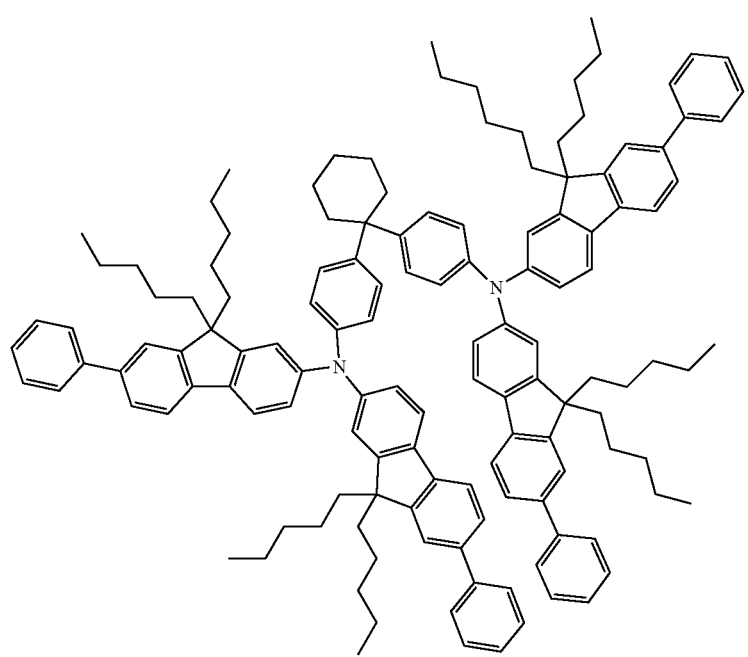

-continued
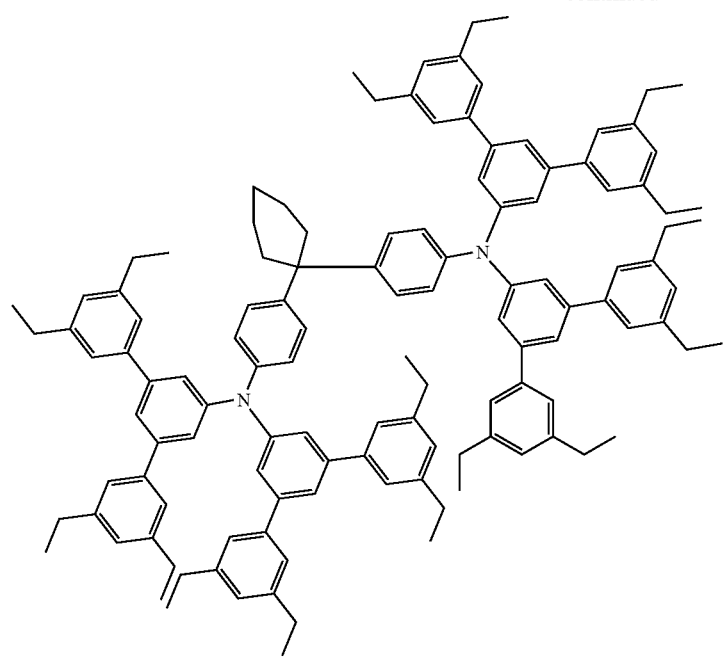
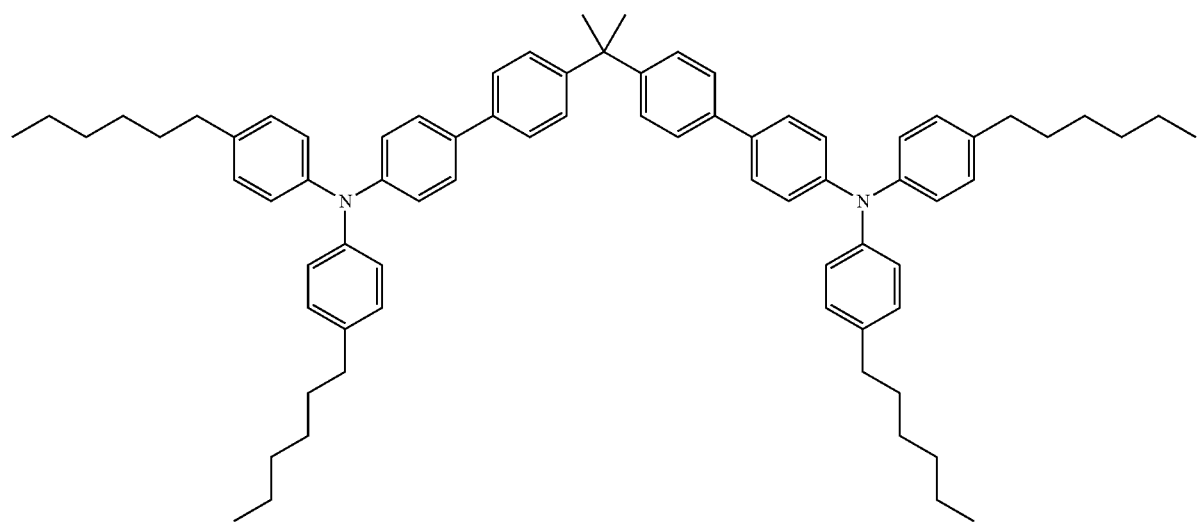

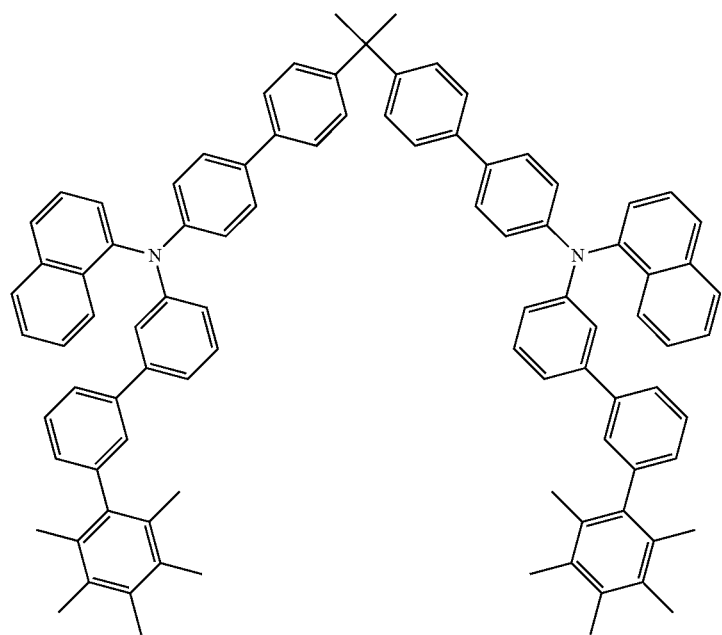
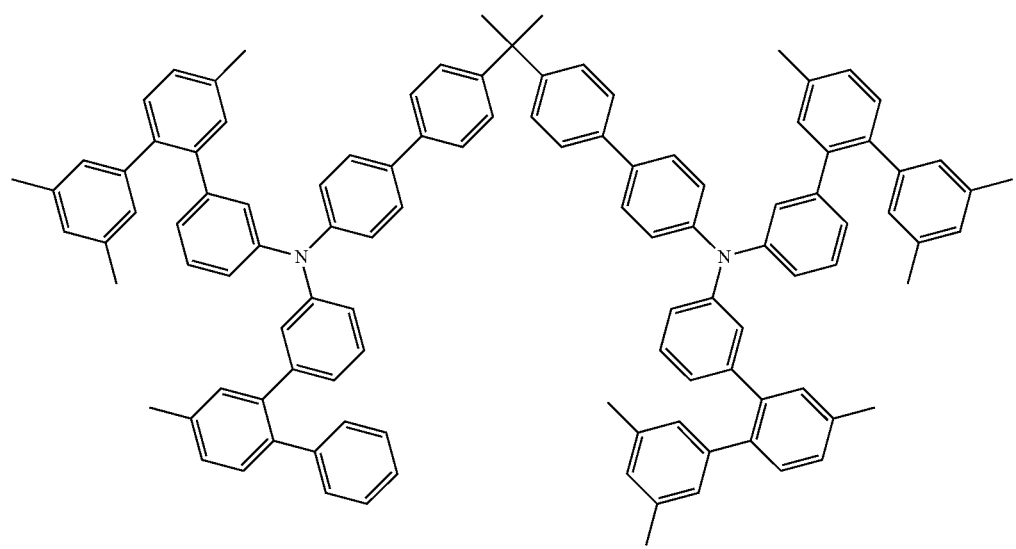

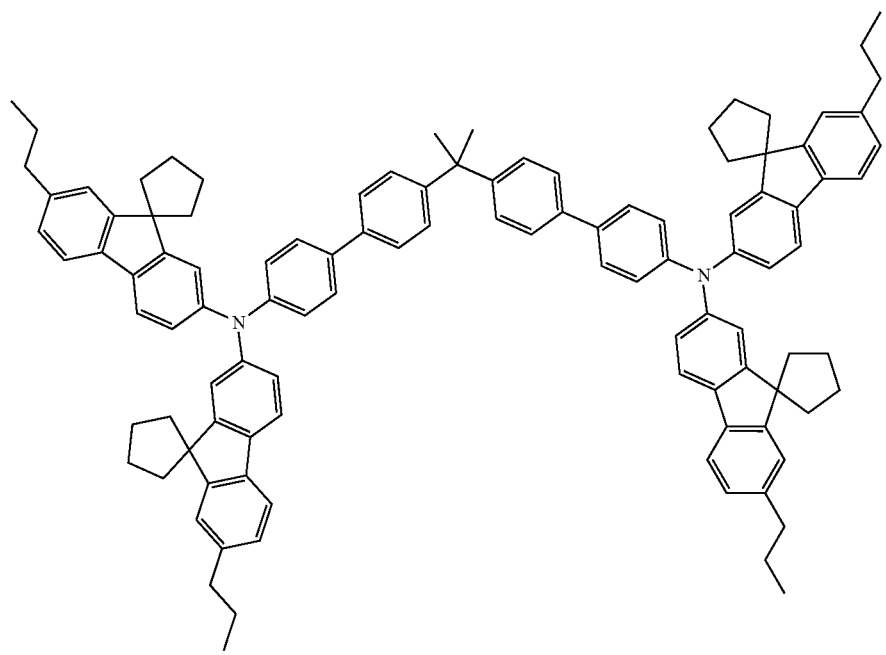
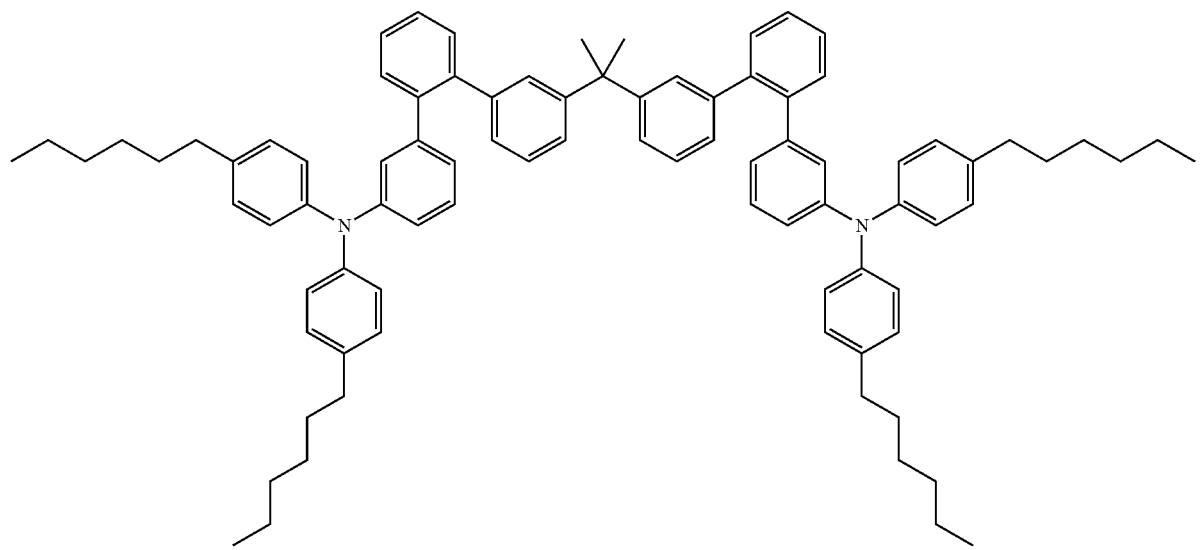
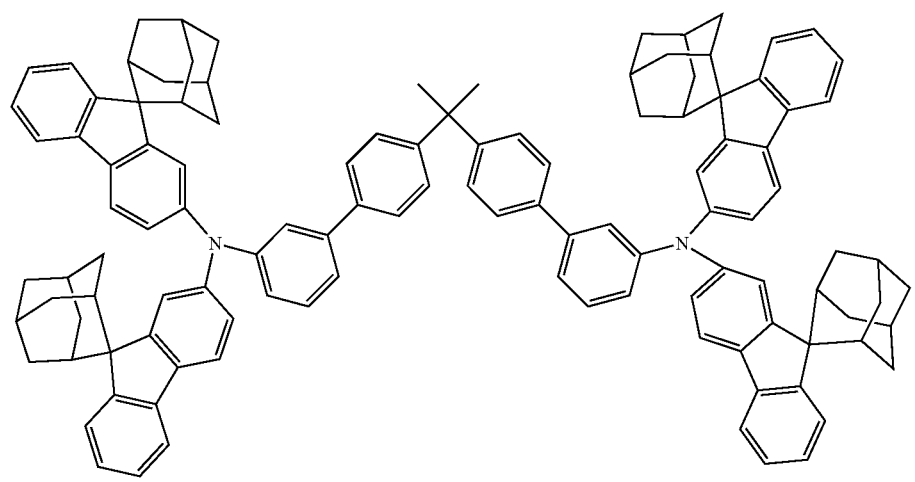

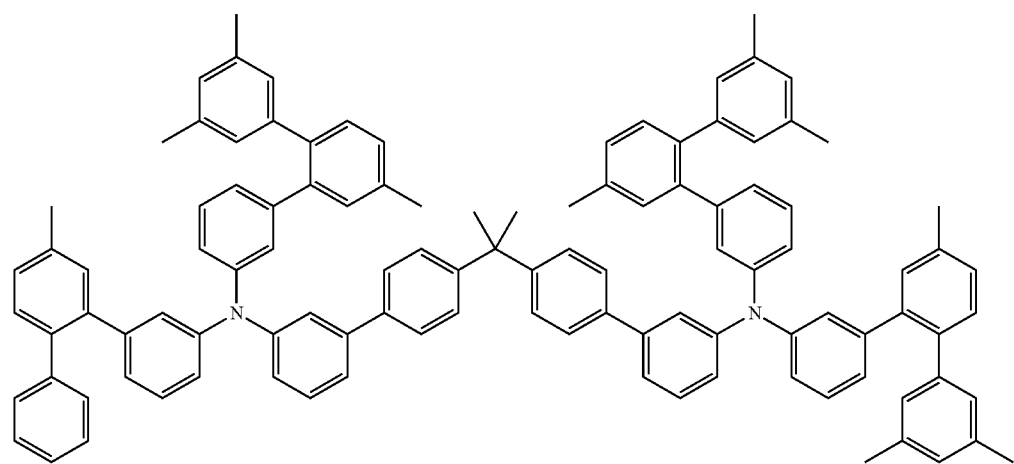
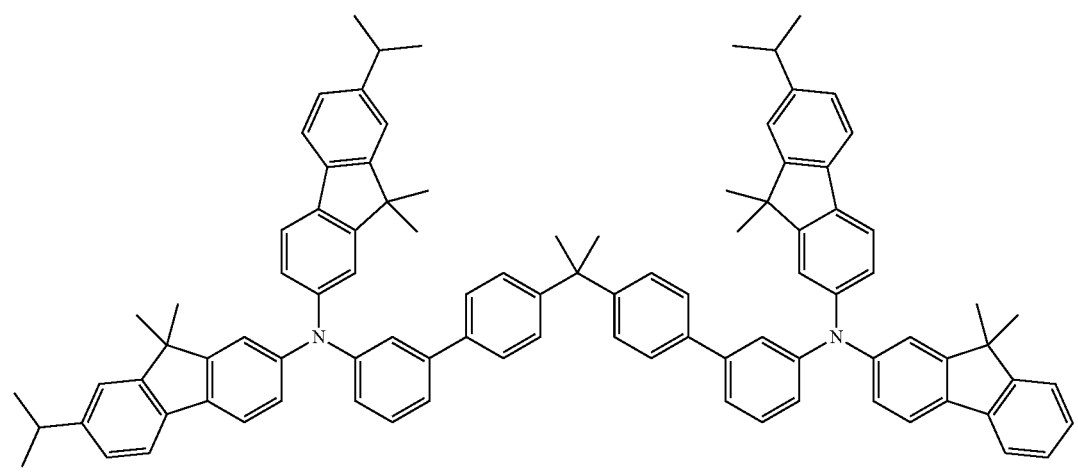
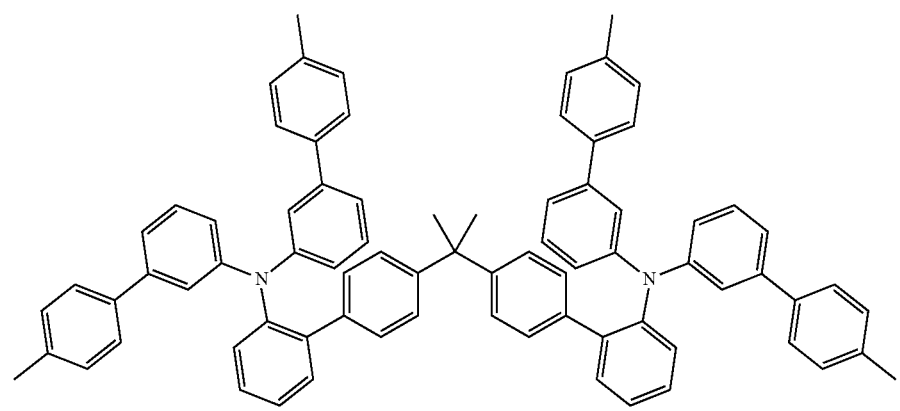

-continued
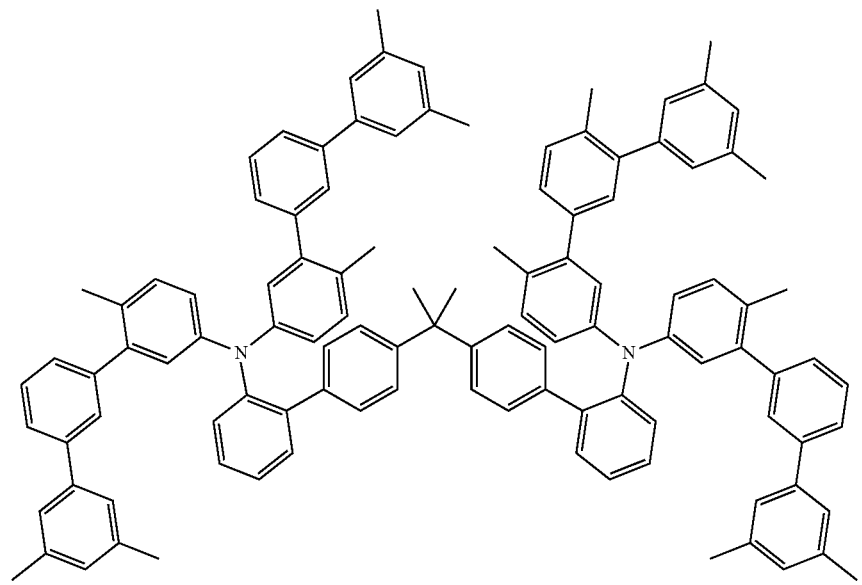
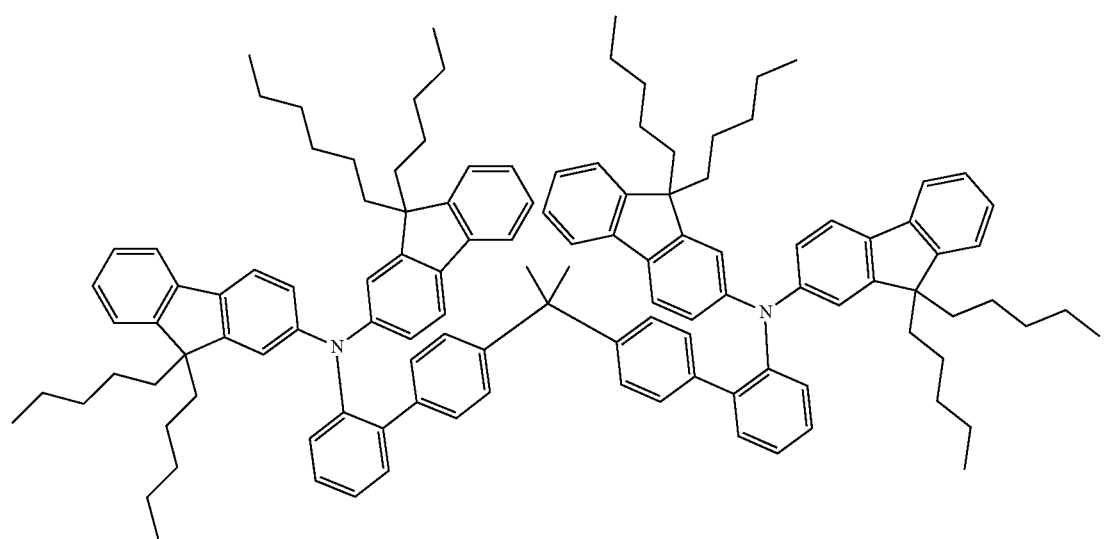

-continued
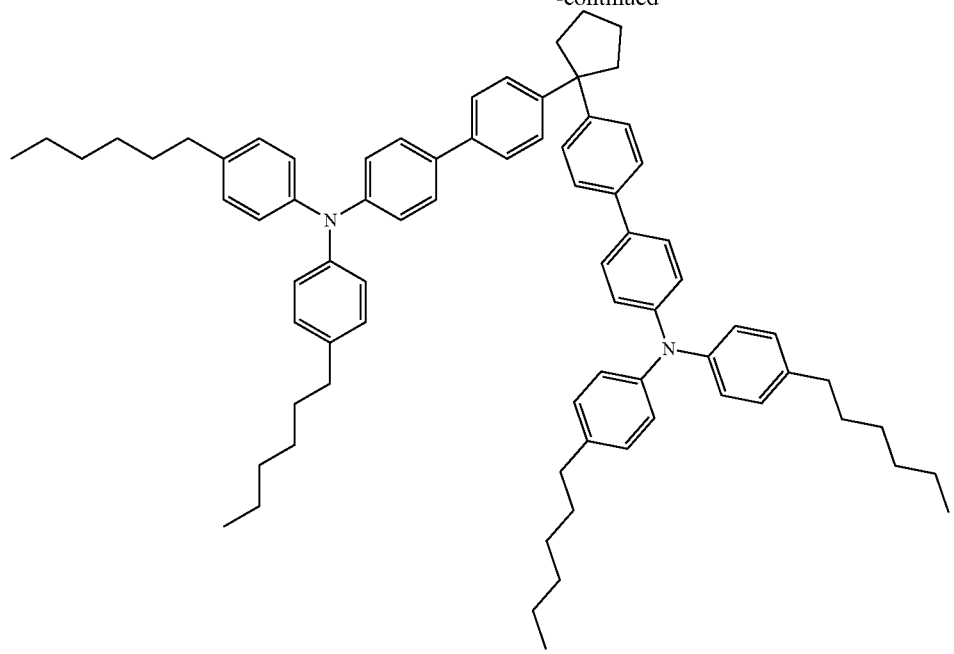
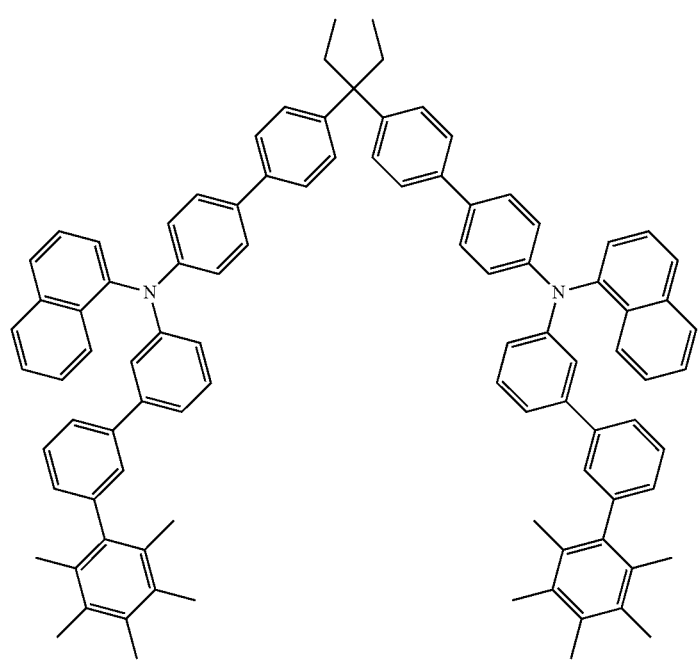

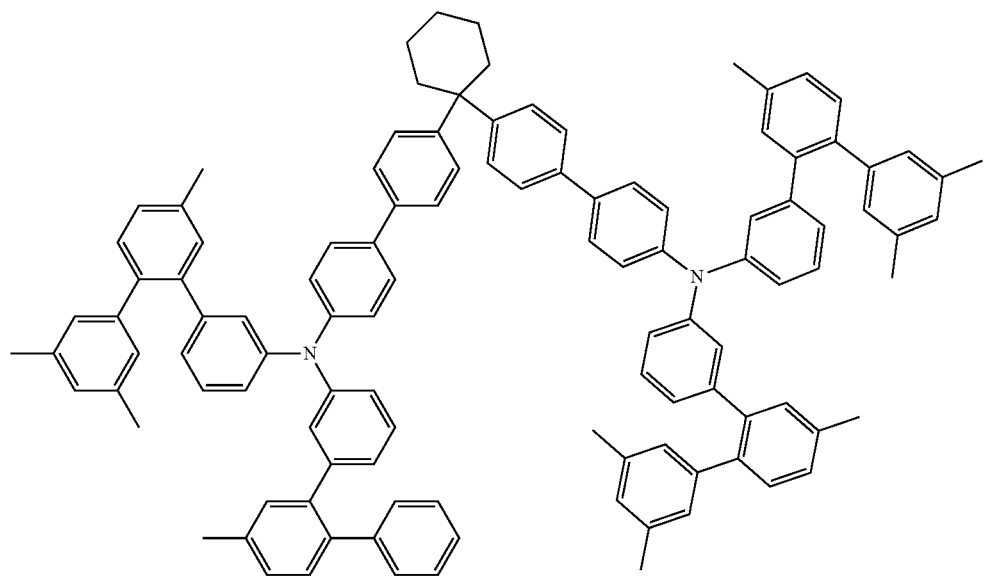
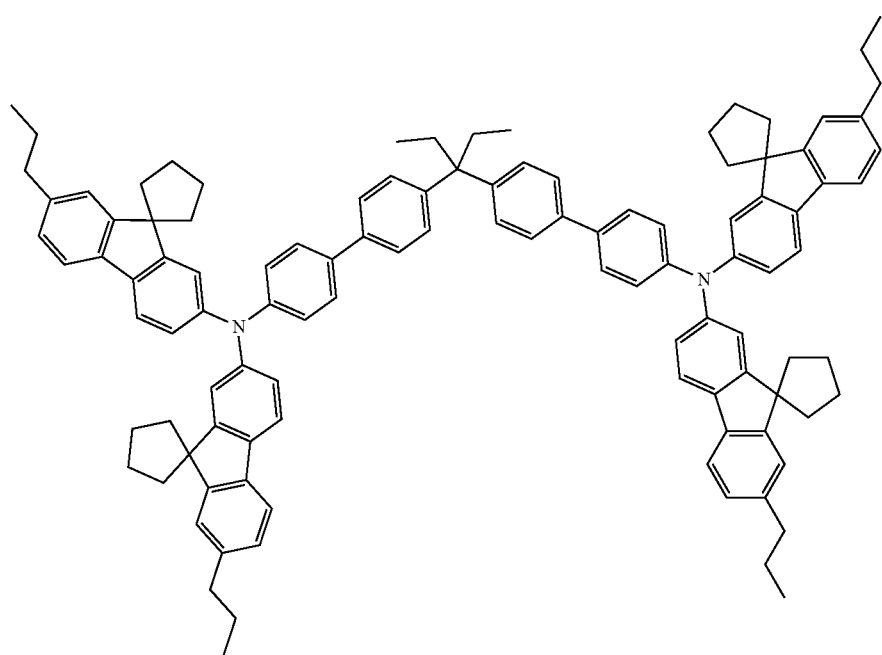

-continued
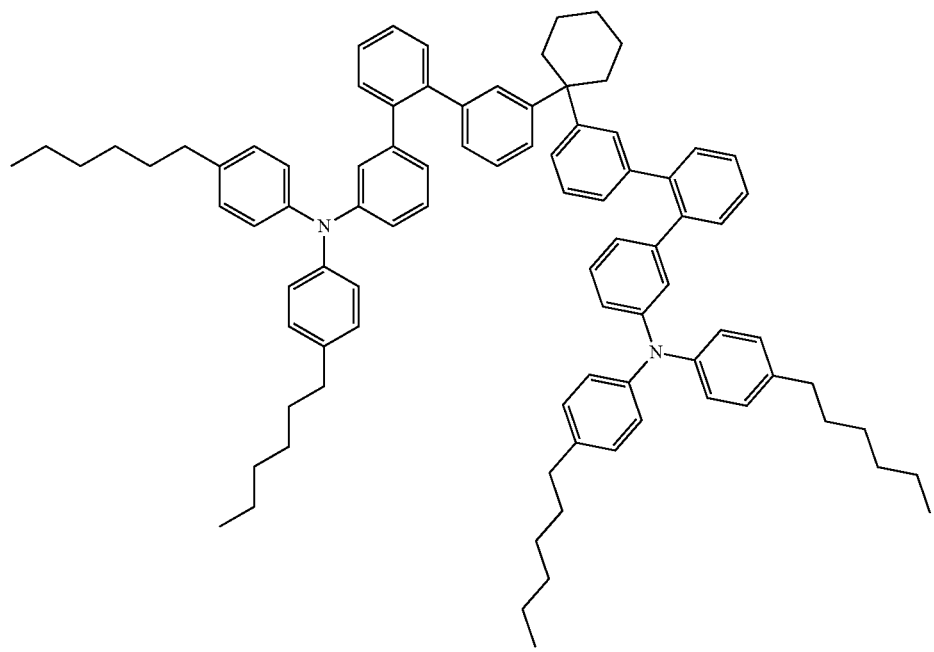
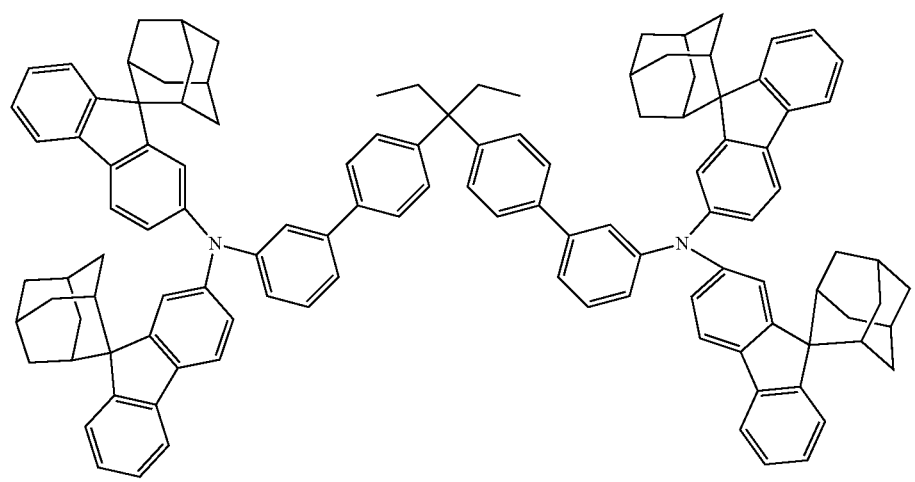

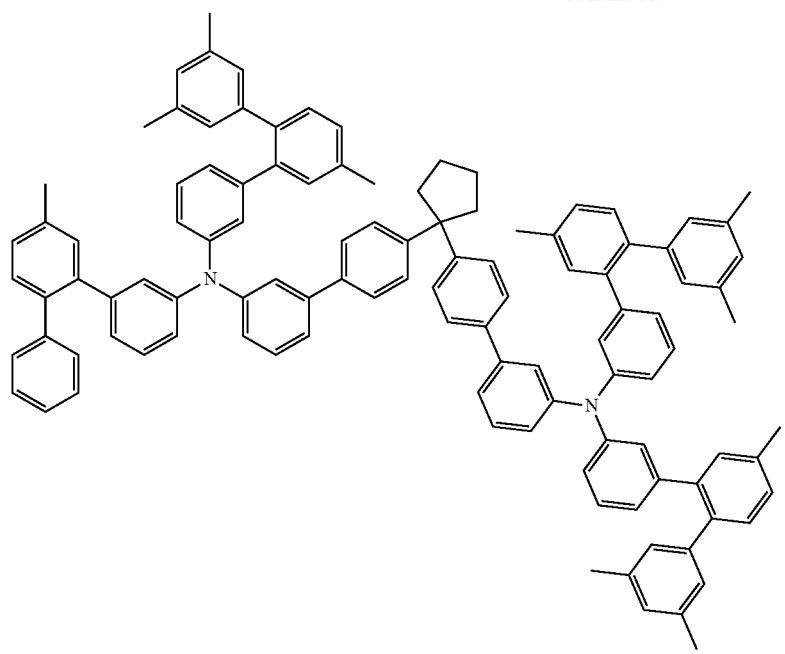
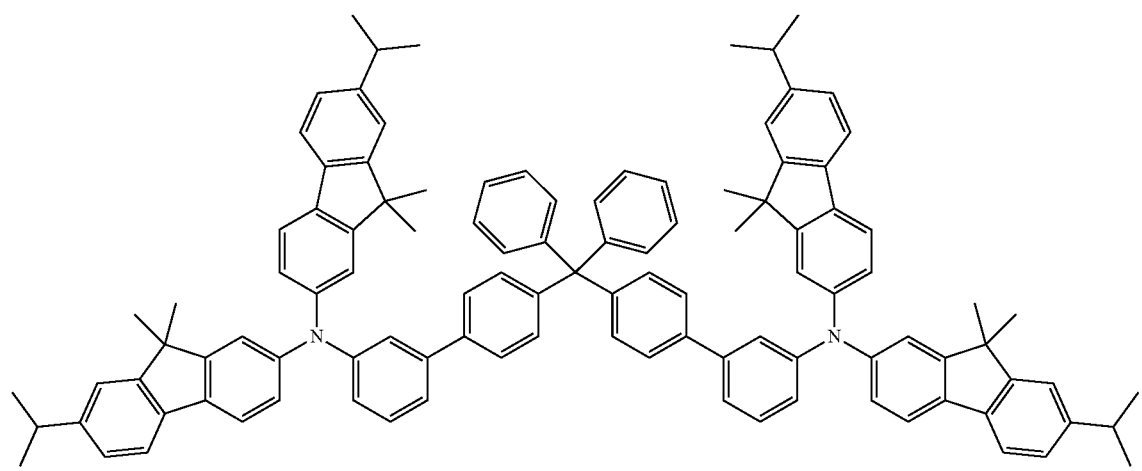
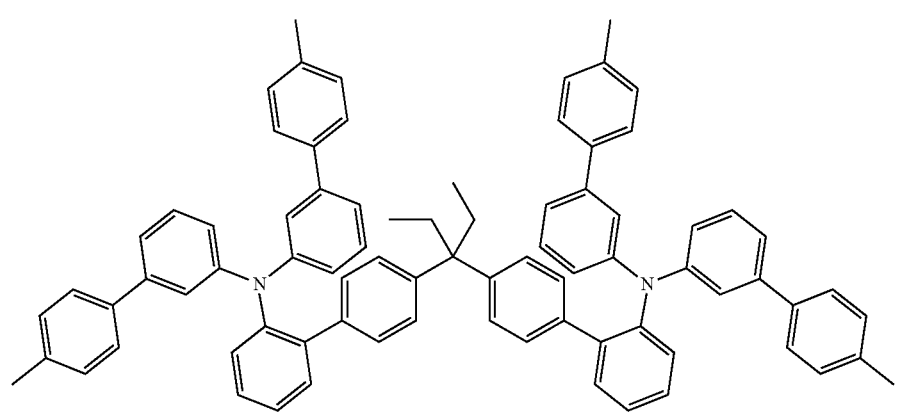

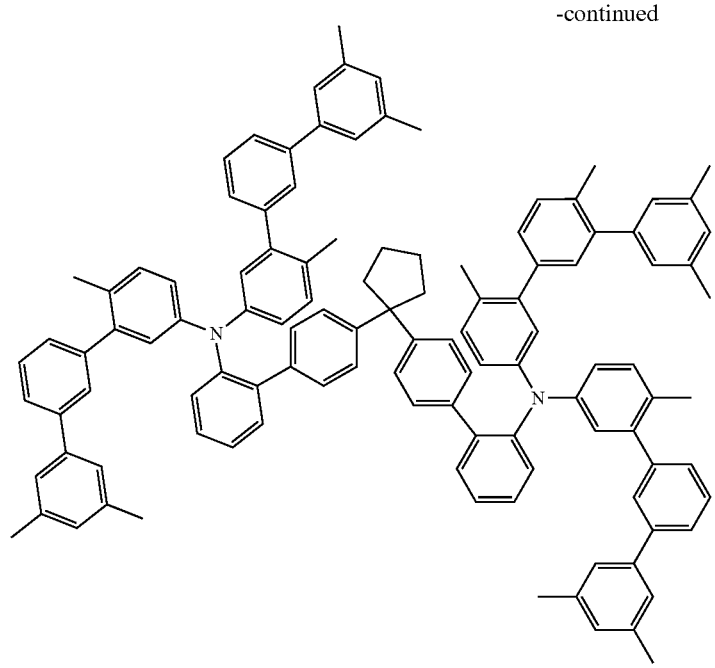
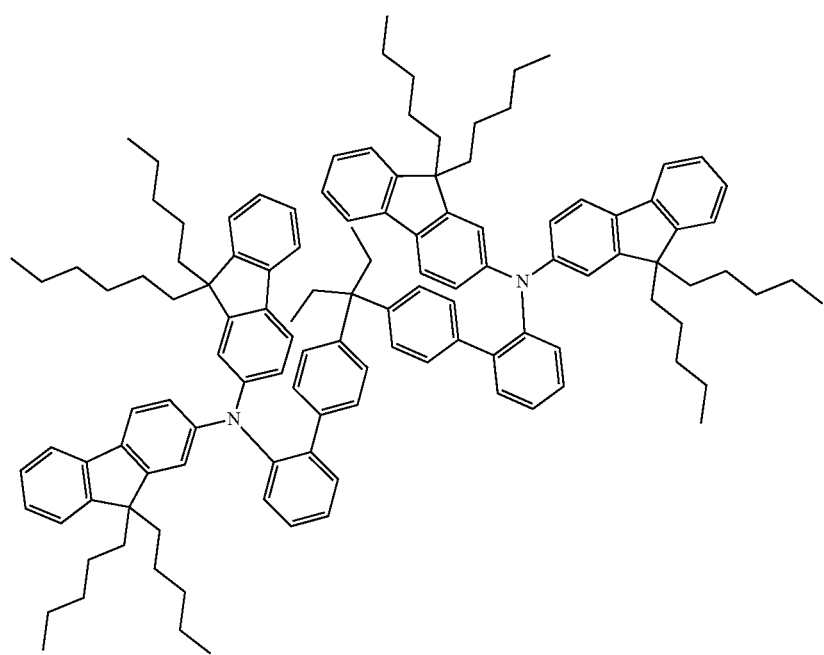

-continued
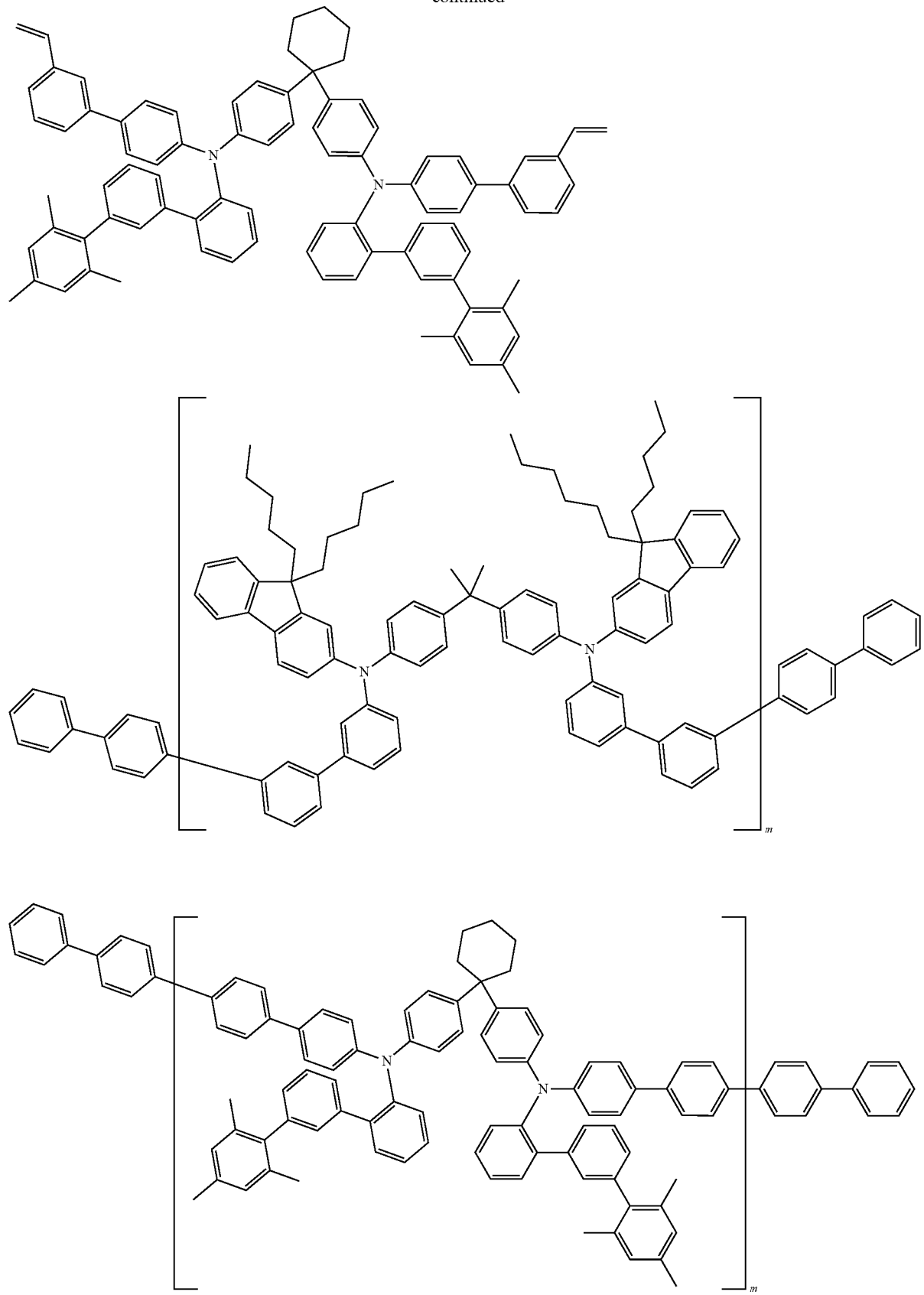

wherein in the structural formulae, m is an integer of 2 or greater.

19. An organic light emitting device comprising:

a first electrode:

a second electrode provided to face the first electrode; and an organic material layer having one or more layers provided between the first electrode and the second electrode, wherein one or more layers of the organic material layer include the compound of claim 18.

20. An organic light emitting device comprising:

a first electrode;

a second electrode provided to face the first electrode; and an organic material layer having one or more layers provided between the first electrode and the second electrode, wherein one or more layers of the organic material layer include a composition comprising a compound of the following Chemical Formula 1 having a molecular weight greater than or equal to 1,000 g/mol or a cured material thereof, wherein the organic material layer includes a light emitting layer, and wherein the light emitting layer includes a fluorescent dopant, and the fluorescent dopant is an arylamine compound including an anthracene group or a chrysene group:

[Chemical Formula 1]

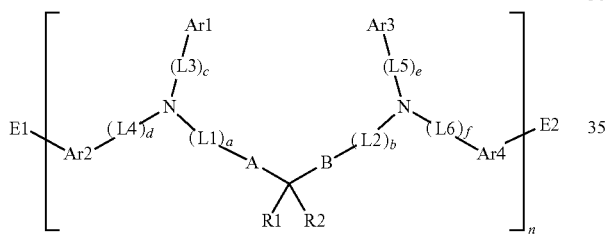

wherein, in Chemical Formula 1:

R1 and R2 are the same as each other, and are hydrogen, deuterium, an alkyl group having 1 to 15 carbon atoms, or an aryl group having 6 to 10 carbon atoms, or bond to each other to form a cycloalkyl group;

A and B are the same as each other, and are a substituted or unsubstituted phenylene group;

L1 and L2 are the same as each other, L3 and L5 are the same as each other, L4 and L6 are the same as each other, and L1 to L6 are a substituted or unsubstituted arylene group;

Ar2 and Ar4 are the same as each other, and a substituted or unsubstituted arylene group;

Ar1 and Ar3 are the same as each other, and are a substituted or unsubstituted aryl group;

at least one of L1, L2, L4, L6, Ar2 and Ar4 is substituted with an alkyl group, a cycloalkyl group, or an adamantyl group:

at least one of L3 and L5 is substituted with a cycloalkyl group or an adamantyl group:

at least one of Ar1 and Ar3 is substituted with an alkyl group or an adamantyl group;

E1 and E2 are the same as each other, and are hydrogen, deuterium, a halogen group, a substituted or unsubstituted alkyl group, a substituted or unsubstituted aryl group, or a substituted or unsubstituted siloxane group:

a and b are each an integer of 1 to 5, and c to f are each an integer of 0 to 5, and when a to f are an integer of 2 to 5, linking groups in the parentheses are the same as or different from each other:

n is an integer of 1 or greater, and when n is 1, E1 and E2 are hydrogen or deuterium: and when R1 and R2 are a phenyl group and n is 1, Ar1 and Ar3 are a phenyl group substituted with an alkyl group or an alkenyl group, or a substituted or unsubstituted polycyclic aryl group; and Ar2 and Ar4 are a phenylene group substituted with an alkyl group or an alkenyl group: or a substituted or unsubstituted polycyclic arylene group.

* * * * *